(12) United States Patent
Vaughan et al.

(10) Patent No.: US 12,205,725 B2
(45) Date of Patent: Jan. 21, 2025

(54) METHODS AND APPARATUS FOR EVALUATING DEVELOPMENTAL CONDITIONS AND PROVIDING CONTROL OVER COVERAGE AND RELIABILITY

(71) Applicant: Cognoa, Inc., Palo Alto, CA (US)

(72) Inventors: Brent Vaughan, Portola Valley, CA (US); Clara Lajonchere, Los Angeles, CA (US); Dennis Wall, Palo Alto, CA (US); Abdelhalim Abbas, San Jose, CA (US); Jeffrey Ford Garberson, Redwood City, CA (US)

(73) Assignee: Cognoa, Inc., Palo Alto, CA (US)

( * ) Notice: Subject to any disclaimer, the term of this patent is extended or adjusted under 35 U.S.C. 154(b) by 0 days.

(21) Appl. No.: 17/591,190

(22) Filed: Feb. 2, 2022

(65) Prior Publication Data
US 2022/0157466 A1    May 19, 2022

Related U.S. Application Data

(63) Continuation of application No. 16/155,794, filed on Oct. 9, 2018, now abandoned, which is a continuation
(Continued)

(51) Int. Cl.
*G16H 50/30*    (2018.01)
*G06N 20/00*    (2019.01)
(Continued)

(52) U.S. Cl.
CPC .............. *G16H 50/30* (2018.01); *G06N 20/00* (2019.01); *G16H 20/10* (2018.01); *G16H 20/70* (2018.01); *G16H 50/20* (2018.01); *G16H 50/70* (2018.01)

(58) Field of Classification Search
CPC ........ G16H 50/30; G16H 20/10; G16H 20/70; G16H 50/20; G16H 50/70; G06N 20/00
(Continued)

(56) References Cited

U.S. PATENT DOCUMENTS 4,860,214 A    8/1989    Matsuda et al.
5,722,418 A    3/1998    Bro
(Continued)

FOREIGN PATENT DOCUMENTS

CA    2857069 A1    5/2013
CN    1918575 A    2/2007
(Continued)

OTHER PUBLICATIONS

Duda et al., Use of Machine Learning for Behavioral Distinction of Autism and ADHD. Transl Psychiatry 6(2):e732 (2016).
(Continued)

*Primary Examiner* — Mamon Obeid
*Assistant Examiner* — Teresa S Williams
(74) *Attorney, Agent, or Firm* — Wilson Sonsini Goodrich & Rosati

(57) ABSTRACT

The methods and apparatus disclosed herein can evaluate a subject for a developmental condition or conditions and provide improved sensitivity and specificity for categorical determinations indicating the presence or absence of the developmental condition by isolating hard-to-screen cases as inconclusive. The methods and apparatus disclosed herein can be configured to be tunable to control the tradeoff between coverage and reliability and to adapt to different application settings and can further be specialized to handle different population groups.

19 Claims, 30 Drawing Sheets

Related U.S. Application Data of application No. PCT/US2017/061552, filed on Nov. 14, 2017.

(60) Provisional application No. 62/452,908, filed on Jan. 31, 2017, provisional application No. 62/421,958, filed on Nov. 14, 2016.

(51) Int. Cl.
*G16H 20/10* (2018.01)
*G16H 20/70* (2018.01)
*G16H 50/20* (2018.01)
*G16H 50/70* (2018.01)

(58) Field of Classification Search
USPC .......................................................... 705/3
See application file for complete search history.

(56) References Cited

U.S. PATENT DOCUMENTS

| | | | |
|---|---|---|---|
| 5,807,114 A | 9/1998 | Hodges et al. |
| 6,186,145 B1 | 2/2001 | Brown |
| 6,425,764 B1 | 7/2002 | Lamson |
| 6,569,093 B2 | 5/2003 | Iliff |
| 6,957,202 B2 | 10/2005 | Skaanning et al. |
| 7,043,439 B2 | 5/2006 | Jost et al. |
| 7,155,421 B1 | 12/2006 | Haldar |
| 7,311,666 B2 | 12/2007 | Stupp et al. |
| 7,958,066 B2 | 6/2011 | Pinckney et al. |
| 7,974,872 B2 | 7/2011 | Katayama et al. |
| 8,024,332 B2 | 9/2011 | Cao et al. |
| 8,655,817 B2 | 2/2014 | De Bruin et al. |
| 8,834,174 B2 | 9/2014 | Malik |
| 9,305,059 B1 | 4/2016 | Glickman et al. |
| 9,443,199 B2 | 9/2016 | Pinckney et al. |
| 9,443,205 B2 | 9/2016 | Wall |
| 10,052,057 B2 | 8/2018 | Klin et al. |
| 10,311,645 B1 | 6/2019 | Ravindran et al. |
| 10,478,112 B2 | 11/2019 | Wall |
| 10,687,751 B2 | 6/2020 | Wall |
| 10,839,950 B2 | 11/2020 | Vaughan |
| 10,874,355 B2 | 12/2020 | Vaughan et al. |
| 10,984,899 B2 | 4/2021 | Vaughan |
| 11,024,422 B2 | 6/2021 | Wall |
| 11,176,444 B2 | 11/2021 | Wall et al. |
| 2001/0034615 A1 | 10/2001 | Wilkinson et al. |
| 2001/0036444 A1 | 11/2001 | Placke et al. |
| 2002/0002325 A1 | 1/2002 | Iliff |
| 2002/0019747 A1 | 2/2002 | Ware et al. |
| 2002/0035486 A1 | 3/2002 | Huyn et al. |
| 2002/0042786 A1 | 4/2002 | Scarborough et al. |
| 2003/0032069 A1 | 2/2003 | Muraca |
| 2003/0191680 A1 | 10/2003 | Dewar |
| 2004/0015337 A1 | 1/2004 | Thomas et al. |
| 2004/0103001 A1 | 5/2004 | Mazar et al. |
| 2004/0147840 A1 | 7/2004 | Duggirala et al. |
| 2004/0197750 A1 | 10/2004 | Donaher et al. |
| 2004/0210159 A1 | 10/2004 | Kibar |
| 2004/0265784 A1 | 12/2004 | Stout |
| 2005/0075887 A1 | 4/2005 | Bernard et al. |
| 2005/0142524 A1 | 6/2005 | Simon et al. |
| 2005/0176057 A1 | 8/2005 | Bremer et al. |
| 2005/0187802 A1 | 8/2005 | Koeppel |
| 2005/0197988 A1 | 9/2005 | Bublitz |
| 2005/0209785 A1 | 9/2005 | Wells et al. |
| 2005/0216243 A1 | 9/2005 | Graham et al. |
| 2005/0260549 A1 | 11/2005 | Feierstein et al. |
| 2006/0009683 A1 | 1/2006 | Sakai et al. |
| 2006/0059145 A1 | 3/2006 | Henschke et al. |
| 2006/0078856 A1 | 4/2006 | Kellman |
| 2006/0282306 A1 | 12/2006 | Thissen-Roe |
| 2007/0118399 A1 | 5/2007 | Avinash et al. |
| 2007/0207449 A1 | 9/2007 | Feierstein |
| 2008/0014566 A1 | 1/2008 | Chapman et al. |
| 2008/0016024 A1 | 1/2008 | Andoh et al. |
| 2009/0007924 A1 | 1/2009 | Iliff |
| 2009/0016559 A1 | 1/2009 | Cleary |
| 2009/0016599 A1 | 1/2009 | Eaton et al. |
| 2009/0083075 A1 | 3/2009 | Henschke et al. |
| 2009/0124886 A1 | 5/2009 | Wang et al. |
| 2009/0137923 A1 | 5/2009 | Suffin et al. |
| 2009/0182578 A1 | 7/2009 | Ozersky |
| 2009/0259494 A1 | 10/2009 | Feder et al. |
| 2010/0023346 A1 | 1/2010 | Paty et al. |
| 2010/0068687 A1 | 3/2010 | Bertelsen |
| 2010/0177950 A1 | 7/2010 | Donovan et al. |
| 2010/0179928 A1 | 7/2010 | Hodgin |
| 2010/0184093 A1 | 7/2010 | Donovan et al. |
| 2010/0189818 A1 | 7/2010 | Tsai |
| 2010/0280760 A1 | 11/2010 | Pi et al. |
| 2010/0332430 A1 | 12/2010 | Caraviello et al. |
| 2011/0082712 A1 | 4/2011 | Eberhardt, III et al. |
| 2011/0119212 A1 | 5/2011 | De Bruin et al. |
| 2011/0145161 A1 | 6/2011 | Scarborough et al. |
| 2011/0184379 A1 | 7/2011 | Van Antwerp et al. |
| 2011/0218253 A1 | 9/2011 | Lange et al. |
| 2012/0004925 A1 | 1/2012 | Braverman et al. |
| 2012/0028816 A1 | 2/2012 | Warren et al. |
| 2012/0059282 A1 | 3/2012 | Agichtein et al. |
| 2012/0101852 A1 | 4/2012 | Albert |
| 2012/0102405 A1 | 4/2012 | Zuckerman et al. |
| 2012/0108909 A1 | 5/2012 | Slobounov et al. |
| 2012/0270199 A1 | 10/2012 | Malik |
| 2013/0159010 A1 | 6/2013 | Paty et al. |
| 2013/0178731 A1 | 7/2013 | Bosl |
| 2013/0184603 A1 | 7/2013 | Rothman |
| 2013/0184792 A1 | 7/2013 | Simon et al. |
| 2013/0262357 A1 | 10/2013 | Amarasingham et al. |
| 2013/0267441 A1 | 10/2013 | Momeni et al. |
| 2014/0006319 A1 | 1/2014 | Anand et al. |
| 2014/0024553 A1 | 1/2014 | Michalek et al. |
| 2014/0052474 A1 | 2/2014 | Madan et al. |
| 2014/0063236 A1 | 3/2014 | Shreve et al. |
| 2014/0074848 A1 | 3/2014 | Kettunen et al. |
| 2014/0092006 A1 | 4/2014 | Boelter et al. |
| 2014/0122109 A1 | 5/2014 | Ghanbari et al. |
| 2014/0141983 A1 | 5/2014 | Singh et al. |
| 2014/0148728 A1 | 5/2014 | Eizenman et al. |
| 2014/0219986 A1 | 8/2014 | Greene et al. |
| 2014/0223462 A1 | 8/2014 | Aimone et al. |
| 2014/0253876 A1 | 9/2014 | Klin et al. |
| 2014/0279746 A1 | 9/2014 | De Bruin et al. |
| 2014/0304200 A1 | 10/2014 | Wall |
| 2014/0315168 A1* | 10/2014 | Movellan ............... A61B 5/165 |
| | | | 434/236 |
| 2014/0330576 A1 | 11/2014 | Bauer |
| 2014/0336539 A1* | 11/2014 | Torres .................... A61B 5/162 |
| | | | 600/595 |
| 2014/0342321 A1 | 11/2014 | Wendt |
| 2014/0343450 A1 | 11/2014 | Stack |
| 2015/0004588 A1 | 1/2015 | Vats et al. |
| 2015/0006192 A1 | 1/2015 | Sudharsan et al. |
| 2015/0080671 A1 | 3/2015 | Christensen et al. |
| 2015/0099946 A1 | 4/2015 | Sahin |
| 2015/0119437 A1 | 4/2015 | Clark et al. |
| 2015/0154372 A1 | 6/2015 | Soenksen et al. |
| 2015/0197543 A1 | 7/2015 | Glass et al. |
| 2015/0315182 A1 | 11/2015 | Lee et al. |
| 2016/0022137 A1 | 1/2016 | Wetzel et al. |
| 2016/0046990 A1 | 2/2016 | Hensel |
| 2016/0135706 A1 | 5/2016 | Sullivan et al. |
| 2016/0140859 A1 | 5/2016 | Jiao et al. |
| 2016/0180038 A1 | 6/2016 | Clark et al. |
| 2016/0180248 A1 | 6/2016 | Regan |
| 2016/0203280 A1 | 7/2016 | Neville |
| 2016/0209428 A1 | 7/2016 | Naviaux et al. |
| 2016/0232328 A1 | 8/2016 | Sklar et al. |
| 2016/0342756 A1 | 11/2016 | Wall |
| 2016/0357924 A1 | 12/2016 | Jenkins |
| 2017/0035792 A1 | 2/2017 | Montagnier et al. |
| 2017/0069216 A1 | 3/2017 | Vaughan et al. |
| 2017/0091423 A1 | 3/2017 | Kumar et al. |
| 2017/0160878 A1 | 6/2017 | Endo et al. |

(56) References Cited

U.S. PATENT DOCUMENTS

| | | |
|---|---|---|
| 2017/0169178 A1 | 6/2017 | Beehler et al. |
| 2017/0188930 A1 | 7/2017 | Lahvis |
| 2017/0262609 A1 | 9/2017 | Perlroth et al. |
| 2017/0344713 A1 | 11/2017 | Riistama et al. |
| 2017/0365101 A1 | 12/2017 | Samec et al. |
| 2018/0098724 A1 | 4/2018 | Lu et al. |
| 2018/0132780 A1 | 5/2018 | Saar |
| 2018/0184964 A1 | 7/2018 | Simon et al. |
| 2018/0366144 A1 | 12/2018 | Ashoori et al. |
| 2019/0019581 A1 | 1/2019 | Vaughan et al. |
| 2019/0038202 A1 | 2/2019 | Wall |
| 2019/0043610 A1 | 2/2019 | Vaughan |
| 2019/0043618 A1 | 2/2019 | Vaughan et al. |
| 2019/0043619 A1 | 2/2019 | Vaughan et al. |
| 2019/0088366 A1 | 3/2019 | Vaughan et al. |
| 2019/0244127 A1 | 8/2019 | Amado et al. |
| 2021/0068766 A1 | 3/2021 | Vaughan et al. |
| 2021/0133509 A1 | 5/2021 | Wall et al. |
| 2021/0174919 A1 | 6/2021 | Vaughan |
| 2021/0335489 A1 | 10/2021 | Wall |
| 2022/0369976 A1 | 11/2022 | Abbas et al. |
| 2023/0092866 A1 | 3/2023 | Vaughan et al. |

FOREIGN PATENT DOCUMENTS

| | | |
|---|---|---|
| CN | 101149767 A | 3/2008 |
| CN | 101499078 A | 8/2009 |
| CN | 101821741 A | 9/2010 |
| CN | 102663129 A | 9/2012 |
| CN | 102971755 A | 3/2013 |
| CN | 103473631 A | 12/2013 |
| CN | 103493054 A | 1/2014 |
| CN | 103714261 A | 4/2014 |
| CN | 104254863 A | 12/2014 |
| CN | 104427932 A | 3/2015 |
| CN | 104504297 A | 4/2015 |
| CN | 104902806 A | 9/2015 |
| CN | 104956391 A | 9/2015 |
| CN | 113873935 A | 12/2021 |
| EP | 0424869 | 2/1991 |
| EP | 3941340 A1 | 1/2022 |
| JP | 2001034688 A | 2/2001 |
| JP | 2002318858 A | 10/2002 |
| JP | 2006507875 A | 3/2006 |
| JP | 2007249878 A | 9/2007 |
| JP | 2011255106 A | 12/2011 |
| JP | 2012509480 A | 4/2012 |
| JP | 2014506244 A | 3/2014 |
| JP | 2015228202 A | 12/2015 |
| JP | 2016532481 A | 10/2016 |
| JP | 2017504087 A | 2/2017 |
| JP | 2021184816 A | 12/2021 |
| JP | 7001593 B2 | 1/2022 |
| JP | 2022009339 A | 1/2022 |
| WO | WO-9521419 A1 | 8/1995 |
| WO | WO-9705553 A1 | 2/1997 |
| WO | WO-2008124138 A1 | 10/2008 |
| WO | WO-2010059709 A2 | 5/2010 |
| WO | WO-2012082056 A1 | 6/2012 |
| WO | WO-2013062937 A2 | 5/2013 |
| WO | WO-2014127065 A2 | 8/2014 |
| WO | WO-2014164858 A1 | 10/2014 |
| WO | WO-2015006364 A2 | 1/2015 |
| WO | WO-2015066203 A2 | 5/2015 |
| WO | WO-2016110804 A1 | 7/2016 |
| WO | WO-2017027709 A1 | 2/2017 |
| WO | WO-2017106770 A1 | 6/2017 |
| WO | WO-2018090009 A1 | 5/2018 |
| WO | WO-2018148365 A1 | 8/2018 |
| WO | WO-2020198065 A1 | 10/2020 |
| WO | WO-2020227703 A1 * | 11/2020 ............... A61B 5/16 |
| WO | WO-2021046412 A1 | 3/2021 |

OTHER PUBLICATIONS

Elder et al., Clinical impact of early diagnosis of autism on the prognosis and parent-child relationships. Psychology Research and Behavior Management 10: 283-292 (2017).

Golarai, G. et al. Autism and the development of face processing. Clinical Neuroscience Research 6:145-160 (2006).

Kosmicki, et al. Searching for a minimal set of behaviors for autism detection through feature selection-based machine learning. Transl Psychiatry. Feb. 24, 2015;5:e514 . . . .

PCT/US2017/061552 International Search Report and Written Opinion dated Mar. 26, 2018.

Plajner et al., Bayesian Network Models for Adaptive Testing; Proceedings of the Twelfth Bayesian Modeling Applications Workshop, co-located with the 31st Conference on Uncertainty in Artificial Intelligence; Amsterdam, The Netherlands, Jul. 16, 2015; http://ceur-ws.org/Vol-1565/ (Year: 2015).

Spencer et al.: Attention-deficit/hyperactivity disorder and comorbidity. Pediatr Clin North Am. 46(5):915-927, vii. doi: 10.1016/s0031-3955(05)70163-2 (1999).

U.S. Appl. No. 16/155,761 Non-Final Office Action dated Apr. 2, 2020.

U.S. Appl. No. 16/155,761 Office Action dated Oct. 7, 2019.

U.S. Appl. No. 16/155,794 Final Office Action dated Aug. 15, 2019.

U.S. Appl. No. 16/155,794 Non-Final Office Action dated Apr. 1, 2021.

U.S. Appl. No. 16/155,794 Non-Final Office Action dated Apr. 16, 2020.

U.S. Appl. No. 16/155,794 Non-Final Office Action dated Jan. 14, 2019.

Van Stralen et al. Diagnostic methods I: sensitivity, specificity, and other measures of accuracy. Kidney Int. 75(12):1257-1263 (2009).

Wall et al. Use of artificial intelligence to shorten the behavioral diagnosis of autism. PLoS One. 2012;7(8):e43855.

U.S. Appl. No. 17/690,977 Office Action dated Jan. 4, 2023.

U.S. Appl. No. 17/690,977 Office Action dated Sep. 14, 2022.

Artoni et al, "Accessible education for autistic children: ABA-based didactic software", International Conference on Universal Access in Human-Computer Interaction (2011).

Atherton, G., et al., "Autism through the ages: a mixed methods approach to understanding how age and age of diagnosis affect quality of life", J Autism Dev Disord, doi: 10.1007/s10803-021-05235-x.

Bailey, et al. Autism as a strongly genetic disorder: evidence from a British twin study. Psychol Med. Jan. 1995;25(1):63-77.

Bernier, et al. Psychopathology, families, and culture: autism. Child Adolesc Psychiatr Clin N Am. Oct. 2010;19(4):855-67.

Berument, et al. Autism screening questionnaire: diagnostic validity. Br J Psychiatry. Nov. 1999;175:444-51.

Breiman et al.: Chapter 6 Medical diagnosis and prognosis. Classification and regression trees. Chappman & Hall/CRC (1984) (pp. 174-346).

Breiman. Random Forests. Machine Learning 45:5-32 (2001).

Brewer et al., Pinteresce: Exploring Reminiscence as an Incentive to Digital Reciprocity for Older Adults. CSCW'15 Companion (2015).

Cicchetti, et al. Reliability of the ADI-R: multiple examiners evaluate a single case. J Autism Dev Disord. Apr. 2008;38(4):764-70. Epub Dec. 5, 2007.

Cohen. Fast effective rule induction. Proceedings of the Twelfth International Conference on Machine Learning. (pp. 115-123) (1995).

Duda, et al. Clinical Evaluation of a Novel and Mobile Autism Risk Assessment. J Autism Dev Disord. Jun. 2016;46(6):1953-61 . . . .

Duda, et al. Testing the accuracy of an observation-based classifier for rapid detection of autism risk Transl Psychiatry. Aug. 12, 2014;4:e424 . . . .

Duda, et al. Testing the accuracy of an observation-based classifier for rapid detection of autism risk. Transl Psychiatry. Apr. 28, 2015;5:e556. (Addendum).

Fischbach, et al. The Simons Simplex Collection: a resource for identification of autism genetic risk factors. Neuron. Oct. 21, 2010;68(2):192-5.

Fisher et al., DISC Interviewer Manual. Section 2 Computerized Versions of the DISC (2006).

(56) References Cited

OTHER PUBLICATIONS

Frank, et al. A simple approach to ordinal prediction. European conference on Maching Learning; Freiburg, Germany, Springer-Verlag 2001:145-156.
Frank, et al. Data mining in bioinformatics using Weka. Bioinformatics. Oct. 12, 2004;20(15):2479-81. Epub Apr. 8, 2004.
Frank et al. Generating accurate rule sets without global optimization. In: Machine Learning: Proceedings of the Fifteenth International Conference: 1998; San Francisco, CA, Morgan Kaufmann Publishers (8 pgs).
Freund, et al. A decision-theoretic generalization of on-line learning and an application to boosting. Journal of computer and system sciences 55.1 (1997): 119-139.
Freund, et al. Experiments with a new boosting algorithm. In: Proceedings of the International Conference on Machine Learning: 1996, San Francisco, Morgan Kautinann: pp. 148-156.
Freund, et al. The alternating decision tree learning algorithm. In: Machine Learning: Proceedings of the Sixteenth International Conference. 1999, pp. 124-133.
Fusaro, et al. The potential of accelerating early detection of autism through content analysis of YouTube videos. PLoS One. Apr. 16, 2014;9(4):e93533 . . . .
Gaines, et al. Induction of ripple-down rules applied to modeling large databases. Journal of Intelligent Information Systems 5.3 (1995): 211-228.
Gama. Functional trees. Machine Learning 55:219-250 (2004).
Geschwind et al. The autism genetic resource exchange: a resource for the study of autism and related neuropsychiatric conditions. The American Journal of Human Genetics 69:463-466 (2001).
Golarai, G. et al. "Autism and the development of face processing", Clinical Neuroscience Research, 2006, vol. 6 , No. 3, pp. 145-106.
Gotham, et al. The Autism Diagnostic Observation Schedule: revised algorithms for improved diagnostic validity. J Autism Dev Disord. Apr. 2007;37(4):613-27. Epub Dec. 16, 2006.
Gura, et al. Autism spectrum disorder screening in primary care. J Dev Behav Pediatr. Jan. 2011;32(1):48-51.
Hall et al. The WEKA data mining software: an update. SIGKDD Explorations Newsletter 11:10-18 (2009).
Holmes et al. Multiclass alternating decision trees. Machine learning: ECML 2002. Springer Berlin Heidelberg, (pp. 161-172) (2002).
Holte. Very simple classification rules perform well on most commonly used datasets. Machine learning 11:63-91 (1993).
Howlin. Chapter 3—Identifying and assessing children with autism or asperger syndrome. Children with Autism and Asperger's Syndrome: A Guide for Practitioners and Carers. UK: John Wiley and Sons (1998) (pp. 52-75, 294-321).
Kobak et al. Web-based training in early autism screening: results from a pilot study. Telemed J E Health. Oct. 2011;17(8):640-4.
Kohavi. A study of cross-validation and bootstrap for accuracy estimation and model selection. In: Proceedings IJCAI-95: 1995: Montreal, Morgan Kaufmann, Los Altos, CA: 1137-1143.
Landwehr et al. Logistic model trees. Machine Learning 59:161-205 (2005).
Lee et al., How to Create Suitable Augmented Reality Application to Teach Social Skills for Children with ASD. IntechOpen 76476: 119-138 (2018).
Lord et al. Autism Diagnostic Interview—Revised: A revised version of a diagnostic interview for caregivers of individuals with possible pervasive developmental disorders. J Autism Dev Discord 24(5):659-685 (1994).
Lord, et al. Autism diagnostic observation schedule: a standardized observation of communicative and social behavior. J Autism Dev Disord. Jun. 1989;19(2):185-212.
Lord et al. The Autism Diagnostic Observation Schedule-Generic: A Standard Measure of Social and Communication Deficits Associated with the Spectrum of Autism. J Autism Dev Discord 30(3):205-223 (2000).
Martin. Instance-Based learning: Nearest neighbor with generalization. Hamilton, New Zealand, University of Waikato (83 pgs) (1995).

Mayes et al., Autism and ADHD: Overlapping and discriminating symptoms. Research in Autism Spectrum Disorders 6(1) :277-285 (2012).
Moore et al. Cached Sufficient Statistics for Efficient Machine Learning with Large Datasets. JAIR 8:67-91 (1998).
Moyer, M.W., "Gut Bacteria May Play a Role in Autism", Scientific American, Sep. 1, 2014, pp. 1-4.
PCT/US2016/067358 International Search Report and Written Opinion dated Apr. 13, 2017.
PCT/US2020/049492 International Search Report and Written Opinion dated Dec. 10, 2020.
Pinto-Martin, et al. Screening strategies for autism spectrum disorders in pediatric primary care. J Dev Behav Pediatr. Oct. 2008;29(5):345-50.
Pisula, E. Parents of children with autism: review of current research. Arch Psychiatry Psychother, 2003, 5: 51-63.
Planjner, Slide presentation on Bayesian Network Models for Adaptive Testing: Proceeding of the Twelfth Bayesian Modeling Applications Workshop (2015).
Quinlan. C4. 5: Programming for machine learning. Morgan Kaufmann (6 pgs) (1993).
Risi, et al. Combining information from multiple sources in the diagnosis of autism spectrum disorders. Journal of the American Academy of Child & Adolescent Psychiatry, 2006, 45(9): 1094-1103.
Robins, et al. The Modified Checklist for Autism in Toddlers: an initial study investigating the early detection of autism and pervasive developmental disorders. J Autism Dev Disord. Apr. 2001;31(2):131-44.
Santosh et al. The construction and validation of a short form of the developmental, diagnostic and dimensional interview. Eur Child Adolesc Psychiatry. Aug. 2009;18(8):521-4.
Sasagawa, Karen et al. A trial evaluation of communication abilities using a log versatile communication aid VCAN/3A. The Institue of Electronics. vol. 114, No. 512 (2015): 119-124.
Shattuck, et al. Timing of identification among children with an autism spectrum disorder: findings from a population-based surveillance study. J Am Acad Child Adolesc Psychiatry. May 2009;48(5):474-83.
Shi. Best-first decision tree learning. Master Thesis, The University of Waikato (120 pgs) (2007).
Sok et al.: Multivariate alternating decision trees, Pattern Recognition, 50:195-209 doi:10.1016/j.patcog.2015.08.014 (2016).
Tadevosyan-Leyfer, et al. A principal components analysis of the Autism Diagnostic Interview—Revised. J Am Acad Child Adolesc Psychiatry. Jul. 2003;42(7):864-72.
U.S. Appl. No. 16/155,758 Office Action dated Sep. 21, 2023.
U.S. Appl. No. 17/690,977 Office Action dated Aug. 29, 2023.
Wall, et al. Use of machine learning to shorten observation-based screening and diagnosis of autism. Transl Psychiatry. Apr. 10, 2012;2:e100.
Ward et al, The Autistic Behavioural Indicators Instrument (ABII): Development and instrument utility in discriminating autistic disorder from speech and language impairment and typical development, Research in Autism Spectrum Disorders 4.1 (2010): 28-42.
Wenner, M. Gut Bacteria May Play a Role in Autism. Scientific American, pp. 1-4, Sep. 1, 2014.
Wiggins, et al. Examination of the time between first evaluation and first autism spectrum diagnosis in a population-based sample. J Dev Behav Pediatr. Apr. 2006;27(2 Suppl):S79-87.
Witten et al. Data Mining: Practical Machine Learning Tools and Techniques with Java Implementations. Morgan Kaufmann, Amsterdam, Second Edition (558 pgs) (Oct. 2005).
Witten et al, Weka: Practical Machine Learning Tools and Techniques with Java Implementations, University of Waikato, Department of Computer Science, 1999. (4pp).
Australian Patent Application No. 2018219846 Examination Report No. 1 dated Feb. 16, 2022.
Canadian Patent Application No. 2,857,069 Office Action dated Jun. 18, 2019.
Chinese Patent Application No. 2016800821848 Decision of Rejection dated Apr. 24, 2022.

(56) References Cited

OTHER PUBLICATIONS

Chinese Patent Application No. 201680082184.8 Second Office Action dated Sep. 9, 2021.
EP12844474.2 Extended European Search Report dated Jun. 26, 2015.
EP16876856.2 Supplementary European Search Report dated Jul. 15, 2019.
EP1781068003 Extended European Search Report dated Dec. 11, 2019.
EP17869145.7 Supplementary European Search Report dated May 4, 2020.
EP18750938.5 Supplementary European Search Report dated Oct. 16, 2020.
European Patent Application No. 16835913.1 Communication pursuant to Article 94(3) dated Feb. 28, 2022.
Gillberg, C et al. Early Detection of Autism. Diagnostic Instruments for Clinicians. European Child & Adolescent Psychiatry vol. 5,2: pp. 67-74 (1996).
Great Britain Patent Application No. 1912672.1 First Exam Report dated Feb. 4, 2022.
Hamidpour, Rafie et al. Antipurinergic Therapy With Suramin as Treatment for Autism Spectrum Disorder. Journal of Biomedical sciences vol. 5,2: pp. 1-7 (2016).
Hirsch, Sybil et al. Development of a Questionnaire Weighted Scoring System to Target Diagnostic Examinations for Asthma in Adults: A Modelling Study. BMC Family Practice vol. 5,1: pp. 1-13 (2004).
Japanese Patent Application No. 2018-5231518 Office Action dated Jun. 21, 2021.
Japanese Patent Application No. 2018-531518 Notice of Reasons for Refusal dated Dec. 1, 2020.
Japanese Patent Application No. 2018-531518 Office Action dated Jun. 17, 2021.
Japanese Patent Application No. 2019-547219 Office Action dated Nov. 22, 2021.
Japanese Patent Application No. 2019-543082 Notice of Reasons for Refusal dated Feb. 22, 2022.
Muangnak, Nittaya et al. Classification Students with Learning Disabilities Using Naive Bayes Classifier and Decision Tree. The 6th International Conference on Networked Computing and Advanced Information Management IEEE : pp. 189-192 (2010).
Ogden, Adam et al. Suramin as a Chemosensitizer: Oral Pharmacokinetics in Rats. Pharmaceutical Research vol. 21,11: pp. 2058-2063 (2004).
Ordonez, C et al. Machine Learning Techniques Applied to the Determination of Osteoporosis Incidence in Post-menopausal Women. Mathematical and Computer Modelling vol. 50: pp. 673-679 (2009).
PCT/US2012/061422 International Search Report and Written Opinion dated May 24, 2013.
PCT/US2016/046557 International Search Report and Written Opinion dated Nov. 3, 2016.
PCT/US2016/067358 International Preliminary Report on Patentability dated Jun. 28, 2018.
PCT/US2018/017354 International Preliminary Report on Patentability dated Aug. 13, 2019.
PCT/US2018/017354 International Search Report and Written Opinion dated Apr. 26, 2018.
PCT/US2020/024029 International Search Report and Written Opinion dated Jul. 30, 2020.
PCT/US2020/049492 International Preliminary Report on Patentability dated Mar. 8, 2022.
PCT/US2020/053611 International Preliminary Report on Patentability dated Apr. 5, 2022.
PCT/US2020/053611 International Search Report and Written Opinion dated Dec. 21, 2020.
Rosipal, et al. Overview and Recent Advances in Partial Least Squares. Lecture Notes in Computer Science book series(LNTCS). vol. 3940 (2005): 18 pages.
Rutter, Michael et al. Autism Diagnostic Interview-revised. Western Psychological Services vol. 29,30: pp. 1-12 (2003).
Skuse, David et al. The Developmental, Dimensional and Diagnostic Interview (3di): a Novel Computerized Assessment for Autism Spectrum Disorders. Journal of the American Academy of Child and Adolescent Psychiatry vol. 43,5: pp. 548-558 (2004).
U.S. Appl. No. 16/155,758 Final Office Action dated Aug. 30, 2022.
U.S. Appl. No. 16/155,758 Non-Final Office Action dated Dec. 20, 2021.
U.S. Appl. No. 14/354,032 Notice of Allowance dated Apr. 13, 2016.
U.S. Appl. No. 14/354,032 Notice of Allowance dated Jun. 14, 2016.
U.S. Appl. No. 14/354,032 Office Action dated Jul. 28, 2015.
U.S. Appl. No. 15/234,814 Office Action dated Jan. 18, 2019.
U.S. Appl. No. 15/234,814 Office Action dated Jun. 7, 2018.
U.S. Appl. No. 15/234,814 Office Action dated Mar. 24, 2020.
U.S. Appl. No. 15/234,814 Office Action dated Oct. 3, 2019.
U.S. Appl. No. 15/589,877 Office Action dated Jan. 17, 2020.
U.S. Appl. No. 16/010,284 Office Action dated Aug. 5, 2021.
U.S. Appl. No. 16/010,284 Office Action dated Feb. 4, 2021.
U.S. Appl. No. 16/155,758 Office Action dated Jan. 12, 2021.
U.S. Appl. No. 16/155,758 Office Action dated Jul. 7, 2020.
U.S. Appl. No. 16/155,758 Office Action dated May 30, 2024.
U.S. Appl. No. 16/155,758 Preinterview First Office Action dated Feb. 8, 2019.
U.S. Appl. No. 16/155,761 Preinterview First Office Action dated Jan. 9, 2019.
U.S. Appl. No. 16/155,798 Office Action dated Apr. 9, 2020.
U.S. Appl. No. 16/155,798 Office Action dated Jul. 29, 2019.
U.S. Appl. No. 16/157,787 Office Action dated Mar. 27, 2019.
U.S. Appl. No. 17/088,428 Office Action dated May 25, 2021.
U.S. Appl. No. 17/088,428 Restriction Requirement dated Mar. 18, 2021.
U.S. Appl. No. 17/180,473 Office Action dated Apr. 19, 2021.
U.S. Appl. No. 17/180,473 Office Action dated Oct. 26, 2021.
U.S. Appl. No. 17/690,977 Notice of Allowance dated Feb. 7, 2024.

\* cited by examiner

METHODS AND APPARATUS FOR EVALUATING DEVELOPMENTAL CONDITIONS AND PROVIDING CONTROL OVER COVERAGE AND RELIABILITY

CROSS-REFERENCE

The present application is a continuation of U.S. application Ser. No. 16/155,794, filed Oct. 9, 2018, which is a continuation of International Patent Application No. PCT/US2017/061552, filed Nov. 14, 2017, which claims priority to U.S. Provisional Application No. 62/421,958, filed on Nov. 14, 2016, and U.S. Provisional Application No. 62/452,908, filed on Jan. 31, 2017, each of which applications are herein incorporated in their entireties for all purposes.

The subject matter of the present application is related to U.S. application Ser. No. 14/354,032, filed on Apr. 24, 2014, now U.S. Pat. No. 9,443,205, and U.S. application Ser. No. 15/234,814, filed on Aug. 11, 2016, the entire disclosures of which are incorporated herein by reference.

BACKGROUND OF THE INVENTION

Prior methods and apparatus for diagnosing and treating cognitive function attributes of people such as, for example, people with a developmental condition or disorder can be less than ideal in at least some respects. Unfortunately, a less than ideal amount of time, energy and money can be required to obtain a diagnosis and treatment, and to determine whether a subject is at risk for decreased cognitive function such as, dementia, Alzheimer's or a developmental disorder. Examples of cognitive and developmental disorders less than ideally treated by the prior approaches include autism, autistic spectrum, attention deficit disorder, attention deficit hyperactive disorder and speech and learning disability, for example. Examples of mood and mental illness disorders less than ideally treated by the prior approaches include depression, anxiety, ADHD, obsessive compulsive disorder, and substance disorders such as substance abuse and eating disorders. The prior approaches to diagnosis and treatment of several neurodegenerative diseases can be less than ideal in many instances, and examples of such neurodegenerative diseases include age related cognitive decline, cognitive impairment, Alzheimer's disease, Parkinson's disease, Huntington's disease, and amyotrophic lateral sclerosis ("ALS"), for example. The healthcare system is under increasing pressure to deliver care at lower costs, and prior methods and apparatus for clinically diagnosing or identifying a subject as at risk of a developmental disorder can result in greater expense and burden on the health care system than would be ideal. Further, at least some subjects are not treated as soon as ideally would occur, such that the burden on the healthcare system is increased with the additional care required for these subjects.

The identification and treatment of cognitive function attributes, including for example, developmental disorders in subjects can present a daunting technical problem in terms of both accuracy and efficiency. Many known methods for identifying such attributes or disorders are often time-consuming and resource-intensive, requiring a subject to answer a large number of questions or undergo extensive observation under the administration of qualified clinicians, who may be limited in number and availability depending on the subject's geographical location. In addition, many known methods for identifying and treating behavioral, neurological, or mental health conditions or disorders have less than ideal accuracy and consistency, as subjects to be evaluated using such methods often present a vast range of variation that can be difficult to capture and classify. A technical solution to such a technical problem would be desirable, wherein the technical solution can improve both the accuracy and efficiency of existing methods. Ideally, such a technical solution would reduce the required time and resources for administering a method for identifying and treating attributes of cognitive function, such as behavioral, neurological or mental health conditions or disorders, and improve the accuracy and consistency of the identification outcomes across subjects.

Although prior lengthy tests with questions can be administered to caretakers such as parents in order to diagnose or identify a subject as at risk for a developmental condition or disorder, such tests can be quite long and burdensome. For example at least some of these tests have over one hundred questions, and more than one such lengthy test may be administered further increasing the burden on health care providers and caretakers. Additional data may be required such as clinical observation of the subject, and clinical visits may further increase the amount of time and burden on the healthcare system. Consequently, the time between a subject being identified as needing to be evaluated and being clinically identified as at risk or diagnosed with a developmental delay can be several months, and in some instances over a year.

The delay between identified need for an evaluation and clinical diagnosis can result in less than ideal care in at least some instances. Some developmental disorders can be treated with timely intervention. However, the large gap between a caretaker initially identifying a prospective as needing an evaluation and clinically diagnosing the subject or clinically identifying the subject as at risk can result in less than ideal treatment. In at least some instances, a developmental disorder may have a treatment window, and the treatment window may be missed or the subject treated for only a portion of the treatment window.

Although prior methods and apparatus have been proposed to decrease the number of questions asked, such prior methods and apparatus can be less than ideal in at least some respects. Although prior methods and apparatus have relied on training and test datasets to train and validate, respectively, the methods and apparatus, the actual clinical results of such methods and apparatus can be less than ideal, as the clinical environment can present more challenging cases than the training and test dataset. The clinical environment can present subjects who may have one or more of several possible developmental disorders, and relying on a subset of questions may result in less than ideal sensitivity and specificity of the tested developmental disorder. Also, the use of only one test to diagnose only one developmental disorder, e.g. autism, may provide less than ideal results for diagnosing the intended developmental disorder and other disorders, as subject behavior from other developmental disorders may present confounding variables that decrease the sensitivity and specificity of the subset of questions targeting the one developmental disorder. Also, reliance on a predetermined subset can result in less than ideal results as more questions than would be ideal may be asked, and the questions asked may not be the ideal subset of questions for a particular subject.

Further, many subjects may have two or more related disorders or conditions. If each test is designed to diagnose or identify only a single disorder or condition, a subject presenting with multiple disorders may be required to take multiple tests. The evaluation of a subject using multiple diagnostic tests may be lengthy, expensive, inconvenient, and logistically challenging to arrange. It would be desirable to provide a way to test a subject using a single diagnostic test that is capable of identifying or diagnosing multiple related disorders or conditions with sufficient sensitivity and specificity.

Additionally, it would be helpful if diagnostic methods and treatments could be applied to subjects to advance cognitive function for subjects with advanced, normal and decreased cognitive function. In light of the above, improved methods and systems of diagnosing and identifying subjects at risk for a particular cognitive function attribute such as a developmental disorder and for providing improved digital therapeutics are needed. Ideally such methods and apparatus would require fewer questions, decreased amounts of time, determine a plurality of cognitive function attributes, such as behavioral, neurological or mental health conditions or disorders, and provide clinically acceptable sensitivity and specificity in a clinical or nonclinical environment, which can be used to monitor and adapt treatment efficacy. Moreover, improved digital therapeutics can provide a customized treatment plan for a patient, receive updated diagnostic data in response to the customized treatment plan to determine progress, and update the treatment plan accordingly. Ideally, such methods and apparatus can also be used to determine the developmental progress of a subject, and offer treatment to advance developmental progress.

SUMMARY OF THE INVENTION

The methods and apparatus disclosed herein can determine a cognitive function attribute such as the developmental progress of a subject in a clinical or nonclinical environment. For example, the described methods and apparatus can identify a subject as developmentally advanced in one or more areas of development, or identify a subject as developmentally delayed or at risk of having one or more developmental disorders. The methods and apparatus disclosed can determine the subject's developmental progress by evaluating a plurality of characteristics or features of the subject based on an assessment model, wherein the assessment model can be generated from large datasets of relevant subject populations using machine-learning approaches. The methods and apparatus disclosed herein comprise improved logical structures and processes to diagnose a subject with a disorder among a plurality of disorders, using a single test.

The methods and apparatus disclosed herein can diagnose or identify a subject as at risk of having one or more cognitive function attributes such as for example, a subject at risk of having one or more developmental disorders among a plurality of developmental disorders in a clinical or nonclinical setting, with fewer questions, in a decreased amounts of time, and with clinically acceptable sensitivity and specificity in a clinical environment. A processor can be configured with instructions to identify a most predictive next question, such that a person can be diagnosed or identified as at risk with fewer questions. Identifying the most predictive next question in response to a plurality of answers has the advantage of increasing the sensitivity and the specificity with fewer questions. The methods and apparatus disclosed herein can be configured to evaluate a subject for a plurality of related developmental disorders using a single test, and diagnose or determine the subject as at risk of one or more of the plurality of developmental disorders using the single test. Decreasing the number of questions presented can be particularly helpful where a subject presents with a plurality of possible developmental disorders.

Evaluating the subject for the plurality of possible disorders using just a single test can greatly reduce the length and cost of the evaluation procedure. The methods and apparatus disclosed herein can diagnose or identify the subject as at risk for having a single developmental disorder among a plurality of possible developmental disorders that may have overlapping symptoms.

While the most predictive next question can be determined in many ways, in many instances the most predictive next question is determined in response to a plurality of answers to preceding questions that may comprise prior most predictive next questions. The most predictive next question can be determined statistically, and a set of possible most predictive next questions evaluated to determine the most predictive next question. In many instances, answers to each of the possible most predictive next questions are related to the relevance of the question, and the relevance of the question can be determined in response to the combined feature importance of each possible answer to a question.

The methods and apparatus disclosed herein can categorize a subject into one of three categories: having one or more developmental conditions, being developmentally normal or typical, or inconclusive (i.e. requiring additional evaluation to determine whether the subject has any developmental conditions). A developmental condition can be a developmental disorder or a developmental advancement. Note that the methods and apparatus disclosed herein are not limited to developmental conditions, and may be applied to other cognitive function attributes, such as behavioral, neurological or mental health conditions. The methods and apparatus may initially categorize a subject into one of the three categories, and subsequently continue with the evaluation of a subject initially categorized as "inconclusive" by collecting additional information from the subject. Such continued evaluation of a subject initially categorized as "inconclusive" may be performed continuously with a single screening procedure (e.g., containing various assessment modules). Alternatively or additionally, a subject identified as belonging to the inconclusive group may be evaluated using separate, additional screening procedures and/or referred to a clinician for further evaluation.

The methods and apparatus disclosed herein can evaluate a subject using a combination of questionnaires and video inputs, wherein the two inputs may be integrated mathematically to optimize the sensitivity and/or specificity of classification or diagnosis of the subject. Optionally, the methods and apparatus can be optimized for different settings (e.g., primary vs secondary care) to account for differences in expected prevalence rates depending on the application setting.

The methods and apparatus disclosed herein can account for different subject-specific dimensions such as, for example, a subject's age, a geographic location associated with a subject, a subject's gender or any other subject-specific or demographic data associated with a subject. In particular, the methods and apparatus disclosed herein can take different subject-specific dimensions into account in identifying the subject as at risk of having one or more cognitive function attributes such as developmental conditions, in order to increase the sensitivity and specificity of evaluation, diagnosis, or classification of the subject. For example, subjects belonging to different age groups may be evaluated using different machine learning assessment models, each of which can be specifically tuned to identify the one or more developmental conditions in subjects of a particular age group. Each age group-specific assessment model may contain a unique group of assessment items (e.g., questions, video observations), wherein some of the assessment items may overlap with those of other age groups' specific assessment models.

In addition, the digital personalized medicine systems and methods described herein can provide digital diagnostics and digital therapeutics to patients. The digital personalized medicine system can use digital data to assess or diagnose symptoms of a patient in ways that inform personalized or more appropriate therapeutic interventions and improved diagnoses.

In one aspect, the digital personalized medicine system can comprise digital devices with processors and associated software that can be configured to: use data to assess and diagnose a patient; capture interaction and feedback data that identify relative levels of efficacy, compliance and response resulting from the therapeutic interventions; and perform data analysis. Such data analysis can include artificial intelligence, including for example machine learning, and/or statistical models to assess user data and user profiles to further personalize, improve or assess efficacy of the therapeutic interventions.

In some instances, the system can be configured to use digital diagnostics and digital therapeutics. Digital diagnostics and digital therapeutics can comprise a system or methods for digitally collecting information and processing and evaluating the provided data to improve the medical, psychological, or physiological state of an individual. A digital therapeutic system can apply software based learning to evaluate user data, monitor and improve the diagnoses and therapeutic interventions provided by the system.

Digital diagnostics data in the system can comprise data and meta-data collected from the patient, or a caregiver, or a party that is independent of the assessed individual. In some instances, the collected data can comprise monitoring behaviors, observations, judgments, or assessments made by a party other than the individual. In further instances, the assessment can comprise an adult performing an assessment or provide data for an assessment of a child or juvenile. The data and meta-data can be either actively or passively collected in digital format via one or more digital devices such as mobile phones, video capture, audio capture, activity monitors, or wearable digital monitors.

The digital diagnostic uses the data collected by the system about the patient, which can include complimentary diagnostic data captured outside the digital diagnostic, with analysis from tools such as machine learning, artificial intelligence, and statistical modeling to assess or diagnose the patient's condition. The digital diagnostic can also provide an assessment of a patient's change in state or performance, directly or indirectly via data and meta-data that can be analyzed and evaluated by tools such as machine learning, artificial intelligence, and statistical modeling to provide feedback into the system to improve or refine the diagnoses and potential therapeutic interventions.

Data assessment and machine learning from the digital diagnostic and corresponding responses, or lack thereof, from the therapeutic interventions can lead to the identification of novel diagnoses for patients and novel therapeutic regimens for both patents and caregivers.

Types of data collected and utilized by the system can include patient and caregiver video, audio, responses to questions or activities, and active or passive data streams from user interaction with activities, games or software features of the system, for example. Such data can also include meta-data from patient or caregiver interaction with the system, for example, when performing recommended activities. Specific meta-data examples include data from a user's interaction with the system's device or mobile app that captures aspects of the user's behaviors, profile, activities, interactions with the software system, interactions with games, frequency of use, session time, options or features selected, and content and activity preferences. Data can also include data and meta-data from various third party devices such as activity monitors, games or interactive content.

Digital therapeutics can comprise instructions, feedback, activities or interactions provided to the patient or caregiver by the system. Examples include suggested behaviors, activities, games or interactive sessions with system software and/or third party devices.

In further aspects, the digital therapeutics methods and systems disclosed herein can diagnose and treat a subject at risk of having one or more behavioral, neurological or mental health conditions or disorders among a plurality of behavioral, neurological or mental health conditions or disorders in a clinical or nonclinical setting. This diagnosis and treatment can be accomplished using the methods and systems disclosed herein with fewer questions, in a decreased amount of time, and with clinically acceptable sensitivity and specificity in a clinical environment, and can provide treatment recommendations. This can be helpful when a subject initiates treatment based on an incorrect diagnosis, for example. A processor can be configured with instructions to identify a most predictive next question or most instructive next symptom or observation such that a person can be diagnosed or identified as at risk reliably using only the optimal number of questions or observations. Identifying the most predictive next question or most instructive next symptom or observation in response to a plurality of answers has the advantage of providing treatment with fewer questions without degrading the sensitivity or specificity of the diagnostic process. In some instances, an additional processor can be provided to predict or collect information on the next more relevant symptom. The methods and apparatus disclosed herein can be configured to evaluate and treat a subject for a plurality of related disorders using a single adaptive test, and diagnose or determine the subject as at risk of one or more of the plurality of disorders using the single test. Decreasing the number of questions presented or symptoms or measurements used can be particularly helpful where a subject presents with a plurality of possible disorders that can be treated. Evaluating the subject for the plurality of possible disorders using just a single adaptive test can greatly reduce the length and cost of the evaluation procedure and improve treatment. The methods and apparatus disclosed herein can diagnose and treat subject at risk for having a single disorder among a plurality of possible disorders that may have overlapping symptoms.

The most predictive next question, most instructive next symptom or observation used for the digital therapeutic treatment can be determined in many ways. In many instances, the most predictive next question, symptom, or observation can be determined in response to a plurality of answers to preceding questions or observation that may comprise prior most predictive next question, symptom, or observation to evaluate the treatment and provide a closed-loop assessment of the subject. The most predictive next question, symptom, or observation can be determined statistically, and a set of candidates can be evaluated to determine the most predictive next question, symptom, or observation. In many instances, observations or answers to each of the candidates are related to the relevance of the question or observation, and the relevance of the question or observation can be determined in response to the combined feature importance of each possible answer to a question or observation. Once a treatment has been initiated, the questions, symptoms, or observations can be repeated or different questions, symptoms, or observations can be used to more accurately monitor progress and suggest changes to the digital treatment. The relevance of a next question, symptom or observation can also depend on the variance of the ultimate assessment among different answer choices of the question or potential options for an observation. For example, a question for which the answer choices might have a significant impact on the ultimate assessment down the line can be deemed more relevant than a question for which the answer choices might only help to discern differences in severity for one particular condition, or are otherwise less consequential.

In one aspect, a method of providing an evaluation of at least one cognitive function attribute of a subject may comprise: on a computer system having a processor and a memory storing a computer program for execution by the processor, the computer program comprising instructions for: receiving data of the subject related to the cognitive function attribute; evaluating the data of the subject using a machine learning model; and providing an evaluation for the subject, the evaluation selected from the group consisting of an inconclusive determination and a categorical determination in response to the data. The machine learning model may comprise a selected subset of a plurality of machine learning assessment models.

The categorical determination may comprise a presence of the cognitive function attribute and an absence of the cognitive function attribute. Receiving data from the subject may comprise receiving an initial set of data. Evaluating the data from the subject may comprise evaluating the initial set of data using a preliminary subset of tunable machine learning assessment models selected from the plurality of tunable machine learning assessment models to output a numerical score for each of the preliminary subset of tunable machine learning assessment models.

The method may further comprise providing a categorical determination or an inconclusive determination as to the presence or absence of the cognitive function attribute in the subject based on the analysis of the initial set of data, wherein the ratio of inconclusive to categorical determinations can be adjusted. The method may further comprise: determining whether to apply additional assessment models selected from the plurality of tunable machine learning assessment models if the analysis of the initial set of data yields an inconclusive determination; receiving an additional set of data from the subject based on an outcome of the decision; evaluating the additional set of data from the subject using the additional assessment models to output a numerical score for each of the additional assessment models based on the outcome of the decision; and providing a categorical determination or an inconclusive determination as to the presence or absence of the cognitive function attribute in the subject based on the analysis of the additional set of data from the subject using the additional assessment models, wherein the ratio of inconclusive to categorical determinations can be adjusted.

The method may further comprise: combining the numerical scores for each of the preliminary subset of assessment models to generate a combined preliminary output score; and mapping the combined preliminary output score to a categorical determination or to an inconclusive determination as to the presence or absence of the cognitive function attribute in the subject, wherein the ratio of inconclusive to categorical determinations can be adjusted.

The method may further comprise employing rule-based logic or combinatorial techniques for combining the numerical scores for each of the preliminary subset of assessment models and for combining the numerical scores for each of the additional assessment models. The ratio of inconclusive to categorical determinations may be adjusted by specifying an inclusion rate. The categorical determination as to the presence or absence of the developmental condition in the subject may be assessed by providing a sensitivity and specificity metric. The inclusion rate may be no less than 70% and the categorical determination may result in a sensitivity of at least 70 with a corresponding specificity of at least 70. The inclusion rate may be no less than 70% and the categorical determination may result in a sensitivity of at least 80 with a corresponding specificity of at least 80. The inclusion rate may be no less than 70% and the categorical determination may result in a sensitivity of at least 90 with a corresponding specificity of at least 90.

Data from the subject may comprise at least one of a sample of a diagnostic instrument, wherein the diagnostic instrument comprises a set of diagnostic questions and corresponding selectable answers, and demographic data.

The method may further comprise: training a plurality of tunable machine learning assessment models using data from a plurality of subjects previously evaluated for the developmental condition, wherein training comprises: pre-processing the data from the plurality of subjects using machine learning techniques; extracting and encoding machine learning features from the pre-processed data; processing the data from the plurality of subjects to mirror an expected prevalence of a cognitive function attribute among subjects in an intended application setting; selecting a subset of the processed machine learning features; evaluating each model in the plurality of tunable machine learning assessment models for performance, wherein each model is evaluated for sensitivity and specificity for a pre-determined inclusion rate; and determining an optimal set of parameters for each model based on determining the benefit of using all models in a selected subset of the plurality of tunable machine learning assessment models. Determining an optimal set of parameters for each model may comprise tuning the parameters of each model under different tuning parameter settings.

Processing the encoded machine learning features may comprise: computing and assigning sample weights to every sample of data, wherein each sample of data corresponds to a subject in the plurality of subjects, wherein samples are grouped according to subject-specific dimensions, and wherein the sample weights are computed and assigned to balance one group of samples against every other group of samples to mirror the expected distribution of each dimension among subjects in an intended setting. The subject-specific dimensions may comprise a subject's gender, the geographic region where a subject resides, and a subject's age. Extracting and encoding machine learning features from the pre-processed data may comprise using feature encoding techniques such as but not limited to one-hot encoding, severity encoding, and presence-of-behavior encoding. Selecting a subset of the processed machine learning features may comprise using bootstrapping techniques to identify a subset of discriminating features from the processed machine learning features.

The cognitive function attribute may comprise a behavioral disorder and a developmental advancement. The categorical determination provided for the subject may be selected from the group consisting of an inconclusive determination, a presence of multiple cognitive function attributes, and an absence of multiple cognitive function attributes in response to the data.

In another aspect, an apparatus to evaluate a cognitive function attribute of a subject may comprise processor configured with instructions that, when executed, cause the processor to perform the method described above.

In another aspect, a mobile device for providing an evaluation of at least one cognitive function attribute of a subject may comprise: a display; and a processor configured with instructions to: receive and display data of the subject related to the cognitive function attribute; and receive and display an evaluation for the subject, the evaluation selected from the group consisting of an inconclusive determination and a categorical determination; wherein the evaluation for the subject has been determined in response to the data of the subject.

The categorical determination may be selected from the group consisting of a presence of the cognitive function attribute, and an absence of the cognitive function attribute. The cognitive function attribute may be determined with a sensitivity of at least 80 and a specificity of at least 80, respectively, for the presence or the absence of the cognitive function attribute. The cognitive function attribute may be determined with a sensitivity of at least 90 and a specificity of at least 90, respectively, for the presence or the absence of the cognitive function attribute. The cognitive function attribute may comprise a behavioral disorder and a developmental advancement.

In another aspect, digital therapeutic system to treat a subject with a personal therapeutic treatment plan may comprise: one or more processors comprising software instructions; a diagnostic module to receive data from the subject and output diagnostic data for the subject, the diagnostic module comprising one or more classifiers built using machine learning or statistical modeling based on a subject population to determine the diagnostic data for the subject, and wherein the diagnostic data comprises an evaluation for the subject, the evaluation selected from the group consisting of an inconclusive determination and a categorical determination in response to data received from the subject; and a therapeutic module to receive the diagnostic data and output the personal therapeutic treatment plan for the subject, the therapeutic module comprising one or more models built using machine learning or statistical modeling based on at least a portion the subject population to determine and output the personal therapeutic treatment plan of the subject, wherein the diagnostic module is configured to receive updated subject data from the subject in response to therapy of the subject and generate updated diagnostic data from the subject and wherein the therapeutic module is configured to receive the updated diagnostic data and output an updated personal treatment plan for the subject in response to the diagnostic data and the updated diagnostic data.

The diagnostic module may comprise a diagnostic machine learning classifier trained on the subject population and the therapeutic module may comprise a therapeutic machine learning classifier trained on the at least the portion of the subject population and the diagnostic module and the therapeutic module may be arranged for the diagnostic module to provide feedback to the therapeutic module based on performance of the treatment plan. The therapeutic classifier may comprise instructions trained on a data set comprising a population of which the subject is not a member and the subject may comprise a person who is not a member of the population. The diagnostic module may comprise a diagnostic classifier trained on plurality of profiles of a subject population of at least 10,000 people and therapeutic profile trained on the plurality of profiles of the subject population.

In another aspect, a system to evaluate of at least one cognitive function attribute of a subject may comprise: a processor configured with instructions that when executed cause the processor to: present a plurality of questions from a plurality of chains of classifiers, the plurality of chains of classifiers comprising a first chain comprising a social/behavioral delay classifier and a second chain comprising a speech & language delay classifier. The social/behavioral delay classifier may be operatively coupled to an autism & ADHD classifier. The social/behavioral delay classifier may be configured to output a positive result if the subject has a social/behavioral delay and a negative result if the subject does not have the social/behavioral delay. The social/behavioral delay classifier may be configured to output an inconclusive result if it cannot be determined with a specified sensitivity and specificity whether or not the subject has the social/behavioral delay. The social/behavioral delay classifier output may be coupled to an input of an Autism and ADHD classifier and the Autism and ADHD classifier may be configured to output a positive result if the subject has Autism or ADHD. The output of the Autism and ADHD classifier may be coupled to an input of an Autism v. ADHD classifier, and the Autism v. ADHD classifier may be configured to generate a first output if the subject has autism and a second output if the subject has ADHD. The Autism v. ADHD classifier may be configured to provide an inconclusive output if it cannot be determined with specified sensitivity and specificity whether or not the subject has autism or ADHD. The speech & language delay classifier may be operatively coupled to an intellectual disability classifier. The speech & language delay classifier may be configured to output a positive result if the subject has a speech and language delay and a negative output if the subject does not have the speech and language delay. The speech & language delay classifier may be configured to output an inconclusive result if it cannot be determined with a specified sensitivity and specificity whether or not the subject has the speech and language delay. The speech & language delay classifier output may be coupled to an input of an intellectual disability classifier and the intellectual disability classifier may be configured to generate a first output if the subject has intellectual disability and a second output if the subject has the speech and language delay but no intellectual disability. The intellectual disability classifier may be configured to provide an inconclusive output if it cannot be determined with a specified sensitivity and specificity whether or not the subject has the intellectual disability.

The processor may be configured with instructions to present questions for each chain in sequence and skip overlapping questions. The first chain may comprise the social/behavioral delay classifier coupled to an autism & ADHD classifier. The second chain may comprise the speech & language delay classifier coupled to an intellectual disability classifier. A user may go through the first chain and the second chain in sequence.

In another aspect, a method for administering a drug to a subject may comprise: detecting a neurological disorder of the subject with a machine learning classifier; and administering the drug to the subject in response to the detected neurological disorder. The neurological disorder may comprise autism spectrum disorder, and the drug may be selected from the group consisting of risperidone, quetiapine, amphetamine, dextroamphetamine, methylphenidate, methamphetamine, dextroamphetamine, dexmethylphenidate, guanfacine, atomoxetine, lisdexamfetamine, clonidine, and aripiprazolecomprise; or the neurological disorder may comprise attention deficit disorder (ADD), and the drug may be selected from the group consisting of amphetamine, dextroamphetamine, methylphenidate, methamphetamine, dextroamphetamine, dexmethylphenidate, guanfacine, atomoxetine, lisdexamfetamine, clonidine, and modafinil; or the neurological disorder may comprise attention deficit hyperactivity disorder (ADHD), and the drug may be selected from the group consisting of amphetamine, dextroamphetamine, methylphenidate, methamphetamine, dextroamphetamine, dexmethylphenidate, guanfacine, atomoxetine, lisdexamfetamine, clonidine, and modafinil; or the neurological disorder may comprise obsessive-compulsive disorder, and the drug may be selected from the group consisting of buspirone, sertraline, escitalopram, citalopram, fluoxetine, paroxetine, venlafaxine, clomipramine, and fluvoxamine; or the neurological disorder may comprise acute stress disorder, and the drug may be selected from the group consisting of propranolol, citalopram, escitalopram, sertraline, paroxetine, fluoextine, venlafaxine, mirtazapine, nefazodone, carbamazepine, divalproex, lamotrigine, topiramate, prazosin, phenelzine, imipramine, diazepam, clonazepam, lorazepam, and alprazolam; or the neurological disorder may comprise adjustment disorder, and the drug may be selected from the group consisting of busiprone, escitalopram, sertraline, paroxetine, fluoextine, diazepam, clonazepam, lorazepam, and alprazolam; or neurological disorder may comprise agoraphobia, and the drug may be selected from the group consisting of diazepam, clonazepam, lorazepam, alprazolam, citalopram, escitalopram, sertraline, paroxetine, fluoextine, and busiprone; or the neurological disorder may comprise Alzheimer's disease, and the drug may be selected from the group consisting of donepezil, galantamine, memantine, and rivastigmine; or the neurological disorder may comprise anorexia nervosa, and the drug may be selected from the group consisting of olanzapine, citalopram, escitalopram, sertraline, paroxetine, and fluoxetine; or the neurological disorder may comprise anxiety disorders, and the drug may be selected from the group consisting of sertraline, escitalopram, citalopram, fluoxetine, diazepam, buspirone, venlafaxine, duloxetine, imipramine, desipramine, clomipramine, lorazepam, clonazepam, and pregabalin; or the neurological disorder may comprise bereavement, and the drug may be selected from the group consisting of citalopram, duloxetine, and doxepin; or the neurological disorder may comprise binge eating disorder, and the drug may be selected from the group consisting of lisdexamfetamine; or the neurological disorder may comprise bipolar disorder, and the drug may be selected from the group consisting of topiramate, lamotrigine, oxcarbazepine, haloperidol, risperidone, quetiapine, olanzapine, aripiprazole, and fluoxetine; or the neurological disorder may comprise body dysmorphic disorder, and the drug may be selected from the group consisting of sertraline, escitalopram, and citalopram; or the neurological disorder may comprise brief psychotic disorder, and the drug may be selected from the group consisting of clozapine, asenapine, olanzapine, and quetiapine; or the neurological disorder may comprise bulimia nervosa, and the drug may be selected from the group consisting of sertraline and fluoxetine; or the neurological disorder may comprise conduct disorder, and the drug may be selected from the group consisting of lorazepam, diazepam, and clobazam; or the neurological disorder may comprise delusional disorder, and the drug may be selected from the group consisting of clozapine, asenapine, risperidone, venlafaxine, bupropion, and buspirone; the neurological disorder may comprise depersonalization disorder, and the drug may be selected from the group consisting of sertraline, fluoxetine, alprazolam, diazepam, and citalopram; or the neurological disorder may comprise depression, and the drug may be selected from the group consisting of sertraline, fluoxetine, citalopram, bupropion, escitalopram, venlafaxine, aripiprazole, buspirone, vortioxetine, and vilazodone; or the neurological disorder may comprise disruptive mood dysregulation disorder, and the drug may be selected from the group consisting of quetiapine, clozapine, asenapine, and pimavanserin; or the neurological disorder may comprise dissociative amnesia, and the drug may be selected from the group consisting of alprazolam, diazepam, lorazepam, and chlordiazepoxide; or the neurological disorder may comprise dissociative disorder, and the drug may be selected from the group consisting of bupropion, vortioxetine, and vilazodone; or the neurological disorder may comprise dissociative fugue, and the drug may be selected from the group consisting of amobarbital, aprobarbital, butabarbital, and methohexitlal; or the neurological disorder may comprise dysthymic disorder, and the drug may be selected from the group consisting of bupropion, venlafaxine, sertraline, and citalopram; the neurological disorder may comprise eating disorders, and the drug may be selected from the group consisting of olanzapine, citalopram, escitalopram, sertraline, paroxetine, and fluoxetine; or the neurological disorder may comprise gender dysphoria, and the drug may be selected from the group consisting of estrogen, prostogen, and testosterone; or the neurological disorder may comprise generalized anxiety disorder, and the drug may be selected from the group consisting of venlafaxine, duloxetine, buspirone, sertraline, and fluoxetine; or the neurological disorder may comprise hoarding disorder, and the drug may be selected from the group consisting of buspirone, sertraline, escitalopram, citalopram, fluoxetine, paroxetine, venlafaxine, and clomipramine; or the neurological disorder may comprise intermittent explosive disorder, and the drug may be selected from the group consisting of asenapine, clozapine, olanzapine, and pimavanserin; or the neurological disorder may comprise kleptomania, and the drug may be selected from the group consisting of escitalopram, fluvoxamine, fluoxetine, and paroxetine; or the neurological disorder may comprise panic disorder, and the drug may be selected from the group consisting of bupropion, vilazodone, and vortioxetine; or the neurological disorder may comprise Parkinson's disease, and the drug may be selected from the group consisting of rivastigmine, selegiline, rasagiline, bromocriptine, amantadine, cabergoline, and benztropine; or the neurological disorder may comprise pathological gambling, and the drug may be selected from the group consisting of bupropion, vilazodone, and vartioxetine; or the neurological disorder may comprise postpartum depression, and the drug may be selected from the group consisting of sertraline, fluoxetine, citalopram, bupropion, escitalopram, venlafaxine, aripiprazole, buspirone, vortioxetine, and vilazodone; or the neurological disorder may comprise posttraumatic stress disorder, and the drug may be selected from the group consisting of sertraline, fluoxetine, and paroxetine; or the neurological disorder may comprise premenstrual dysphoric disorder, and the drug may be selected from the group consisting of estadiol, drospirenone, sertraline, citalopram, fluoxetine, and busiprone; or the neurological disorder may comprise pseudobulbar affect, and the drug may be selected from the group consisting of dextromethorphan hydrobromide, and quinidine sulfate; or the neurological disorder may comprise pyromania, and the drug may be selected from the group consisting of clozapine, asenapine, olanzapine, paliperidone, and quetiapine; or the neurological disorder may comprise schizoaffective disorder, and the drug may be selected from the group consisting of sertraline, carbamazepine, oxcarbazepine, valproate, haloperidol, olanzapine, and loxapine; or the neurological disorder may comprise schizophrenia, and the drug may be selected from the group consisting of chlopromazine, haloperidol, fluphenazine, risperidone, quetiapine, ziprasidone, olanzapine, perphenazine, aripiprazole, and prochlorperazine; or the neurological disorder may comprise schizophreniform disorder, and the drug may be selected from the group consisting of paliperidone, clozapine, and risperidone; or the neurological disorder may comprise seasonal affective disorder, and the drug may be selected from the group consisting of sertraline, and fluoxetine; or the neurological disorder may comprise shared psychotic disorder, and the drug may be selected from the group consisting of clozapine, pimavanserin, risperidone, and lurasidone; or the neurological disorder may comprise social anxiety phobia, and the drug may be selected from the group consisting of amitriptyline, bupropion, citalopram, fluoxetine, sertraline, and venlafaxine; or the neurological disorder may comprise specific phobia, and the drug may be selected from the group consisting of diazepam, estazolam, quazepam, and alprazolam; or the neurological disorder may comprise stereotypic movement disorder, and the drug may be selected from the group consisting of risperidone, and clozapine; or the neurological disorder may comprise Tourette's disorder, and the drug may be selected from the group consisting of haloperidol, fluphenazine, risperidone, ziprasidone, pimozide, perphenazine, and aripiprazole; or the neurological disorder may comprise transient tic disorder, and the drug may be selected from the group consisting of guanfacine, clonidine, pimozide, risperidone, citalopram, escitalopram, sertraline, paroxetine, and fluoxetine; or the neurological disorder may comprise trichotillomania, and the drug may be selected from the group consisting of sertraline, fluoxetine, paroxetine, desipramine, and clomipramine.

Amphetamine may be administered with a dosage of 5 mg to 50 mg. Dextroamphetamine may be administered with a dosage that is in a range of 5 mg to 60 mg. Methylphenidate may be administered with a dosage that is in a range of 5 mg to 60 mg. Methamphetamine may be administered with a dosage that is in a range of 5 mg to 25 mg. Dexmethylphenidate may be administered with a dosage that is in a range of 2.5 mg to 40 mg. Guanfacine may be administered with a dosage that is in a range of 1 mg to 10 mg. Atomoxetine may be administered with a dosage that is in a range of 10 mg to 100 mg. Lisdexamfetamine may be administered with a dosage that is in a range of 30 mg to 70 mg. Clonidine may be administered with a dosage that is in a range of 0.1 mg to 0.5 mg. Modafinil may be administered with a dosage that is in a range of 100 mg to 500 mg. Risperidone may be administered with a dosage that is in a range of 0.5 mg to 20 mg. Quetiapine may be administered with a dosage that is in a range of 25 mg to 1000 mg. Buspirone may be administered with a dosage that is in a range of 5 mg to 60 mg. Sertraline may be administered with a dosage of up to 200 mg. Escitalopram may be administered with a dosage of up to 40 mg. Citalopram may be administered with a dosage of up to 40 mg. Fluoxetine may be administered with a dosage that is in a range of 40 mg to 80 mg. Paroxetine may be administered with a dosage that is in a range of 40 mg to 60 mg. Venlafaxine may be administered with a dosage of up to 375 mg. Clomipramine may be administered with a dosage of up to 250 mg. Fluvoxamine may be administered with a dosage of up to 300 mg.

The machine learning classifier may have an inclusion rate of no less than 70%. The machine learning classifier may be capable of outputting an inconclusive result.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Figure 1A:
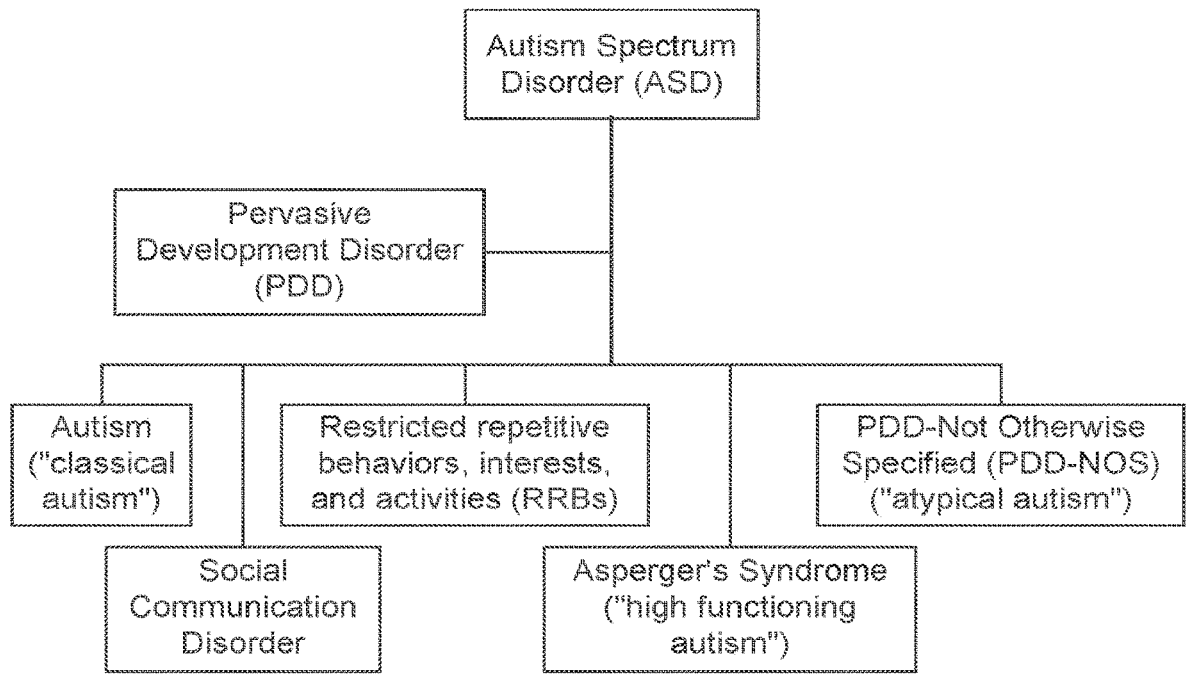
FIGS. 1A and 1B show some exemplary developmental disorders that may be evaluated using the assessment procedure as described herein.

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed. It shall be understood that different aspects of the invention can be appreciated individually, collectively, or in combination with each other.

The terms "based on" and "in response to" are used interchangeably with the present disclosure.

The term "processor" encompasses one or more of a local processor, a remote processor, or a processor system, and combinations thereof.

The term "feature" is used herein to describe a characteristic or attribute that is relevant to determining the developmental progress of a subject. For example, a "feature" may refer to a clinical characteristic that is relevant to clinical evaluation or diagnosis of a subject for one or more developmental disorders (e.g., age, ability of subject to engage in pretend play, etc.). The term "feature value" is herein used to describe a particular subject's value for the corresponding feature. For example, a "feature value" may refer to a clinical characteristic of a subject that is related to one or more developmental disorders (e.g., if feature is "age", feature value could be 3; if feature is "ability of subject to engage in pretend play", feature value could be "variety of pretend play" or "no pretend play").

As used herein, the phrases "autism" and "autism spectrum disorder" may be used interchangeably.

As used herein, the phrases "attention deficit disorder (ADD)" and "attention deficit/hyperactivity disorder (ADHD)" may be used interchangeably.

Described herein are methods and apparatus for determining the developmental progress of a subject. For example, the described methods and apparatus can identify a subject as developmentally advanced in one or more areas of development or cognitively declining in one or more cognitive functions, or identify a subject as developmentally delayed or at risk of having one or more developmental disorders. The methods and apparatus disclosed can determine the subject's developmental progress by evaluating a plurality of characteristics or features of the subject based on an assessment model, wherein the assessment model can be generated from large datasets of relevant subject populations using machine-learning approaches.

While methods and apparatus are herein described in the context of identifying one or more developmental disorders of a subject, the methods and apparatus are well-suited for use in determining any developmental progress of a subject. For example, the methods and apparatus can be used to identify a subject as developmentally advanced, by identifying one or more areas of development in which the subject is advanced. To identify one or more areas of advanced development, the methods and apparatus may be configured to assess one or more features or characteristics of the subject that are related to advanced or gifted behaviors, for example. The methods and apparatus as described can also be used to identify a subject as cognitively declining in one or more cognitive functions, by evaluating the one or more cognitive functions of the subject.

Described herein are methods and apparatus for diagnosing or assessing risk for one or more developmental disorders in a subject. The method may comprise providing a data processing module, which can be utilized to construct and administer an assessment procedure for screening a subject for one or more of a plurality of developmental disorders or conditions. The assessment procedure can evaluate a plurality of features or characteristics of the subject, wherein each feature can be related to the likelihood of the subject having at least one of the plurality of developmental disorders screenable by the procedure. Each feature may be related to the likelihood of the subject having two or more related developmental disorders, wherein the two or more related disorders may have one or more related symptoms. The features can be assessed in many ways. For example, the features may be assessed via a subject's answers to questions, observations of a subject, or results of a structured interaction with a subject, as described in further detail herein.

To distinguish among a plurality of developmental disorders of the subject within a single screening procedure, the procedure can dynamically select the features to be evaluated in the subject during administration of the procedure, based on the subject's values for previously presented features (e.g., answers to previous questions). The assessment procedure can be administered to a subject or a caretaker of the subject with a user interface provided by a computing device. The computing device comprises a processor having instructions stored thereon to allow the user to interact with the data processing module through a user interface. The assessment procedure may take less than 10 minutes to administer to the subject, for example 5 minutes or less. Thus, apparatus and methods described herein can provide a prediction of a subject's risk of having one or more of a plurality of developmental disorders using a single, relatively short screening procedure.

The methods and apparatus disclosed herein can be used to determine a most relevant next question related to a feature of a subject, based on previously identified features of the subject. For example, the methods and apparatus can be configured to determine a most relevant next question in response to previously answered questions related to the subject. A most predictive next question can be identified after each prior question is answered, and a sequence of most predictive next questions and a corresponding sequence of answers generated. The sequence of answers may comprise an answer profile of the subject, and the most predictive next question can be generated in response to the answer profile of the subject.

The methods and apparatus disclosed herein are well suited for combinations with prior questions that can be used to diagnose or identify the subject as at risk in response to fewer questions by identifying the most predictive next question in response to the previous answers, for example.

In one aspect, a method of providing an evaluation of at least one cognitive function attribute of a subject comprises the operations of: on a computer system having a processor and a memory storing a computer program for execution by the processor. The computer program may comprise instructions for: 1) receiving data of the subject related to the cognitive function attribute; 2) evaluating the data of the subject using a machine learning model; and 3) providing an evaluation for the subject. The evaluation may be selected from the group consisting of an inconclusive determination and a categorical determination in response to the data. The machine learning model may comprise a selected subset of a plurality of machine learning assessment models. The categorical determination may comprise a presence of the cognitive function attribute and an absence of the cognitive function attribute.

Receiving data from the subject may comprise receiving an initial set of data. Evaluating the data from the subject may comprise evaluating the initial set of data using a preliminary subset of tunable machine learning assessment models selected from the plurality of tunable machine learning assessment models to output a numerical score for each of the preliminary subset of tunable machine learning assessment models. The method may further comprise providing a categorical determination or an inconclusive determination as to the presence or absence of the cognitive function attribute in the subject based on the analysis of the initial set of data, wherein the ratio of inconclusive to categorical determinations can be adjusted.

The method may further comprise the operations of: 1) determining whether to apply additional assessment models selected from the plurality of tunable machine learning assessment models if the analysis of the initial set of data yields an inconclusive determination; 2) receiving an additional set of data from the subject based on an outcome of the decision; 3) evaluating the additional set of data from the subject using the additional assessment models to output a numerical score for each of the additional assessment models based on the outcome of the decision; and 4) providing a categorical determination or an inconclusive determination as to the presence or absence of the cognitive function attribute in the subject based on the analysis of the additional set of data from the subject using the additional assessment models. The ratio of inconclusive to categorical determinations may be adjusted.

The method may further comprise the operations: 1) combining the numerical scores for each of the preliminary subset of assessment models to generate a combined preliminary output score; and 2) mapping the combined preliminary output score to a categorical determination or to an inconclusive determination as to the presence or absence of the cognitive function attribute in the subject. The ratio of inconclusive to categorical determinations may be adjusted. The method may further comprise the operations of: 1) combining the numerical scores for each of the additional assessment models to generate a combined additional output score; and 2) mapping the combined additional output score to a categorical determination or to an inconclusive determination as to the presence or absence of the cognitive function attribute in the subject. The ratio of inconclusive to categorical determinations may be adjusted. The method may further comprise employing rule-based logic or combinatorial techniques for combining the numerical scores for each of the preliminary subset of assessment models and for combining the numerical scores for each of the additional assessment models.

The ratio of inconclusive to categorical determinations may be adjusted by specifying an inclusion rate and wherein the categorical determination as to the presence or absence of the developmental condition in the subject is assessed by providing a sensitivity and specificity metric. The inclusion rate may be no less than 70% with the categorical determination resulting in a sensitivity of at least 70 with a corresponding specificity in of at least 70. The inclusion rate may be no less than 70% with the categorical determination resulting in a sensitivity of at least 80 with a corresponding specificity in of at least 80. The inclusion rate may be no less than 70% with the categorical determination resulting in a sensitivity of at least 90 with a corresponding specificity in of at least 90. The data from the subject may comprise at least one of a sample of a diagnostic instrument, wherein the diagnostic instrument comprises a set of diagnostic questions and corresponding selectable answers, and demographic data.

The method may further comprise training a plurality of tunable machine learning assessment models using data from a plurality of subjects previously evaluated for the developmental condition. The training may comprise the operations of: 1) pre-processing the data from the plurality of subjects using machine learning techniques; 2) extracting and encoding machine learning features from the pre-processed data; 3) processing the data from the plurality of subjects to mirror an expected prevalence of a cognitive function attribute among subjects in an intended application setting; 4) selecting a subset of the processed machine learning features; 5) evaluating each model in the plurality of tunable machine learning assessment models for performance; and 6) determining an optimal set of parameters for each model based on determining the benefit of using all models in a selected subset of the plurality of tunable machine learning assessment models. Each model may be evaluated for sensitivity and specificity for a pre-determined inclusion rate. Determining an optimal set of parameters for each model may comprise tuning the parameters of each model under different tuning parameter settings. Processing the encoded machine learning features may comprise computing and assigning sample weights to every sample of data. Each sample of data may correspond to a subject in the plurality of subjects. Samples may be grouped according to subject-specific dimensions. Sample weights may be computed and assigned to balance one group of samples against every other group of samples to mirror the expected distribution of each dimension among subjects in an intended setting. The subject-specific dimensions may comprise a subject's gender, the geographic region where a subject resides, and a subject's age. Extracting and encoding machine learning features from the pre-processed data may comprise using feature encoding techniques such as but not limited to one-hot encoding, severity encoding, and presence-of-behavior encoding. Selecting a subset of the processed machine learning features may comprise using bootstrapping techniques to identify a subset of discriminating features from the processed machine learning features.

The cognitive function attribute may comprise a behavioral disorder and a developmental advancement. The categorical determination provided for the subject may be selected from the group consisting of an inconclusive determination, a presence of multiple cognitive function attributes and an absence of multiple cognitive function attributes in response to the data.

In another aspect, an apparatus to evaluate a cognitive function attribute of a subject may comprise a processor. The processor may be configured with instructions that, when executed, cause the processor to receive data of the subject related to the cognitive function attribute and applies rules to generate a categorical determination for the subject. The categorical determination may be selected from a group consisting of an inconclusive determination, a presence of the cognitive function attribute, and an absence of the cognitive function attribute in response to the data. The cognitive function attribute may be determined with a sensitivity of at least 70 and a specificity of at least 70, respectively, for the presence or the absence of the cognitive function attribute. The cognitive function attribute may be selected from a group consisting of autism, autistic spectrum, attention deficit disorder, attention deficit hyperactive disorder and speech and learning disability. The cognitive function attribute may be determined with a sensitivity of at least 80 and a specificity of at least 80, respectively, for the presence or the absence of the cognitive function attribute. The cognitive function attribute may be determined with a sensitivity of at least 90 and a specificity of at least 90, respectively, for the presence or the absence of the cognitive function attribute. The cognitive function attribute may comprise a behavioral disorder and a developmental advancement.

In another aspect, a non-transitory computer-readable storage media encoded with a computer program including instructions executable by a processor to evaluate a cognitive function attribute of a subject comprises a database, recorded on the media. The database may comprise data of a plurality of subjects related to at least one cognitive function attribute and a plurality of tunable machine learning assessment models; an evaluation software module; and a model tuning software module. The evaluation software module may comprise instructions for: 1) receiving data of the subject related to the cognitive function attribute; 2) evaluating the data of the subject using a selected subset of a plurality of machine learning assessment models; and 3) providing a categorical determination for the subject, the categorical determination selected from the group consisting of an inconclusive determination, a presence of the cognitive function attribute and an absence of the cognitive function attribute in response to the data. The model tuning software module may comprise instructions for: 1) pre-processing the data from the plurality of subjects using machine learning techniques; 2) extracting and encoding machine learning features from the pre-processed data; 3) processing the encoded machine learning features to mirror an expected distribution of subjects in an intended application setting; 4) selecting a subset of the processed machine learning features; 5) evaluating each model in the plurality of tunable machine learning assessment models for performance; 6) tuning the parameters of each model under different tuning parameter settings; and 7) determining an optimal set of parameters for each model based on determining the benefit of using all models in a selected subset of the plurality of tunable machine learning assessment models. Each model may be evaluated for sensitivity and specificity for a predetermined inclusion rate. The cognitive function attribute may comprise a behavioral disorder and a developmental advancement.

In another aspect, a computer-implemented system may comprise a digital processing device. The digital processing may comprise at least one processor, an operating system configured to perform executable instructions, a memory, and a computer program. The memory may comprise storage for housing data of a plurality of subjects related to at least one cognitive function attribute and storage for housing a plurality of machine learning assessment models. The computer program may include instructions executable by the digital processing device for: 1) receiving data of the subject related to the cognitive function attribute; 2) evaluating the data of the subject using a selected subset of a plurality of machine learning assessment models; and 3) providing a categorical determination for the subject, the categorical determination selected from the group consisting of an inconclusive determination, a presence of the cognitive function attribute and an absence of the cognitive function attribute in response to the data. The cognitive function attribute may comprise a behavioral disorder and a developmental advancement.

In another aspect, a mobile device for providing an evaluation of at least one cognitive function attribute of a subject may comprise a display and a processor. The processor may be configured with instructions to receive and display data of the subject related to the cognitive function attribute and receive and display an evaluation for the subject. The evaluation may be selected from the group consisting of an inconclusive determination and a categorical determination. The evaluation for the subject may be determined in response to the data of the subject. The categorical determination may be selected from the group consisting of a presence of the cognitive function attribute and an absence of the cognitive function attribute. The cognitive function attribute may be determined with a sensitivity of at least 80 and a specificity of at least 80, respectively, for the presence or the absence of the cognitive function attribute. The cognitive function attribute may be determined with a sensitivity of at least 90 and a specificity of at least 90, respectively, for the presence or the absence of the cognitive function attribute. The cognitive function attribute may comprise a behavioral disorder and a developmental advancement.

In another aspect, a digital therapeutic system to treat a subject with a personal therapeutic treatment plan may comprise one or more processors, a diagnostic module to receive data from the subject and output diagnostic data for the subject, and a therapeutic module to receive the diagnostic data and output the personal therapeutic treatment plan for the subject. The diagnostic module may comprise one or more classifiers built using machine learning or statistical modeling based on a subject population to determine the diagnostic data for the subject. The diagnostic data may comprise an evaluation for the subject, the evaluation selected from the group consisting of an inconclusive determination and a categorical determination in response to data received from the subject. The therapeutic module may comprise one or more models built using machine learning or statistical modeling based on at least a portion the subject population to determine and output the personal therapeutic treatment plan of the subject. The diagnostic module may be configured to receive updated subject data from the subject in response to therapy of the subject and generate updated diagnostic data from the subject. The therapeutic module may be configured to receive the updated diagnostic data and output an updated personal treatment plan for the subject in response to the diagnostic data and the updated diagnostic data. The diagnostic module may comprise a diagnostic machine learning classifier trained on the subject population. The therapeutic module may comprise a therapeutic machine learning classifier trained on the at least the portion of the subject population. The diagnostic module and the therapeutic module may be arranged for the diagnostic module to provide feedback to the therapeutic module based on performance of the treatment plan. The therapeutic classifier may comprise instructions trained on a data set comprising a population of which the subject is not a member. The subject may comprise a person who is not a member of the population. The diagnostic module may comprise a diagnostic classifier trained on plurality of profiles of a subject population of at least 10,000 people and therapeutic profile trained on the plurality of profiles of the subject population.

In another aspect, a digital therapeutic system to treat a subject with a personal therapeutic treatment plan may comprise a processor, a diagnostic module to receive data from the subject and output diagnostic data for the subject, and a therapeutic module to receive the diagnostic data and output the personal therapeutic treatment plan for the subject. The diagnostic data may comprise an evaluation for the subject, the evaluation selected from the group consisting of an inconclusive determination and a categorical determination in response to data received from the subject. The personal therapeutic treatment plan may comprise digital therapeutics. The digital therapeutics may comprise instructions, feedback, activities or interactions provided to the subject or caregiver. The digital therapeutics may be provided with a mobile device. The diagnostics data and the personal therapeutic treatment plan may be provided to a third-party system. The third-party system may comprise a computer system of a health care professional or a therapeutic delivery system. The diagnostic module may be configured to receive updated subject data from the subject in response to a feedback data of the subject and generate updated diagnostic data. The therapeutic module may be configured to receive the updated diagnostic data and output an updated personal treatment plan for the subject in response to the diagnostic data and the updated diagnostic data. The updated subject data may be received in response to a feedback data that identifies relative levels of efficacy, compliance and response resulting from the personal therapeutic treatment plan. The diagnostic module may use machine learning or statistical modeling based on a subject population to determine the diagnostic data. The therapeutic module may be based on at least a portion the subject population to determine the personal therapeutic treatment plan of the subject. The diagnostic module may comprise a diagnostic machine learning classifier trained on a subject population. The therapeutic module may comprise a therapeutic machine learning classifier trained on at least a portion of the subject population. The diagnostic module may be configured to provide feedback to the therapeutic module based on performance of the personal therapeutic treatment plan. The data from the subject may comprise at least one of the subject and caregiver video, audio, responses to questions or activities, and active or passive data streams from user interaction with activities, games or software features of the system. The subject may have a risk selected from the group consisting of a behavioral disorder, neurological disorder and mental health disorder. The behavioral, neurological or mental health disorder may be selected from the group consisting of autism, autistic spectrum, attention deficit disorder, depression, obsessive compulsive disorder, schizophrenia, Alzheimer's disease, dementia, attention deficit hyperactive disorder and speech and learning disability. The diagnostic module may be configured for an adult to perform an assessment or provide data for an assessment of a child or juvenile. The diagnostic module may be configured for a caregiver or family member to perform an assessment or provide data for an assessment of the subject.

In another aspect, a non-transitory computer-readable storage media may be encoded with a program. The computer program may include executable instructions for: 1) receiving input data from the subject and outputting diagnostic data for the subject; 2) receiving the diagnostic data and outputting a personal therapeutic treatment plan for the subject; and 3) evaluating the diagnostic data based on at least a portion the subject population to determine and output the personal therapeutic treatment plan of the subject. The diagnostic data may comprise an evaluation for the subject, the evaluation selected from the group consisting of an inconclusive determination and a categorical determination in response to input data received from the subject. Updated subject input data may be received from the subject in response to therapy of the subject and updated diagnostic data may be generated from the subject. Updated diagnostic data may be received and an updated personal treatment plan may be outputted for the subject in response to the diagnostic data and the updated diagnostic data.

In another aspect, a non-transitory computer-readable storage media may be encoded with a computer program. The computer program may include executable instructions for receiving input data from a subject and outputting diagnostic data for the subject and receiving the diagnostic data and outputting a personal therapeutic treatment plan for the subject. The diagnostic data may comprise an evaluation for the subject, the evaluation selected from the group consisting of an inconclusive determination and a categorical determination in response to data received from the subject. The personal therapeutic treatment plan may comprise digital therapeutics.

In another aspect, a method of treating a subject with a personal therapeutic treatment plan may comprise a diagnostic process of receiving data from the subject and outputting diagnostic data for the subject wherein the diagnostic data comprises an evaluation for the subject and a therapeutic process of receiving the diagnostic data and outputting the personal therapeutic treatment plan for the subject. The evaluation may be selected from the group consisting of an inconclusive determination and a categorical determination in response to data received from the subject. The diagnostic process may comprise receiving updated subject data from the subject in response to a therapy of the subject and generating an updated diagnostic data from the subject. The therapeutic process may comprise receiving the updated diagnostic data and outputting an updated personal treatment plan for the subject in response to the diagnostic data and the updated diagnostic data. The updated subject data may be received in response to a feedback data that identifies relative levels of efficacy, compliance and response resulting from the personal therapeutic treatment plan. The personal therapeutic treatment plan may comprise digital therapeutics. The digital therapeutics may comprise instructions, feedback, activities or interactions provided to the subject or caregiver. The digital therapeutics may be provided with a mobile device. The method may further comprise providing the diagnostics data and the personal therapeutic treatment plan to a third-party system. The third-party system may comprise a computer system of a health care professional or a therapeutic delivery system. The diagnostic process may be performed by a process selected from the group consisting of machine learning, a classifier, artificial intelligence, or statistical modeling based on a subject population to determine the diagnostic data. The therapeutic process may be performed by a process selected from the group consisting of machine learning, a classifier, artificial intelligence, or statistical modeling based on at least a portion the subject population to determine the personal therapeutic treatment plan of the subject. The diagnostic process may be performed by a diagnostic machine learning classifier trained on a subject population. The therapeutic process may be performed by a therapeutic machine learning classifier trained on at least a portion of the subject population. The diagnostic process may comprise providing feedback to the therapeutic module based on performance of the personal therapeutic treatment plan. The data from the subject may comprise at least one of the subject and caregiver video, audio, responses to questions or activities, and active or passive data streams from user interaction with activities, games or software features. The diagnostic process may be performed by an adult to perform an assessment or provide data for an assessment of a child or juvenile. The diagnostic process may enable a caregiver or family member to perform an assessment or provide data for an assessment of the subject. The subject may have a risk selected from the group consisting of a behavioral disorder, neurological disorder, and mental health disorder. The risk may be selected from the group consisting of autism, autistic spectrum, attention deficit disorder, depression, obsessive compulsive disorder, schizophrenia, Alzheimer's disease, dementia, attention deficit hyperactive disorder, and speech and learning disability.

Figure 1B:
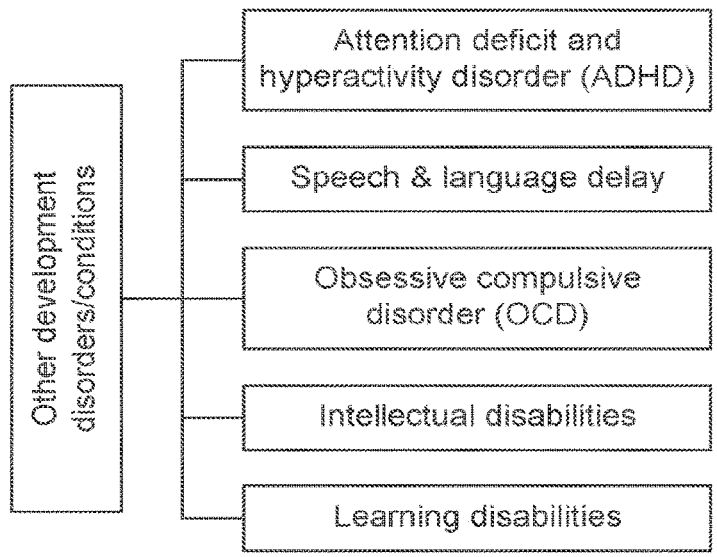

FIGS. 1A and 1B show some exemplary developmental disorders that may be evaluated using the assessment procedure as described herein. The assessment procedure can be configured to evaluate a subject's risk for having one or more developmental disorders, such as two or more related developmental disorders. The developmental disorders may have at least some overlap in symptoms or features of the subject. Such developmental disorders may include pervasive development disorder (PDD), autism spectrum disorder (ASD), social communication disorder, restricted repetitive behaviors, interests, and activities (RRBs), autism ("classical autism"), Asperger's Syndrome ("high functioning autism), PDD-not otherwise specified (PDD-NOS, "atypical autism"), attention deficit and hyperactivity disorder (ADHD), speech and language delay, obsessive compulsive disorder (OCD), intellectual disability, learning disability, or any other relevant development disorder, such as disorders defined in any edition of the Diagnostic and Statistical Manual of Mental Disorders (DSM). The assessment procedure may be configured to determine the risk of the subject for having each of a plurality of disorders. The assessment procedure may be configured to determine the subject as at greater risk of a first disorder or a second disorder of the plurality of disorders. The assessment procedure may be configured to determine the subject as at risk of a first disorder and a second disorder with comorbidity. The assessment procedure may be configured to predict a subject to have normal development, or have low risk of having any of the disorders the procedure is configured to screen for. The assessment procedure may further be configured to have high sensitivity and specificity to distinguish among different severity ratings for a disorder; for example, the procedure may be configured to predict a subject's risk for having level 1 ASD, level 2 ASD, or level 3 ASD as defined in the fifth edition of the DSM (DSM-V).

Many developmental disorders may have similar or overlapping symptoms, thus complicating the assessment of a subject's developmental disorder. The assessment procedure described herein can be configured to evaluate a plurality of features of the subject that may be relevant to one or more developmental disorders. The procedure can comprise an assessment model that has been trained using a large set of clinically validated data to learn the statistical relationship between a feature of a subject and clinical diagnosis of one or more developmental disorders. Thus, as a subject participates in the assessment procedure, the subject's feature value for each evaluated feature (e.g., subject's answer to a question) can be queried against the assessment model to identify the statistical correlation, if any, of the subject's feature value to one or more screened developmental disorders. Based on the feature values provided by the subject, and the relationship between those values and the predicted risk for one or more developmental disorders as determined by the assessment model, the assessment procedure can dynamically adjust the selection of next features to be evaluated in the subject. The selection of the next feature to be evaluated may comprise an identification of the next most predictive feature, based on the determination of the subject as at risk for a particular disorder of the plurality of disorders being screened. For example, if after the subject has answered the first five questions of the assessment procedure, the assessment model predicts a low risk of autism and a relatively higher risk of ADHD in the subject, the assessment procedure may select features with higher relevance to ADHD to be evaluated next in the subject (e.g., questions whose answers are highly correlated with a clinical diagnosis of ADHD may be presented next to the subject). Thus, the assessment procedure described herein can be dynamically tailored to a particular subject's risk profile, and enable the evaluation of the subject's disorder with a high level of granularity.

Figure 2:
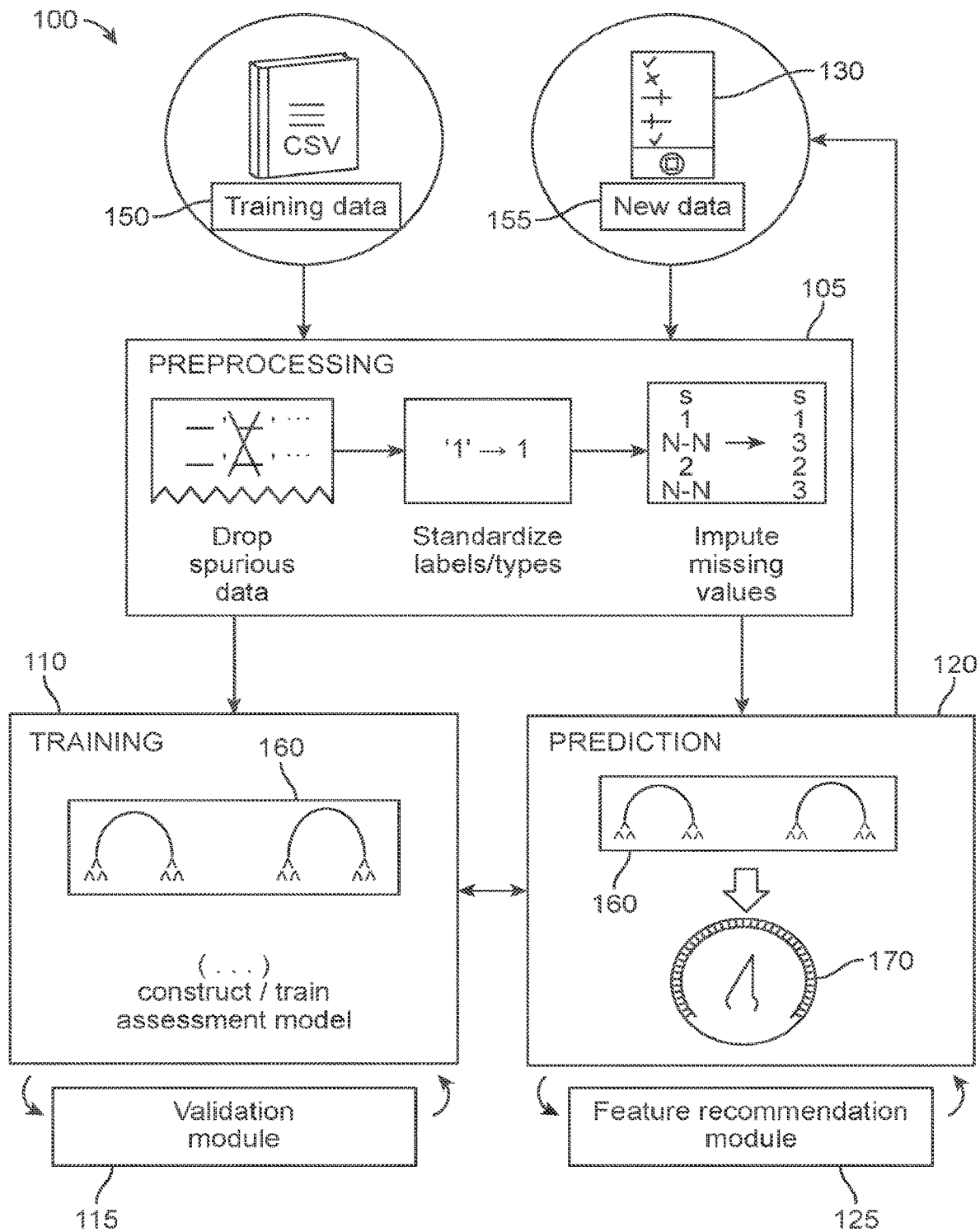
FIG. 2 is a schematic diagram of an exemplary data processing module for providing the assessment procedure as described herein.

FIG. 2 is a schematic diagram of an exemplary data processing module 100 for providing the assessment procedure as described herein. The data processing module 100 generally comprises a preprocessing module 105, a training module 110, and a prediction module 120. The data processing module can extract training data 150 from a database, or intake new data 155 with a user interface 130. The preprocessing module can apply one or more transformations to standardize the training data or new data for the training module or the prediction module. The preprocessed training data can be passed to the training module, which can construct an assessment model 160 based on the training data. The training module may further comprise a validation module 115, configured to validate the trained assessment model using any appropriate validation algorithm (e.g., Stratified K-fold cross-validation). The preprocessed new data can be passed on to the prediction module, which may output a prediction 170 of the subject's developmental disorder by fitting the new data to the assessment model constructed in the training module. The prediction module may further comprise a feature recommendation module 125, configured to select or recommend the next feature to be evaluated in the subject, based on previously provided feature values for the subject.

The training data 150, used by the training module to construct the assessment model, can comprise a plurality of datasets from a plurality of subjects, each subject's dataset comprising an array of features and corresponding feature values, and a classification of the subject's developmental disorder or condition. As described herein, the features may be evaluated in the subject via one or more of questions asked to the subject, observations of the subject, or structured interactions with the subject. Feature values may comprise one or more of answers to the questions, observations of the subject such as characterizations based on video images, or responses of the subject to a structured interaction, for example. Each feature may be relevant to the identification of one or more developmental disorders or conditions, and each corresponding feature value may indicate the degree of presence of the feature in the specific subject. For example, a feature may be the ability of the subject to engage in imaginative or pretend play, and the feature value for a particular subject may be a score of either 0, 1, 2, 3, or 8, wherein each score corresponds to the degree of presence of the feature in the subject (e.g., 0=variety of pretend play; 1=some pretend play; 2=occasional pretending or highly repetitive pretend play; 3=no pretend play; 8=not applicable). The feature may be evaluated in the subject by way of a question presented to the subject or a caretaker such as a parent, wherein the answer to the question comprises the feature value. Alternatively or in combination, the feature may be observed in the subject, for example with a video of the subject engaging in a certain behavior, and the feature value may be identified through the observation. In addition to the array of features and corresponding feature values, each subject's dataset in the training data also comprises a classification of the subject. For example, the classification may be autism, autism spectrum disorder (ASD), or non-spectrum. Preferably, the classification comprises a clinical diagnosis, assigned by qualified personnel such as licensed clinical psychologists, in order to improve the predictive accuracy of the generated assessment model. The training data may comprise datasets available from large data repositories, such as Autism Diagnostic Interview-Revised (ADI-R) data and/or Autism Diagnostic Observation Schedule (ADOS) data available from the Autism Genetic Resource Exchange (AGRE), or any datasets available from any other suitable repository of data (e.g., Boston Autism Consortium (AC), Simons Foundation, National Database for Autism Research, etc.). Alternatively or in combination, the training data may comprise large self-reported datasets, which can be crowd-sourced from users (e.g., via websites, mobile applications, etc.).

The preprocessing module 105 can be configured to apply one or more transformations to the extracted training data to clean and normalize the data, for example. The preprocessing module can be configured to discard features which contain spurious metadata or contain very few observations. The preprocessing module can be further configured to standardize the encoding of feature values. Different datasets may often have the same feature value encoded in different ways, depending on the source of the dataset. For example, '900', '900.0', '904', '904.0', '−1', '−1.0', 'None', and 'NaN' may all encode for a "missing" feature value. The preprocessing module can be configured to recognize the encoding variants for the same feature value, and standardize the datasets to have a uniform encoding for a given feature value. The preprocessing module can thus reduce irregularities in the input data for the training and prediction modules, thereby improving the robustness of the training and prediction modules.

In addition to standardizing data, the preprocessing module can also be configured to re-encode certain feature values into a different data representation. In some instances, the original data representation of the feature values in a dataset may not be ideal for the construction of an assessment model. For example, for a categorical feature wherein the corresponding feature values are encoded as integers from 1 to 9, each integer value may have a different semantic content that is independent of the other values. For example, a value of '1' and a value of '9' may both be highly correlated with a specific classification, while a value of '5' is not. The original data representation of the feature value, wherein the feature value is encoded as the integer itself, may not be able to capture the unique semantic content of each value, since the values are represented in a linear model (e.g., an answer of '5' would place the subject squarely between a '1' and a '9' when the feature is considered in isolation; however, such an interpretation would be incorrect in the aforementioned case wherein a '1' and a '9' are highly correlated with a given classification while a '5' is not). To ensure that the semantic content of each feature value is captured in the construction of the assessment model, the preprocessing module may comprise instructions to re-encode certain feature values, such as feature values corresponding to categorical features, in a "one-hot" fashion, for example. In a "one-hot" representation, a feature value may be represented as an array of bits having a value of 0 or 1, the number of bits corresponding to the number of possible values for the feature. Only the feature value for the subject may be represented as a "1", with all other values represented as a "0". For example, if a subject answered "4" to a question whose possible answers comprise integers from 1 to 9, the original data representation may be [4], and the one-hot representation may be [0 0 0 1 0 0 0 0 0]. Such a one-hot representation of feature values can allow every value to be considered independently of the other possible values, in cases where such a representation would be necessary. By thus re-encoding the training data using the most appropriate data representation for each feature, the preprocessing module can improve the accuracy of the assessment model constructed using the training data.

The preprocessing module can be further configured to impute any missing data values, such that downstream modules can correctly process the data. For example, if a training dataset provided to the training module comprises data missing an answer to one of the questions, the preprocessing module can provide the missing value, so that the dataset can be processed correctly by the training module. Similarly, if a new dataset provided to the prediction module is missing one or more feature values (e.g., the dataset being queried comprises only the answer to the first question in a series of questions to be asked), the preprocessing module can provide the missing values, so as to enable correct processing of the dataset by the prediction module. For features having categorical feature values (e.g., extent of display of a certain behavior in the subject), missing values can be provided as appropriate data representations specifically designated as such. For example, if the categorical features are encoded in a one-hot representation as described herein, the preprocessing module may encode a missing categorical feature value as an array of '0' bits. For features having continuous feature values (e.g., age of the subject), the mean of all of the possible values can be provided in place of the missing value (e.g., age of 4 years).

The training module 110 can utilize a machine learning algorithm or other algorithm to construct and train an assessment model to be used in the assessment procedure, for example. An assessment model can be constructed to capture, based on the training data, the statistical relationship, if any, between a given feature value and a specific developmental disorder to be screened by the assessment procedure. The assessment model may, for example, comprise the statistical correlations between a plurality of clinical characteristics and clinical diagnoses of one or more developmental disorders. A given feature value may have a different predictive utility for classifying each of the plurality of developmental disorders to be evaluated in the assessment procedure. For example, in the aforementioned example of a feature comprising the ability of the subject to engage in imaginative or pretend play, the feature value of "3" or "no variety of pretend play" may have a high predictive utility for classifying autism, while the same feature value may have low predictive utility for classifying ADHD. Accordingly, for each feature value, a probability distribution may be extracted that describes the probability of the specific feature value for predicting each of the plurality of developmental disorders to be screened by the assessment procedure. The machine learning algorithm can be used to extract these statistical relationships from the training data and build an assessment model that can yield an accurate prediction of a developmental disorder when a dataset comprising one or more feature values is fitted to the model.

One or more machine learning algorithms may be used to construct the assessment model, such as support vector machines that deploy stepwise backwards feature selection and/or graphical models, both of which can have advantages of inferring interactions between features. For example, machine learning algorithms or other statistical algorithms may be used, such as alternating decision trees (ADTree), Decision Stumps, functional trees (FT), logistic model trees (LMT), logistic regression, Random Forests, linear classifiers, or any machine learning algorithm or statistical algorithm known in the art. One or more algorithms may be used together to generate an ensemble method, wherein the ensemble method may be optimized using a machine learning ensemble meta-algorithm such as a boosting (e.g., AdaBoost, LPBoost, TotalBoost, BrownBoost, MadaBoost, LogitBoost, etc.) to reduce bias and/or variance. Once an assessment model is derived from the training data, the model may be used as a prediction tool to assess the risk of a subject for having one or more developmental disorders. Machine learning analyses may be performed using one or more of many programming languages and platforms known in the art, such as R, Weka, Python, and/or Matlab, for example.

A Random Forest classifier, which generally comprises a plurality of decision trees wherein the output prediction is the mode of the predicted classifications of the individual trees, can be helpful in reducing overfitting to training data. An ensemble of decision trees can be constructed using a random subset of features at each split or decision node. The Gini criterion may be employed to choose the best partition, wherein decision nodes having the lowest calculated Gini impurity index are selected. At prediction time, a "vote" can be taken over all of the decision trees, and the majority vote (or mode of the predicted classifications) can be output as the predicted classification.

Figure 3:
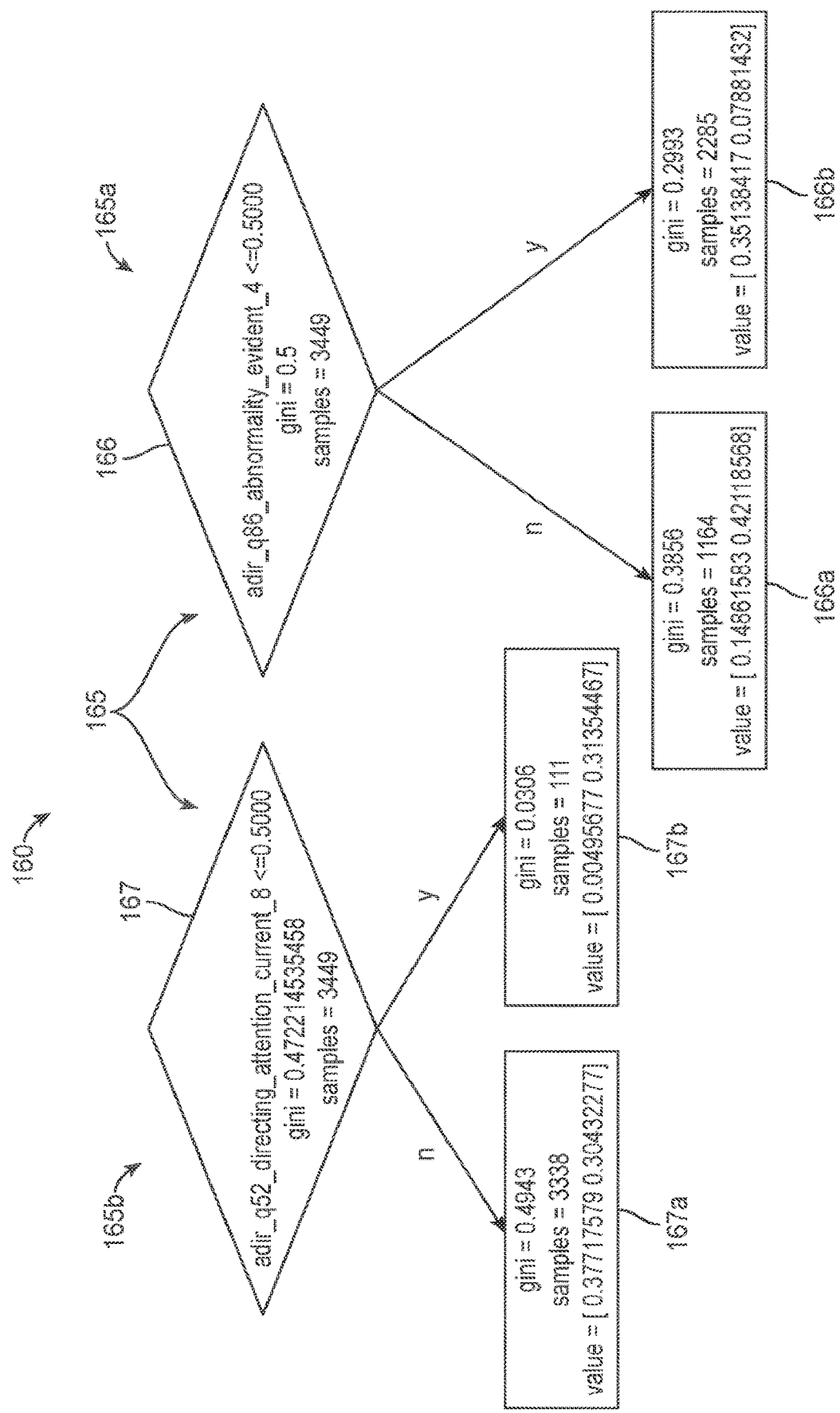
FIG. 3 is a schematic diagram illustrating a portion of an exemplary assessment model based on a Random Forest classifier.

FIG. 3 is a schematic diagram illustrating a portion of an exemplary assessment model 160 based on a Random Forest classifier. The assessment module may comprise a plurality of individual decision trees 165, such as decision trees 165a and 165b, each of which can be generated independently using a random subset of features in the training data. Each decision tree may comprise one or more decision nodes such as decision nodes 166 and 167 shown in FIG. 3, wherein each decision node specifies a predicate condition. For example, decision node 16 predicates the condition that, for a given dataset of an individual, the answer to ADI-R question #86 (age when abnormality is first evident) is 4 or less. Decision node 167 predicates the condition that, for the given dataset, the answer to ADI-R question #52 (showing and direction attention) is 8 or less. At each decision node, a decision tree can be split based on whether the predicate condition attached to the decision node holds true, leading to prediction nodes (e.g., 166a, 166b, 167a, 167b). Each prediction node can comprise output values ('value' in FIG. 3) that represent "votes" for one or more of the classifications or conditions being evaluated by the assessment model. For example, in the prediction nodes shown in FIG. 3, the output values comprise votes for the individual being classified as having autism or being non-spectrum. A prediction node can lead to one or more additional decision nodes downstream (not shown in FIG. 3), each decision node leading to an additional split in the decision tree associated with corresponding prediction nodes having corresponding output values. The Gini impurity can be used as a criterion to find informative features based on which the splits in each decision tree may be constructed.

When the dataset being queried in the assessment model reaches a "leaf", or a final prediction node with no further downstream splits, the output values of the leaf can be output as the votes for the particular decision tree. Since the Random Forest model comprises a plurality of decision trees, the final votes across all trees in the forest can be summed to yield the final votes and the corresponding classification of the subject. While only two decision trees are shown in FIG. 3, the model can comprise any number of decision trees. A large number of decision trees can help reduce overfitting of the assessment model to the training data, by reducing the variance of each individual decision tree. For example, the assessment model can comprise at least about 10 decision trees, for example at least about 100 individual decision trees or more.

An ensemble of linear classifiers may also be suitable for the derivation of an assessment model as described herein. Each linear classifier can be individually trained with a stochastic gradient descent, without an "intercept term". The lack of an intercept term can prevent the classifier from deriving any significance from missing feature values. For example, if a subject did not answer a question such that the feature value corresponding to said question is represented as an array of '0' bits in the subject's data set, the linear classifier trained without an intercept term will not attribute any significance to the array of '0' bits. The resultant assessment model can thereby avoid establishing a correlation between the selection of features or questions that have been answered by the subject and the final classification of the subject as determined by the model. Such an algorithm can help ensure that only the subject-provided feature values or answers, rather than the features or questions, are factored into the final classification of the subject.

The training module may comprise feature selection. One or more feature selection algorithms (such as support vector machine, convolutional neural nets) may be used to select features able to differentiate between individuals with and without certain developmental disorders. Different sets of features may be selected as relevant for the identification of different disorders. Stepwise backwards algorithms may be used along with other algorithms. The feature selection procedure may include a determination of an optimal number of features.

The training module may be configured to evaluate the performance of the derived assessment models. For example, the accuracy, sensitivity, and specificity of the model in classifying data can be evaluated. The evaluation can be used as a guideline in selecting suitable machine learning algorithms or parameters thereof. The training module can thus update and/or refine the derived assessment model to maximize the specificity (the true negative rate) over sensitivity (the true positive rate). Such optimization may be particularly helpful when class imbalance or sample bias exists in training data.

In at least some instances, available training data may be skewed towards individuals diagnosed with a specific developmental disorder. In such instances, the training data may produce an assessment model reflecting that sample bias, such that the model assumes that subjects are at risk for the specific developmental disorder unless there is a strong case to be made otherwise. An assessment model incorporating such a particular sample bias can have less than ideal performance in generating predictions of new or unclassified data, since the new data may be drawn from a subject population which may not comprise a sample bias similar to that present in the training data. To reduce sample bias in constructing an assessment model using skewed training data, sample weighting may be applied in training the assessment model. Sample weighting can comprise lending a relatively greater degree of significance to a specific set of samples during the model training process. For example, during model training, if the training data is skewed towards individuals diagnosed with autism, higher significance can be attributed to the data from individuals not diagnosed with autism (e.g., up to 50 times more significance than data from individuals diagnosed with autism). Such a sample weighting technique can substantially balance the sample bias present in the training data, thereby producing an assessment model with reduced bias and improved accuracy in classifying data in the real world. To further reduce the contribution of training data sample bias to the generation of an assessment model, a boosting technique may be implemented during the training process. Boosting comprises an iterative process, wherein after one iteration of training, the weighting of each sample data point is updated. For example, samples that are misclassified after the iteration can be updated with higher significances. The training process may then be repeated with the updated weightings for the training data.

The training module may further comprise a validation module 115 configured to validate the assessment model constructed using the training data. For example, a validation module may be configured to implement a Stratified K-fold cross validation, wherein k represents the number of partitions that the training data is split into for cross validation. For example, k can be any integer greater than 1, such as 3, 4, 5, 6, 7, 8, 9, or 10, or possibly higher depending on risk of overfitting the assessment model to the training data.

The training module may be configured to save a trained assessment model to a local memory and/or a remote server, such that the model can be retrieved for modification by the training module or for the generation of a prediction by the prediction module 120.

Figure 4:
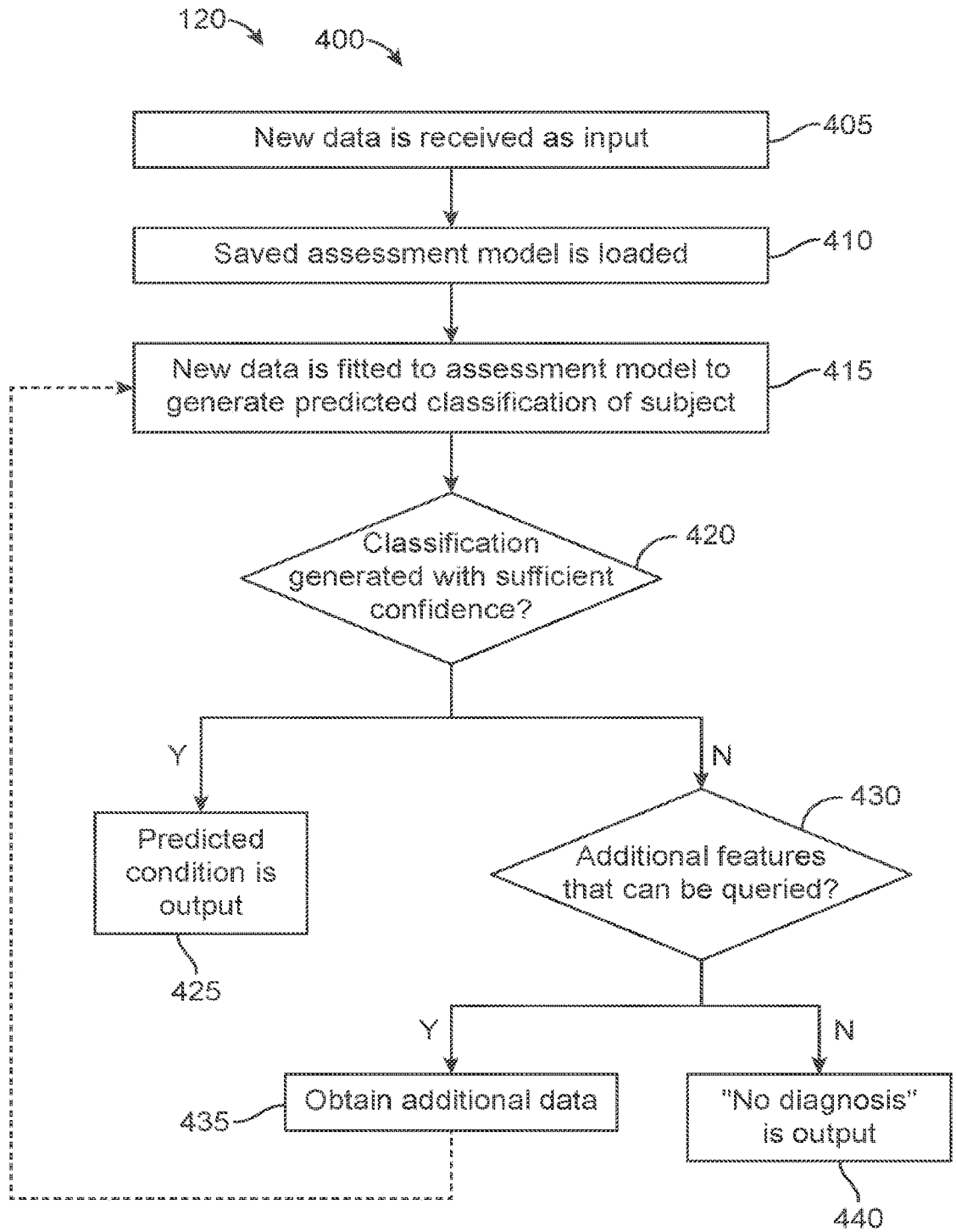
FIG. 4 is an exemplary operational flow of a prediction module as described herein.

FIG. 4 is an exemplary operational flow 400 of a method of a prediction module 120 as described herein. The prediction module 120 can be configured to generate a predicted classification (e.g., developmental disorder) of a given subject, by fitting new data to an assessment model constructed in the training module. At step 405, the prediction module can receive new data that may have been processed by the preprocessing module to standardize the data, for example by dropping spurious metadata, applying uniform encoding of feature values, re-encoding select features using different data representations, and/or imputing missing data points, as described herein. The new data can comprise an array of features and corresponding feature values for a particular subject. As described herein, the features may comprise a plurality of questions presented to a subject, observations of the subject, or tasks assigned to the subject. The feature values may comprise input data from the subject corresponding to characteristics of the subject, such as answers of the subject to questions asked, or responses of the subject. The new data provided to the prediction module may or may not have a known classification or diagnosis associated with the data; either way, the prediction module may not use any pre-assigned classification information in generating the predicted classification for the subject. The new data may comprise a previously-collected, complete dataset for a subject to be diagnosed or assessed for the risk of having one or more of a plurality of developmental disorders. Alternatively or in combination, the new data may comprise data collected in real time from the subject or a caretaker of the subject, for example with a user interface as described in further detail herein, such that the complete dataset can be populated in real time as each new feature value provided by the subject is sequentially queried against the assessment model.

At step 410, the prediction module can load a previously saved assessment model, constructed by the training module, from a local memory and/or a remote server configured to store the model. At step 415, the new data is fitted to the assessment model to generate a predicted classification of the subject. At step 420, the module can check whether the fitting of the data can generate a prediction of one or more specific disorders (e.g., autism, ADHD, etc.) within a confidence interval exceeding a threshold value, for example within a 90% or higher confidence interval, for example 95% or more. If so, as shown in step 425, the prediction module can output the one or more developmental disorders as diagnoses of the subject or as disorders for which the subject is at risk. The prediction module may output a plurality of developmental disorders for which the subject is determined to at risk beyond the set threshold, optionally presenting the plurality of disorders in order of risk. The prediction module may output one developmental disorder for which the subject is determined to be at greatest risk. The prediction module may output two or more development disorders for which the subject is determined to risk with comorbidity. The prediction module may output determined risk for each of the one or more developmental disorders in the assessment model. If the prediction module cannot fit the data to any specific developmental disorder within a confidence interval at or exceeding the designated threshold value, the prediction module may determine, in step 430, whether there are any additional features that can be queried. If the new data comprises a previously-collected, complete dataset, and the subject cannot be queried for any additional feature values, "no diagnosis" may be output as the predicted classification, as shown in step 440. If the new data comprises data collected in real time from the subject or caretaker during the prediction process, such that the dataset is updated with each new input data value provided to the prediction module and each updated dataset is fitted to the assessment model, the prediction module may be able to query the subject for additional feature values. If the prediction module has already obtained data for all features included in the assessment module, the prediction module may output "no diagnosis" as the predicted classification of the subject, as shown in step 440. If there are features that have not yet been presented to the subject, as shown in step 435, the prediction module may obtain additional input data values from the subject, for example by presenting additional questions to the subject. The updated dataset including the additional input data may then be fitted to the assessment model again (step 415), and the loop may continue until the prediction module can generate an output.

Figure 5:
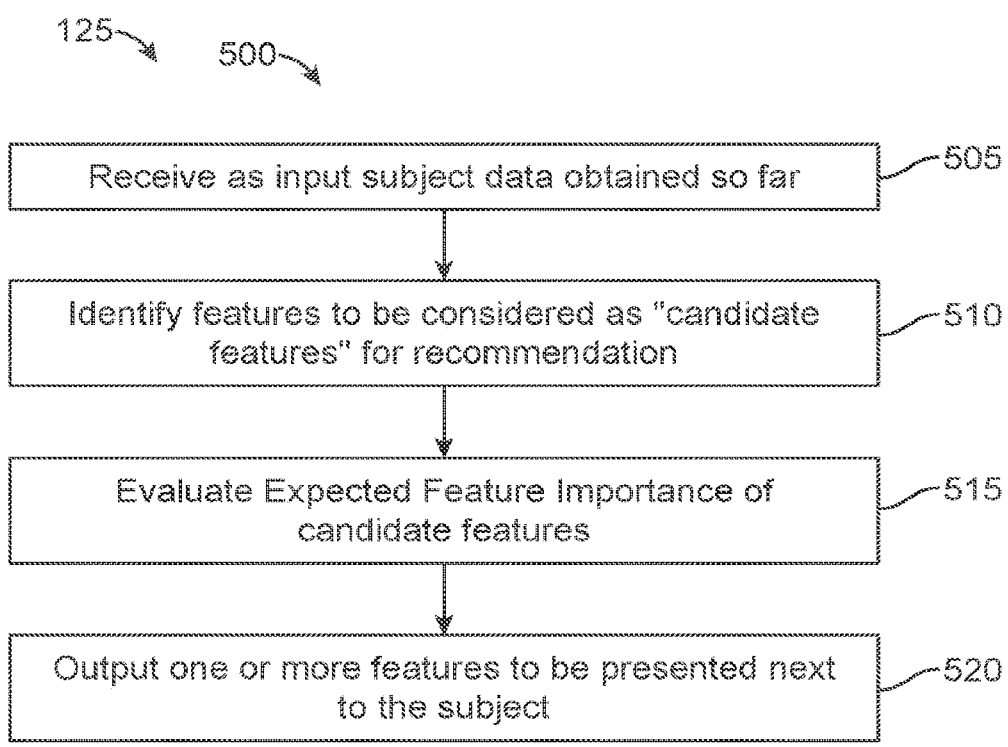
FIG. 5 is an exemplary operational flow of a feature recommendation module as described herein.

FIG. 5 is an exemplary operational flow 500 of a feature recommendation module 125 as described herein by way of a non-limiting example. The prediction module may comprise a feature recommendation module 125, configured to identify, select or recommend the next most predictive or relevant feature to be evaluated in the subject, based on previously provided feature values for the subject. For example, the feature recommendation module can be a question recommendation module, wherein the module can select the most predictive next question to be presented to a subject or caretaker, based on the answers to previously presented questions. The feature recommendation module can be configured to recommend one or more next questions or features having the highest predictive utility in classifying a particular subject's developmental disorder. The feature recommendation module can thus help to dynamically tailor the assessment procedure to the subject, so as to enable the prediction module to produce a prediction with a reduced length of assessment and improved sensitivity and accuracy. Further, the feature recommendation module can help improve the specificity of the final prediction generated by the prediction module, by selecting features to be presented to the subject that are most relevant in predicting one or more specific developmental disorders that the particular subject is most likely to have, based on feature values previously provided by the subject.

At step 505, the feature recommendation module can receive as input the data already obtained from the subject in the assessment procedure. The input subject data can comprise an array of features and corresponding feature values provided by the subject. At step 510, the feature recommendation module can select one or more features to be considered as "candidate features" for recommendation as the next feature(s) to be presented to one or more of the subject, caretaker or clinician. Features that have already been presented can be excluded from the group of candidate features to be considered. Optionally, additional features meeting certain criteria may also be excluded from the group of candidate features, as described in further detail herein.

At step 515, the feature recommendation module can evaluate the "expected feature importance" of each candidate feature. The candidate features can be evaluated for their "expected feature importance", or the estimated utility of each candidate feature in predicting a specific developmental disorder for the specific subject. The feature recommendation module may utilize an algorithm based on: (1) the importance or relevance of a specific feature value in predicting a specific developmental disorder; and (2) the probability that the subject may provide the specific feature value. For example, if the answer of "3" to ADOS question B5 is highly correlated with a classification of autism, this answer can be considered a feature value having high utility for predicting autism. If the subject at hand also has a high probability of answering "3" to said question B5, the feature recommendation module can determine this question to have high expected feature importance. An algorithm that can be used to determine the expected feature importance of a feature is described in further detail in reference to FIG. 6, for example.

At step 520, the feature recommendation module can select one or more candidate features to be presented next to the subject, based on the expected feature importance of the features as determined in step 515. For example, the expected feature importance of each candidate feature may be represented as a score or a real number, which can then be ranked in comparison to other candidate features. The candidate feature having the desired rank, for example a top 10, top 5, top 3, top 2, or the highest rank, may be selected as the feature to the presented next to the subject.

Figure 6:
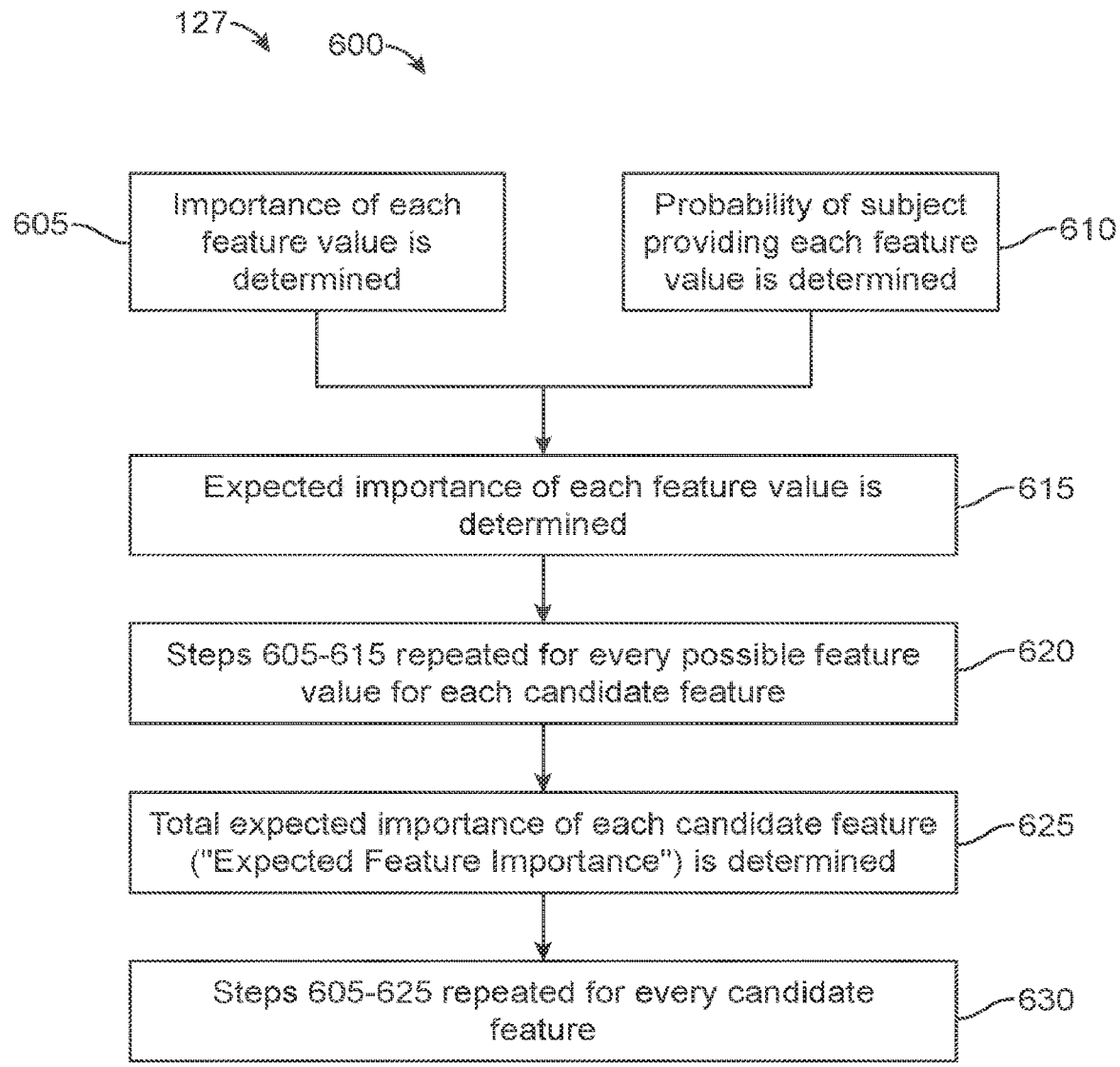
FIG. 6 is an exemplary operational flow of an expected feature importance determination algorithm as performed by a feature recommendation module described herein.

FIG. 6 is an exemplary operational flow 600 of method of determining an expected feature importance determination algorithm 127 as performed by a feature recommendation module 125 described herein.

At step 605, the algorithm can determine the importance or relevance of a specific feature value in predicting a specific developmental disorder. The importance or relevance of a specific feature value in predicting a specific developmental disorder can be derived from the assessment model constructed using training data. Such a "feature value importance" can be conceptualized as a measure of how relevant a given feature value's role is, should it be present or not present, in determining a subject's final classification. For example, if the assessment model comprises a Random Forest classifier, the importance of a specific feature value can be a function of where that feature is positioned in the Random Forest classifier's branches. Generally, if the average position of the feature in the decision trees is relatively high, the feature can have relatively high feature importance. The importance of a feature value given a specific assessment model can be computed efficiently, either by the feature recommendation module or by the training module, wherein the training module may pass the computed statistics to the feature recommendation module. Alternatively, the importance of a specific feature value can be a function of the actual prediction confidence that would result if said feature value was provided by the subject. For each possible feature value for a given candidate feature, the feature recommendation module can be configured to calculate the actual prediction confidence for predicting one or more developmental disorders, based on the subject's previously provided feature values and the currently assumed feature value.

Each feature value may have a different importance for each developmental disorder for which the assessment procedure is designed to screen. Accordingly, the importance of each feature value may be represented as a probability distribution that describes the probability of the feature value yielding an accurate prediction for each of the plurality of developmental disorders being evaluated.

At step 610, the feature recommendation module can determine the probability of a subject providing each feature value. The probability that the subject may provide a specific feature value can be computed using any appropriate statistical model. For example, a large probabilistic graphical model can be used to find the values of expressions such as:

$$prob(E = 1 \mid A = 1, B = 2, C = 1)$$

where A, B, and C represent different features or questions in the prediction module and the integers 1 and 2 represent different possible feature values for the feature (or possible answers to the questions). The probability of a subject providing a specific feature value may then be computed using Bayes' rule, with expressions such as:

$$prob(E = 1 | A = 1, B = 2, C = 1) =$$
$$prob(E = 1, A = 1, B = 2, C = 1) / prob(A = 1, B = 2, C = 1)$$

Such expressions may be computationally expensive, in terms of both computation time and required processing resources. Alternatively or in combination with computing the probabilities explicitly using Bayes' rule, logistic regression or other statistical estimators may be used, wherein the probability is estimated using parameters derived from a machine learning algorithm. For example, the following expression may be used to estimate the probability that the subject may provide a specific feature value:

$$prob(E = 1 | A = 1, B = 2, C = 1) \approx sigmoid(a1^*A + a2^*B + a3^*C + a4),$$

wherein a1, a2, a3, and a4 are constant coefficients determined from the trained assessment model, learned using an optimization algorithm that attempts to make this expression maximally correct, and wherein sigmoid is a nonlinear function that enables this expression to be turned into a probability. Such an algorithm can be quick to train, and the resulting expressions can be computed quickly in application, e.g., during administration of the assessment procedure. Although reference is made to four coefficients, as many coefficients as are helpful may be used as will be recognized by a person of ordinary skill in the art.

At step 615, the expected importance of each feature value can be determined based on a combination of the metrics calculated in steps 605 and 610. Based on these two factors, the feature recommendation module can determine the expected utility of the specific feature value in predicting a specific developmental disorder. Although reference is made herein to the determination of expected importance via multiplication, the expected importance can be determined by combining coefficients and parameters in many ways, such as with look up tables, logic, or division, for example.

At step 620, steps 605-615 can be repeated for every possible feature value for each candidate feature. For example, if a particular question has 4 possible answers, the expected importance of each of the 4 possible answers is determined.

At step 625, the total expected importance, or the expected feature importance, of each candidate feature can be determined. The expected feature importance of each feature can be determined by summing the feature value importances of every possible feature value for the feature, as determined in step 620. By thus summing the expected utilities across all possible feature values for a given feature, the feature recommendation module can determine the total expected feature importance of the feature for predicting a specific developmental disorder in response to previous answers.

At step 630, steps 605-625 can be repeated for every candidate feature being considered by the feature recommendation module. The candidate features may comprise a subset of possible features such as questions. Thus, an expected feature importance score for every candidate feature can be generated, and the candidate features can be ranked in order of highest to lowest expected feature importance.

Optionally, in addition to the two factors determined in steps 605 and 610, a third factor may also be taken into account in determining the importance of each feature value. Based on the subject's previously provided feature values, the subject's probability of having one or more of the plurality of developmental disorders can be determined. Such a probability can be determined based on the probability distribution stored in the assessment model, indicating the probability of the subject having each of the plurality of screened developmental disorders based on the feature values provided by the subject. In selecting the next feature to be presented to the subject, the algorithm may be configured to give greater weight to the feature values most important or relevant to predicting the one or more developmental disorders that the subject at hand is most likely to have. For example, if a subject's previously provided feature values indicate that the subject has a higher probability of having either an intellectual disability or speech and language delay than any of the other developmental disorders being evaluated, the feature recommendation module can favor feature values having high importance for predicting either intellectual disability or speech and language delay, rather than features having high importance for predicting autism, ADHD, or any other developmental disorder that the assessment is designed to screen for. The feature recommendation module can thus enable the prediction module to tailor the prediction process to the subject at hand, presenting more features that are relevant to the subject's potential developmental disorder to yield a final classification with higher granularity and confidence.

Although the above steps show an exemplary operational flow 600 of an expected feature importance determination algorithm 127, a person of ordinary skill in the art will recognize many variations based on the teachings described herein. The steps may be completed in a different order. Steps may be added or deleted. Some of the steps may comprise sub-steps of other steps. Many of the steps may be repeated as often as desired by the user.

An exemplary implementation of the feature recommendation module is now described. Subject X has provided answers (feature values) to questions (features) A, B, and C in the assessment procedure:

$$\text{Subject } X = \{`A`:1, `B`:2, `C`:1\}$$

The feature recommendation module can determine whether question D or question E should be presented next in order to maximally increase the predictive confidence with which a final classification or diagnosis can be reached. Given Subject X's previous answers, the feature recommendation module determines the probability of Subject X providing each possible answer to each of questions D and E, as follows:

$$prob(E = 1 | A = 1, B = 2, C = 1) = 0.1$$
$$prob(E = 2 | A = 1, B = 2, C = 1) = 0.9$$

$$prob(D = 1 \mid A = 1, B = 2, C = 1) = 0.7$$
$$prob(D = 2 \mid A = 1, B = 2, C = 1) = 0.3$$

The feature importance of each possible answer to each of questions D and E can be computed based on the assessment model as described. Alternatively, the feature importance of each possible answer to each of questions D and E can be computed as the actual prediction confidence that would result if the subject were to give the specific answer. The importance of each answer can be represented using a range of values on any appropriate numerical scale. For example:

$$\text{importance}(E = 1) = 1$$
$$\text{importance}(E = 2) = 3$$
$$\text{importance}(D = 1) = 2$$
$$\text{importance}(D = 2) = 4$$

Based on the computed probabilities and the feature value importances, the feature recommendation module can compute the expected feature importance of each question as follows:

$$\begin{aligned}\text{Expectation}[\text{importance}(E)] &= prob(E = 1 \mid A = 1, B = 2, C = 1)^* \\ &\quad \text{importance}(E = 1) \\ &\quad + prob(E = 2 \mid A = 1, B = 2, C = 1)^* \\ &\quad \text{importance}(E = 2) \\ &= 0.1^*1 + 0.9^*3 \\ &= 2.8\end{aligned}$$

$$\begin{aligned}\text{Expectation}[\text{importance}(D)] &= prob(D = 1 \mid A = 1, B = 2, C = 1)^* \\ &\quad \text{importance}(D = 1) \\ &\quad + prob(D = 2 \mid A = 1, B = 2, C = 1)^* \\ &\quad \text{importance}(D = 2) \\ &= 0.7^*2 + 0.3^*4 \\ &= 2.6\end{aligned}$$

Hence, the expected feature importance (also referred to as relevance) from the answer of question E is determined to be higher than that of question D, even though question D has generally higher feature importances for its answers. The feature recommendation module can therefore select question E as the next question to be presented to Subject X.

When selecting the next best feature to be presented to a subject, the feature recommendation module 125 may be further configured to exclude one or more candidate features from consideration, if the candidate features have a high co-variance with a feature that has already been presented to the subject. The co-variance of different features may be determined based on the training data, and may be stored in the assessment model constructed by the training module. If a candidate feature has a high co-variance with a previously presented feature, the candidate feature may add relatively little additional predictive utility, and may hence be omitted from future presentation to the subject in order to optimize the efficiency of the assessment procedure.

The prediction module 120 may interact with the person participating in the assessment procedure (e.g., a subject or the subject's caretaker) with a user interface 130. The user interface may be provided with a user interface, such as a display of any computing device that can enable the user to access the prediction module, such as a personal computer, a tablet, or a smartphone. The computing device may comprise a processor that comprises instructions for providing the user interface, for example in the form of a mobile application. The user interface can be configured to display instructions from the prediction module to the user, and/or receive input from the user with an input method provided by the computing device. Thus, the user can participate in the assessment procedure as described herein by interacting with the prediction module with the user interface, for example by providing answers (feature values) in response to questions (features) presented by the prediction module. The user interface may be configured to administer the assessment procedure in real-time, such that the user answers one question at a time and the prediction module can select the next best question to ask based on recommendations made by the feature recommendation module. Alternatively or in combination, the user interface may be configured to receive a complete set of new data from a user, for example by allowing a user to upload a complete set of feature values corresponding to a set of features.

As described herein, the features of interest relevant to identifying one or more developmental disorders may be evaluated in a subject in many ways. For example, the subject or caretaker or clinician may be asked a series of questions designed to assess the extent to which the features of interest are present in the subject. The answers provided can then represent the corresponding feature values of the subject. The user interface may be configured to present a series of questions to the subject (or any person participating in the assessment procedure on behalf of the subject), which may be dynamically selected from a set of candidate questions as described herein. Such a question-and-answer based assessment procedure can be administered entirely by a machine, and can hence provide a very quick prediction of the subject's developmental disorder(s).

Alternatively or in combination, features of interest in a subject may be evaluated with observation of the subject's behaviors, for example with videos of the subject. The user interface may be configured to allow a subject or the subject's caretaker to record or upload one or more videos of the subject. The video footage may be subsequently analyzed by qualified personnel to determine the subject's feature values for features of interest. Alternatively or in combination, video analysis for the determination of feature values may be performed by a machine. For example, the video analysis may comprise detecting objects (e.g., subject, subject's spatial position, face, eyes, mouth, hands, limbs, fingers, toes, feet, etc.), followed by tracking the movement of the objects. The video analysis may infer the gender of the subject, and/or the proficiency of spoken language(s) of the subject. The video analysis may identify faces globally, or specific landmarks on the face such as the nose, eyes, lips and mouth to infer facial expressions and track these expressions over time. The video analysis may detect eyes, limbs, fingers, toes, hands, feet, and track their movements over time to infer behaviors. In some cases, the analysis may further infer the intention of the behaviors, for example, a child being upset by noise or loud music, engaging in self-harming behaviors, imitating another person's actions, etc. The sounds and/or voices recorded in the video files may also be analyzed. The analysis may infer a context of the subject's behavior. The sound/voice analysis may infer a feeling of the subject. The analysis of a video of a subject, performed by a human and/or by a machine, can yield feature values for the features of interest, which can then be encoded appropriately for input into the prediction module. A prediction of the subject's developmental disorder may then be generated based on a fitting of the subject's feature values to the assessment model constructed using training data.

Alternatively or in combination, features of interest in a subject may be evaluated through structured interactions with the subject. For example, the subject may be asked to play a game such as a computer game, and the performance of the subject on the game may be used to evaluate one or more features of the subject. The subject may be presented with one or more stimuli (e.g., visual stimuli presented to the subject via a display), and the response of the subject to the stimuli may be used to evaluate the subject's features. The subject may be asked to perform a certain task (e.g., subject may be asked to pop bubbles with his or her fingers), and the response of the subject to the request or the ability of the subject to carry out the requested task may be used to evaluate to the subject's features.

The methods and apparatus described herein can be configured in many ways to determine the next most predictive or relevant question. At least a portion of the software instructions as described herein can be configured to run locally on a local device so as to provide the user interface and present questions and receive answers to the questions. The local device can be configured with software instructions of an application program interface (API) to query a remote server for the most predictive next question. The API can return an identified question based on the feature importance as described herein, for example. Alternatively or in combination, the local processor can be configured with instructions to determine the most predictive next question in response to previous answers. For example, the prediction module 120 may comprise software instructions of a remote server, or software instructions of a local processor, and combinations thereof. Alternatively or in combination, the feature recommendation module 125 may comprise software instructions of a remote server, or software instructions of a local processor, and combinations thereof, configured to determine the most predictive next question, for example. The exemplary operational flow 600 of method of determining an expected feature importance determination algorithm 127 as performed by a feature recommendation module 125 described herein can be performed with one or more processors as described herein, for example.

Figure 7:
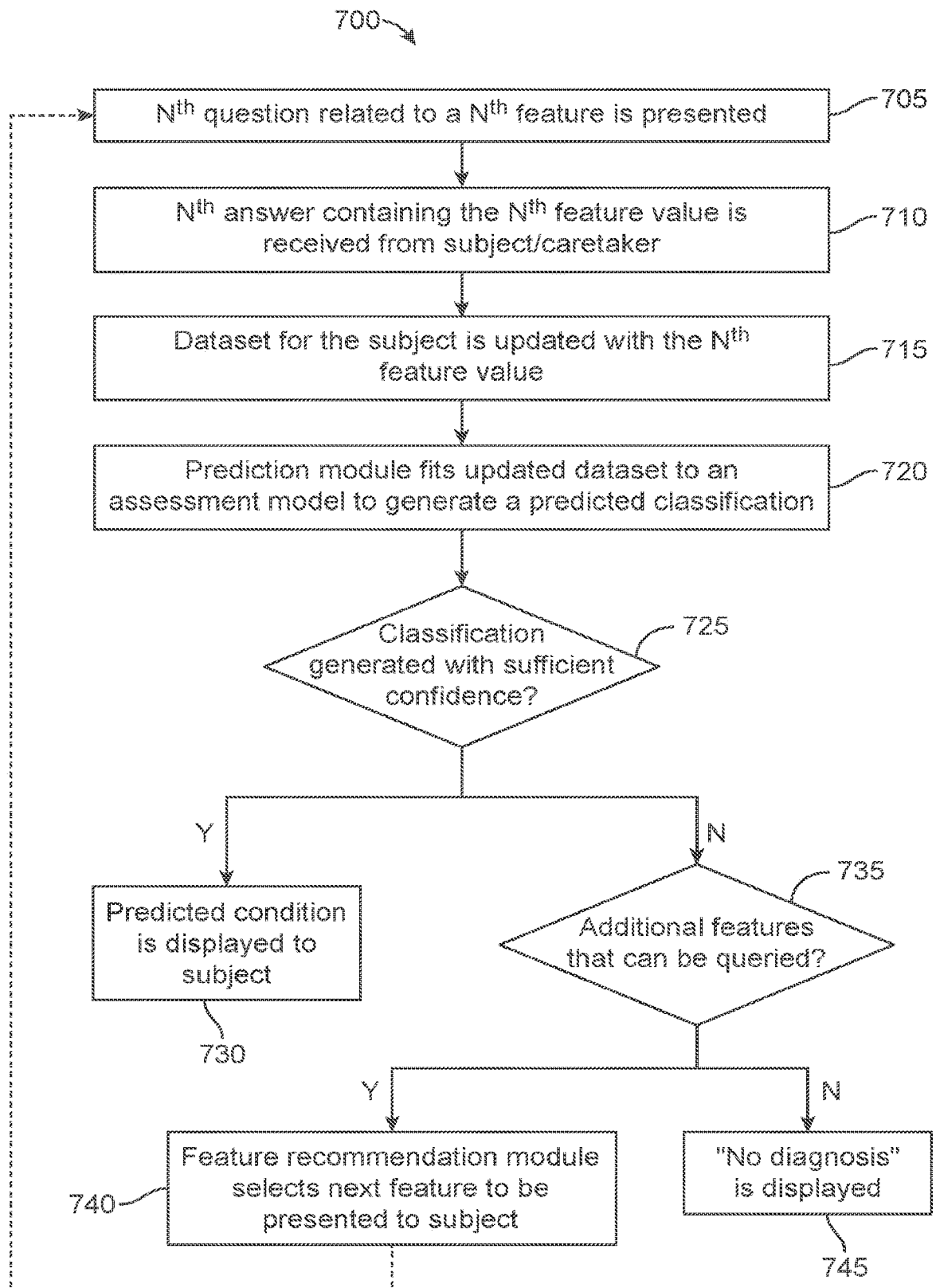
FIG. 7 illustrates a method of administering an assessment procedure as described herein.

FIG. 7 illustrates a method 700 of administering an assessment procedure as described herein. The method 700 may be performed with a user interface provided on a computing device, the computing device comprising a display and a user interface for receiving user input in response to the instructions provided on the display. The user participating in the assessment procedure may be the subject himself, or another person participating in the procedure on behalf of the subject, such as the subject's caretaker. At step 705, an $N^{th}$ question related an $N^{th}$ feature can be presented to the user with the display. At step 710, the subject's answer containing the corresponding $N^{th}$ feature value can be received. At step 715, the dataset for the subject at hand can be updated to include $N^{th}$ the feature value provided for the subject. At step 720, the updated dataset can be fitted to an assessment model to generate a predicted classification. Step 720 may be performed by a prediction module, as described herein. At step 725, a check can be performed to determine whether the fitting of the data can generate a prediction of a specific developmental disorder (e.g., autism, ADHD, etc.) sufficient confidence (e.g., within at least a 90% confidence interval). If so, as shown at step 730, the predicted developmental disorder can be displayed to the user. If not, in step 735, a check can be performed to determine whether there are any additional features that can be queried. If yes, as shown at step 740, the feature recommendation module may select the next feature to be presented to the user, and steps 705-725 may be repeated until a final prediction (e.g., a specific developmental disorder or "no diagnosis") can be displayed to the subject. If no additional features can be presented to the subject, "no diagnosis" may be displayed to the subject, as shown at step 745.

Although the above steps show an exemplary a method 700 of administering an assessment procedure, a person of ordinary skill in the art will recognize many variations based on the teachings described herein. The steps may be completed in a different order. Steps may be added or deleted. Some of the steps may comprise sub-steps of other steps. Many of the steps may be repeated as often as desired by the user.

Figure 8:
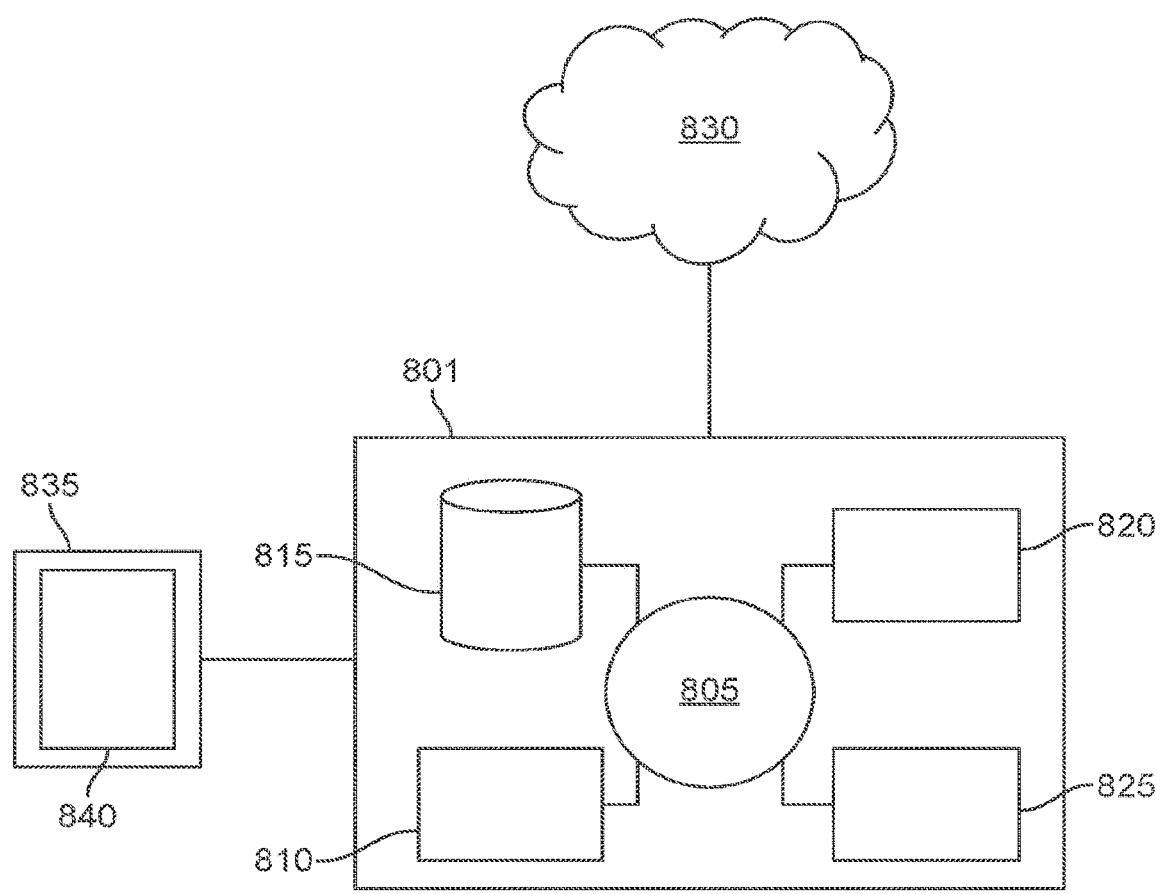
FIG. 8 shows a computer system suitable for incorporation with the methods and apparatus described herein.

The present disclosure provides computer control systems that are programmed to implement methods of the disclosure. FIG. 8 shows a computer system 801 suitable for incorporation with the methods and apparatus described herein. The computer system 801 can process various aspects of information of the present disclosure, such as, for example, questions and answers, responses, statistical analyses. The computer system 801 can be an electronic device of a user or a computer system that is remotely located with respect to the electronic device. The electronic device can be a mobile electronic device.

The computer system 801 includes a central processing unit (CPU, also "processor" and "computer processor" herein) 805, which can be a single core or multi core processor, or a plurality of processors for parallel processing. The computer system 801 also includes memory or memory location 810 (e.g., random-access memory, read-only memory, flash memory), electronic storage unit 815 (e.g., hard disk), communication interface 820 (e.g., network adapter) for communicating with one or more other systems, and peripheral devices 825, such as cache, other memory, data storage and/or electronic display adapters. The memory 810, storage unit 815, interface 820 and peripheral devices 825 are in communication with the CPU 805 through a communication bus (solid lines), such as a motherboard. The storage unit 815 can be a data storage unit (or data repository) for storing data. The computer system 801 can be operatively coupled to a computer network ("network") 830 with the aid of the communication interface 820. The network 830 can be the Internet, an internet and/or extranet, or an intranet and/or extranet that is in communication with the Internet. The network 830 in some cases is a telecommunication and/or data network. The network 830 can include one or more computer servers, which can enable distributed computing, such as cloud computing. The network 830, in some cases with the aid of the computer system 801, can implement a peer-to-peer network, which may enable devices coupled to the computer system 801 to behave as a client or a server.

The CPU 805 can execute a sequence of machine-readable instructions, which can be embodied in a program or software. The instructions may be stored in a memory location, such as the memory 810. The instructions can be directed to the CPU 805, which can subsequently program or otherwise configure the CPU 805 to implement methods of the present disclosure. Examples of operations performed by the CPU 805 can include fetch, decode, execute, and writeback.

The CPU 805 can be part of a circuit, such as an integrated circuit. One or more other components of the system 801 can be included in the circuit. In some cases, the circuit is an application specific integrated circuit (ASIC).

The storage unit 815 can store files, such as drivers, libraries and saved programs. The storage unit 815 can store user data, e.g., user preferences and user programs. The computer system 801 in some cases can include one or more additional data storage units that are external to the computer system 801, such as located on a remote server that is in communication with the computer system 801 through an intranet or the Internet.

The computer system 801 can communicate with one or more remote computer systems through the network 830. For instance, the computer system 801 can communicate with a remote computer system of a user (e.g., a parent). Examples of remote computer systems and mobile communication devices include personal computers (e.g., portable PC), slate or tablet PC's (e.g., Apple® iPad, Samsung® Galaxy Tab), telephones, Smart phones (e.g., Apple® iPhone, Android-enabled device, Blackberry®), or personal digital assistants. The user can access the computer system 801 with the network 830.

Methods as described herein can be implemented by way of machine (e.g., computer processor) executable code stored on an electronic storage location of the computer system 801, such as, for example, on the memory 810 or electronic storage unit 815. The machine executable or machine readable code can be provided in the form of software. During use, the code can be executed by the processor 805. In some cases, the code can be retrieved from the storage unit 815 and stored on the memory 810 for ready access by the processor 805. In some situations, the electronic storage unit 815 can be precluded, and machine-executable instructions are stored on memory 810.

The code can be pre-compiled and configured for use with a machine have a processer adapted to execute the code, or can be compiled during runtime. The code can be supplied in a programming language that can be selected to enable the code to execute in a pre-compiled or as-compiled fashion.

Aspects of the systems and methods provided herein, such as the computer system 801, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 801 can include or be in communication with an electronic display 835 that comprises a user interface (UI) 840 for providing, for example, questions and answers, analysis results, recommendations. Examples of UI's include, without limitation, a graphical user interface (GUI) and web-based user interface.

Methods and systems of the present disclosure can be implemented by way of one or more algorithms and with instructions provided with one or more processors as disclosed herein. An algorithm can be implemented by way of software upon execution by the central processing unit 805. The algorithm can be, for example, random forest, graphical models, support vector machine or other.

Although the above steps show a method of a system in accordance with an example, a person of ordinary skill in the art will recognize many variations based on the teaching described herein. The steps may be completed in a different order. Steps may be added or deleted. Some of the steps may comprise sub-steps. Many of the steps may be repeated as often as if beneficial to the platform.

Each of the examples as described herein can be combined with one or more other examples. Further, one or more components of one or more examples can be combined with other examples.

Experimental Data

A data processing module as described herein was built on Python 2.7, Anaconda Distribution. The training data used to construct and train the assessment model included data generated by the Autism Genetic Resource Exchange (AGRE), which performed in-home assessments to collect ADI-R and ADOS data from parents and children in their homes. ADI-R comprises a parent interview presenting a total of 93 questions, and yields a diagnosis of autism or no autism. ADOS comprises a semi-structured interview of a child that yields a diagnosis of autism, ASD, or no diagnosis, wherein a child is administered one of four possible modules based on language level, each module comprising about 30 questions. The data included clinical diagnoses of the children derived from the assessments; if a single child had discrepant ADI-R versus ADOS diagnoses, a licensed clinical psychologist assigned a consensus diagnosis for the dataset for the child in question. The training data included a total of 3,449 data points, with 3,315 cases (autism or ASD) and 134 controls (non-spectrum). The features evaluated in the training data targeted 3 key domains: language, social communication, and repetitive behaviors.

A boosted Random Forest classifier was used to build the assessment model as described herein. Prior to training the assessment model on the training data, the training data was pre-processed to standardize the data, and re-encode categorical features in a one-hot representation as described herein. Since the training data was skewed towards individuals with autism or ASD, sample weighting was applied to attribute up to 50 times higher significance to data from non-spectrum individuals compared to data from autistic/ASD individuals. The assessment model was trained iteratively with boosting, updating the weighting of data points after each iteration to increase the significance attributed to data points that were misclassified, and retraining with the updated significances.

Figure 9:
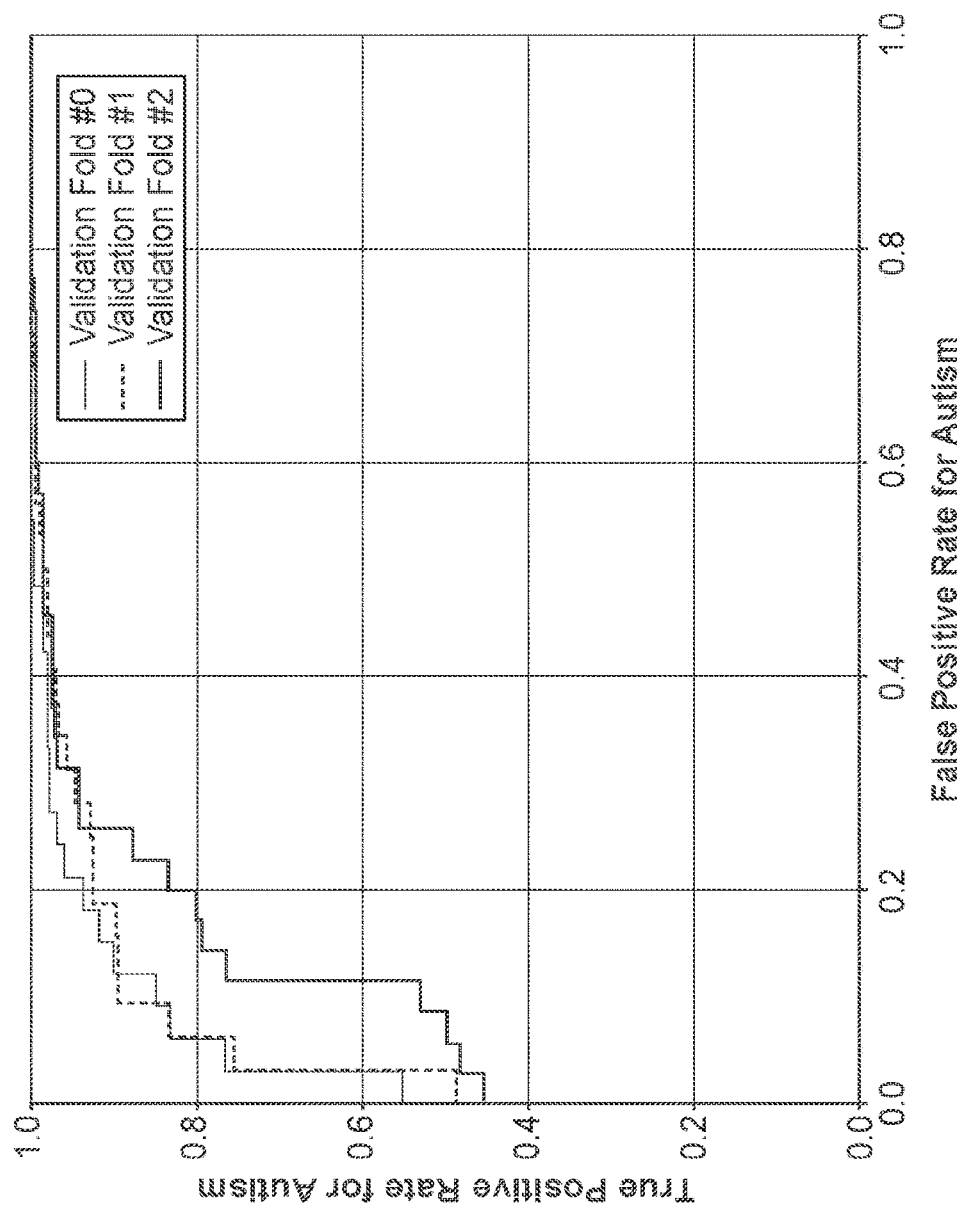
FIG. 9 shows receiver operating characteristic (ROC) curves mapping sensitivity versus fall-out for an exemplary assessment model as described herein.

The trained model was validated using Stratified k-fold cross validation with k=5. The cross-validation yielded an accuracy of about 93-96%, wherein the accuracy is defined as the percentage of subjects correctly classified using the model in a binary classification task (autism/non-spectrum). Since the training data contained a sample bias, a confusion matrix was calculated to determine how often the model confused one class (autism or non-spectrum) with another. The percentage of correctly classified autism individuals was about 95%, while the percentage of correctly classified non-spectrum individuals was about 76%. It should be noted, however, that the model may be adjusted to more closely fit one class versus another, in which case the percentage of correct classifications for each class can change. FIG. 9 shows receiver operating characteristic (ROC) curves mapping sensitivity versus fall-out for an exemplary assessment model as described herein. The true positive rate (sensitivity) for the diagnosis of autism is mapped on the y-axis, as a function of the false positive rate (fall-out) for diagnosis mapped on the x-axis. Each of the three curves, labeled "Fold #0", "Fold #1", and "Fold #2", corresponds to a different "fold" of the cross-validation procedure, wherein for each fold, a portion of the training data was fitted to the assessment model while varying the prediction confidence threshold necessary to classify a dataset as "autistic". As desired or appropriate, the model may be adjusted to increase the sensitivity in exchange for some increase in fall-out, or to decrease the sensitivity in return for a decrease in fall-out, as according to the ROC curves of the model.

Figure 10:
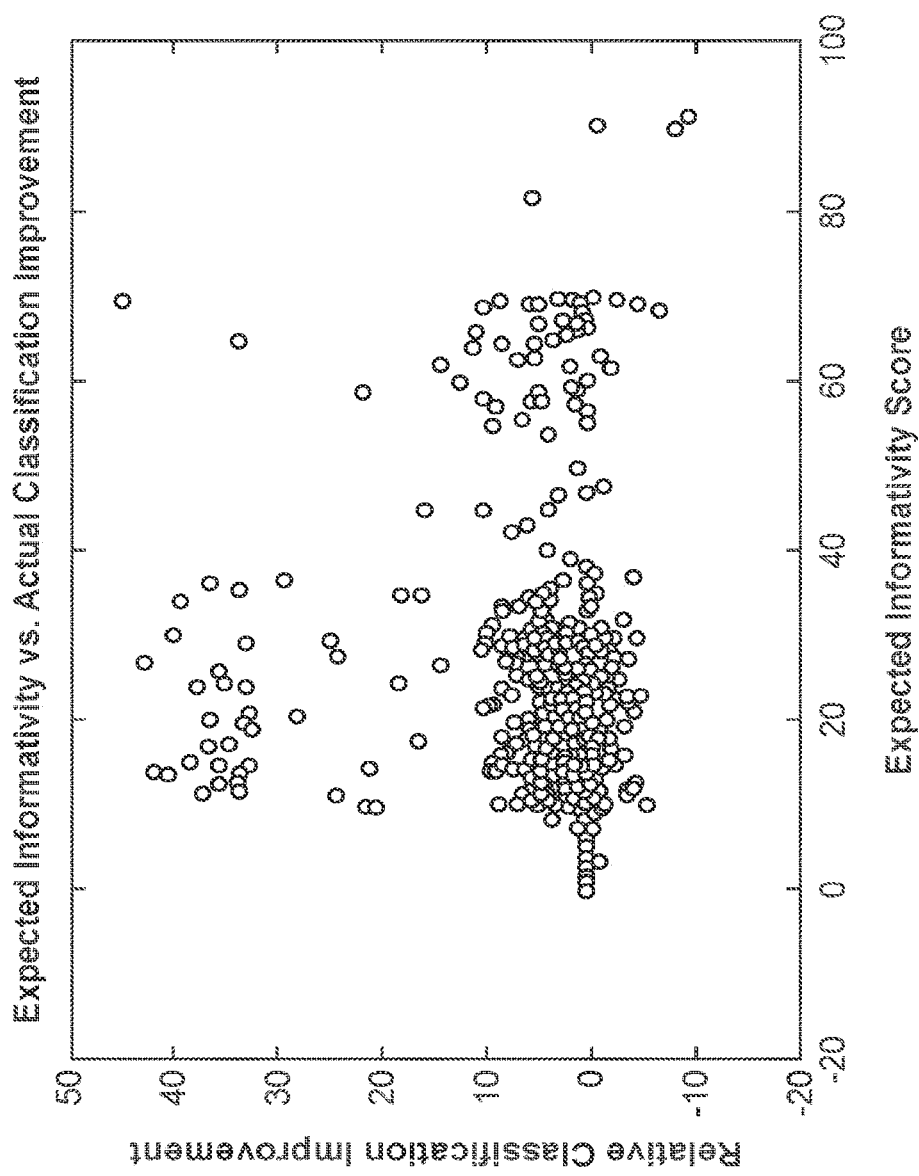
FIG. 10 is a scatter plot illustrating a performance metric for a feature recommendation module as described herein.

The feature recommendation module was configured as described herein, wherein the expected feature importance of each question was computed, and candidate questions ranked in order of computed importance with calls to a server with an application program interface (API). The feature recommendation module's ability to recommend informative questions was evaluated by determining the correlation between a question's recommendation score with the increase in prediction accuracy gained from answering the recommended question. The following steps were performed to compute the correlation metric: (1) the data was split up into folds for cross-validation; (2) already answered questions were randomly removed from the validation set; (3) expected feature importance (question recommendation/score) was generated for each question; (4) one of the questions removed in step 2 was revealed, and the relative improvement in the subsequent prediction accuracy was measured; and (5) the correlation between the relative improvement and the expected feature importance was computed. The calculated Pearson correlation coefficient ranged between 0.2 and 0.3, indicating a moderate degree of correlation between the expected feature importance score and the relative improvement. FIG. 10 is a scatter plot showing the correlation between the expected feature importance ("Expected Informativitiy Score") and the relative improvement ("Relative Classification Improvement") for each question. The plot shows a moderate linear relationship between the two variables, demonstrating the feature recommendation module is indeed able to recommend questions that would increase the prediction accuracy.

The length of time to produce an output using the developed prediction module and the feature recommendation model was measured. The prediction module took about 46 ms to make a prediction of an individual's risk of autism. The feature recommendation module took about 41 ms to generation question recommendations for an individual. Although these measurements were made with calls to a server through an API, the computations can be performed locally, for example.

While the assessment model of the data processing module described with respect to FIGS. 9-10 was constructed and trained to classify subjects as having autism or no autism, a similar approach may be used to build an assessment model that can classify a subject as having one or more of a plurality of developmental disorders, as described herein.

In another aspect, the methods and apparatus disclosed herein can identify a subject as belonging to one of three categories: having a developmental condition, being developmentally normal or typical, or inconclusive or requiring additional evaluation to determine whether the subject has the developmental condition. The developmental condition can be a developmental disorder or a developmental advancement. The addition of the third category, namely the inconclusive determination, results in improved performance and better accuracy of the categorical evaluations corresponding to the presence or absence of a developmental condition.

Figure 11:
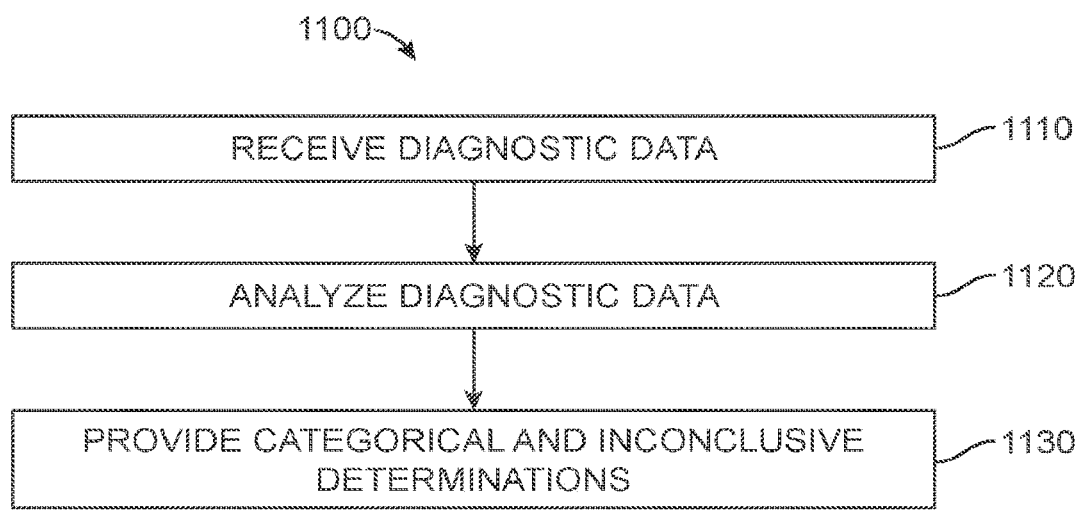
FIG. 11 is an exemplary operational flow of an evaluation module as described herein.

FIG. 11 is an exemplary operational flow of an evaluation module identifying a subject as belonging to one of three categories. As shown in FIG. 11, a method 1100 is provided for evaluating at least one behavioral developmental condition of a subject. The evaluation module receives diagnostic data of the subject related to the behavioral developmental at 1110, evaluates the diagnostic data at 1120 using a selected subset of a plurality of machine learning assessment models and provides categorical determinations for the subject at 1130. The categorical determination can be inconclusive, or can indicate the presence or absence of the behavioral developmental condition.

Figure 12:
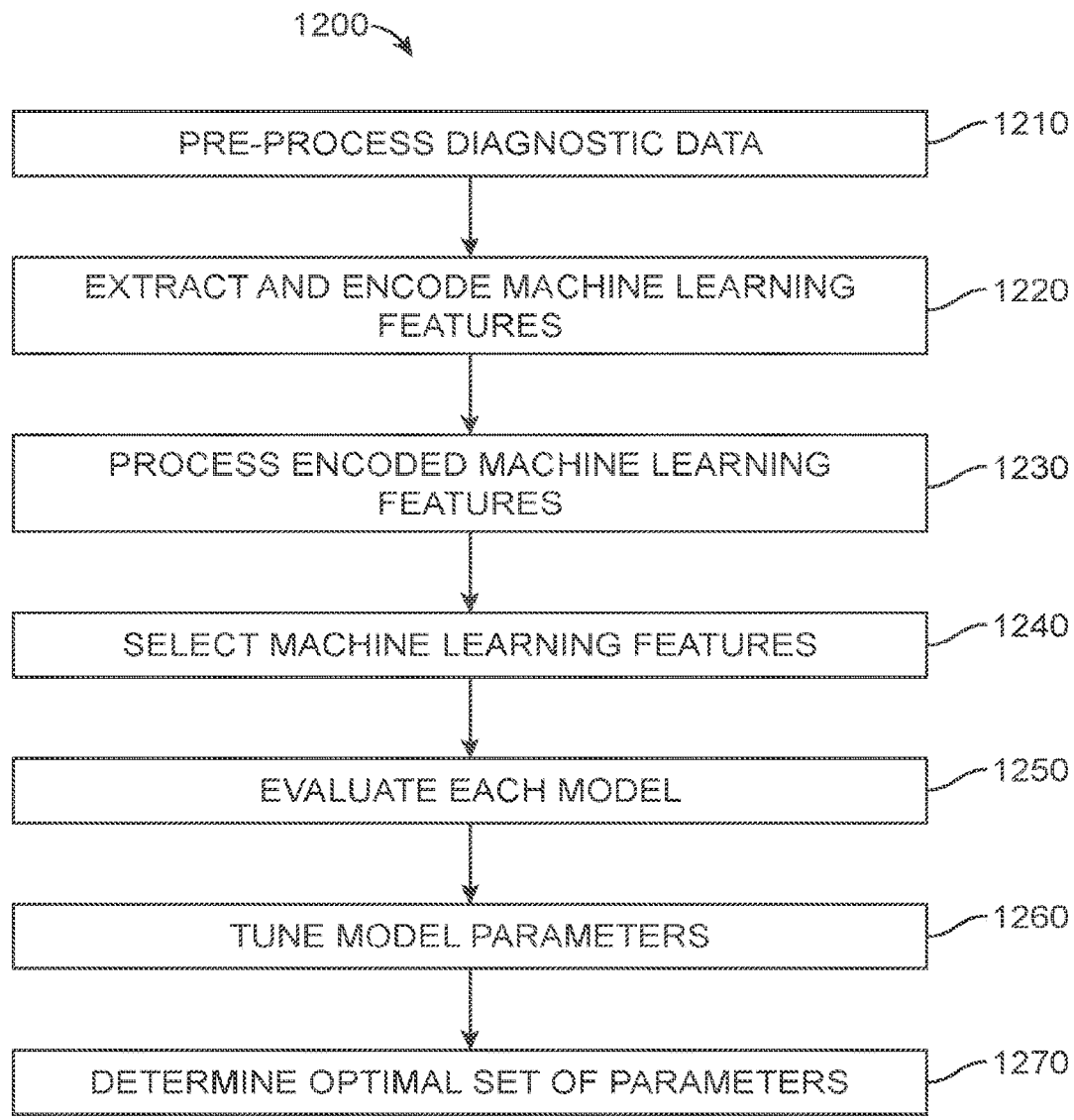
FIG. 12 is an exemplary operational flow of a model tuning module as described herein.

FIG. 12 is an exemplary operational flow of a model training module as described herein. As shown in FIG. 12, a method 1200 is provided for using machine learning to train an assessment model and tune its configuration parameters optimally. Multiple machine learning predictive models can be trained and tuned using the method 1200, each using datasets prepared offline and comprising a representative sample of a standardized clinical instrument such as ADI-R, ADOS, or SRS. Models can also be trained using datasets comprising data other than clinical instruments, such as demographic data. The model training module pre-processes diagnostic data from a plurality of subjects using machine learning techniques at 1210. Datasets can be pre-processed using well-established machine learning techniques such as data cleaning, filtering, aggregation, imputation, normalization, and other machine learning techniques as known in the art.

The model training module extracts and encodes machine learning features from the pre-processed diagnostic data at 1220. Columns comprising the datasets can be mapped into machine learning features using feature encoding techniques such as, for example, one-hot encoding, severity encoding, presence-of-behavior encoding or any other feature encoding technique as known in the art. Some of these techniques are novel in nature and not commonly used in machine learning applications, but they are advantageous in the present application because of the nature of the problem at hand, specifically because of the discrepancy between the setting where clinical data is collected and the intended setting where the model will be applied.

Presence of behavior encoding in particular is advantageous for the problem at hand especially, since the machine learning training data is comprised of clinical questionnaires filled by psycho-metricians having observed subjects for multiple hours. The answer codes they fill in can correspond to subtle levels of severity or differences in behavioral patterns that may only become apparent throughout the long period of observation. This data is then used to train models destined to be applied in a setting where only a few minutes of subject observation is available. Hence the subtleties in behavioral patterns are expected to be less often noticeable. Presence of behavioral encoding as described herein mitigates this problem by abstracting away the subtle differences between the answer choices and extracting data from the questionnaires only at the level of granularity that is expected to be reliably attained in the application setting.

The model training module processes the encoded machine learning features at 1230. In an exemplary embodiment, questionnaire answers can be encoded into machine learning features, after which, a sample weight can be computed and assigned to every sample of diagnostic data in a dataset, each sample corresponding to each subject having diagnostic data. Samples can be grouped according to subject-specific dimensions and sample weights can be computed and assigned to balance one group of samples against every other group of samples to mirror the expected distribution of subjects in an intended setting. For example, samples with positive classification labels might be balanced against those with negative classification labels. Alternatively or additionally, samples in each of multiple age group bins can be made to amount to an equal total weight. Additional sample balancing dimensions can be used such as gender, geographic region, sub-classification within the positive or negative class, or any other suitable dimension.

The process of sample-weight adjustment might be further refined to mirror the expected distribution of subjects in the intended application setting. This can allow the trained models to be adapted to various specific application settings. For example, a model can be trained for use specifically as a level two screening tool by adjusting the sample weights in the training dataset to reflect the expected prevalence rates of diagnostic conditions in a level two diagnostic clinic. Another variant of the same screener can be trained for use as a general public screening tool, again by adjusting the weights of training samples to reflect and expected population of mostly neuro-typical subjects and a minority of positive samples with prevalence rates to match those in the general population. to mirror an expected distribution of subjects in an intended application setting.

The model training module selects a subset of the processed machine learning features at 1240. In an exemplary embodiment, with the training samples weighted accordingly, and all potential machine learning features encoded appropriately, feature selection can take place using a machine learning process generally known as bootstrapping, where multiple iterations of model training can be run, each using a random subsample of the training data available. After each run, a tally can be updated with the features the training process deemed necessary to include in the model. This list can be expected to vary from run to run, since the random data subsets used in training might contain apparent patterns that are incidental to the choice of data samples and not reflective of real life patterns for the problem at hand. Repeating this process multiple times can allow for the incidental patterns to cancel out, revealing the features that are reflective of patterns that can be expected to generalize well outside the training dataset and into the real world. The top features of the bootstrapping runs can then be selected and used exclusively for training the final model, which is trained using the entire training dataset, and saved for later application.

Several models can be trained instead of one model, in order to specialize the models over a demographic dimension in situations where the dimension is expected to affect the choice of useful features. For example, multiple questionnaire-based models can be built, each for a specific age group, since the best questions to ask of a subject are expected to be different for each age group. In this case, only the right model for each subject is loaded at application time.

The model training module evaluates each model at 1250. In particular, each model can be evaluated for performance, for example, as determined by sensitivity and specificity for a pre-determined inclusion rate. In an exemplary embodiment, using a held-out dataset that was not used during the model training phase, the models can be evaluated for performance, in terms of inclusion rate, sensitivity, and specificity.

The model training module tunes each model at 1260. More specifically, to assess the performance of the models in different tuning settings, the tuning parameters of each model can be changed in iterative increments and the same metrics can be computed over the same held-out set in every iteration. The optimal settings can then be locked in and the corresponding models saved. Tuning parameters can include, for example, the number of trees in a boosted decision tree model, the maximum depth of every tree, the learning rate, the threshold of positive determination score, the range of output deemed inconclusive, and any other tuning parameter as known in the art.

In a preferable embodiment, the parameter tuning process of 1260 can comprise a brute-force grid search, an optimized gradient descent or simulated annealing, or any other space exploration algorithm as known in the art. The models being tuned can undergo separate, independent tuning runs, or alternatively the models can be tuned in an ensemble fashion, with every parameter of every model explored in combination, in order to arrive at the optimal overall set of parameters at 1270 to maximize the benefit of using all the models in an ensemble.

Moreover, in yet another aspect, tuning the inconclusive range of each predictive model can be augmented with an external condition, determined by a business need rather than a performance metric. For example, it can be deemed necessary for a particular classifier to have an inclusion rate of no less than 70%. In other words, the classifier would be expected to provide an evaluation indicating either the presence or the absence of a developmental condition for at least 70% of the subjects being classified, yielding an inconclusive determination for less than 30% of the subjects. Accordingly, the corresponding tuning process for the inconclusive output range would have to be limited to only the ranges where this condition is met.

The models are tunable based on the context of the application. The predictive model can be configured to output a diagnosis having a particular degree of certainty that can be adjusted based on tuning of the inconclusive range.

In addition, tuning of the inconclusive range can be exposed outside the offline machine learning phase. More specifically, tuning of the inconclusive range can be a configurable parameter accessible to agents operating the models after deployment. In this way, it is possible for an operator to dial the overall system up or down along the tradeoff between more inclusion and more accuracy. To support this case, multiple optimal inconclusive ranges might be explored and stored during the model training phase, each with its corresponding inclusion rate. The agent can then affect that change by selecting an optimal point from a menu of previously determined optimal settings.

Figure 13:
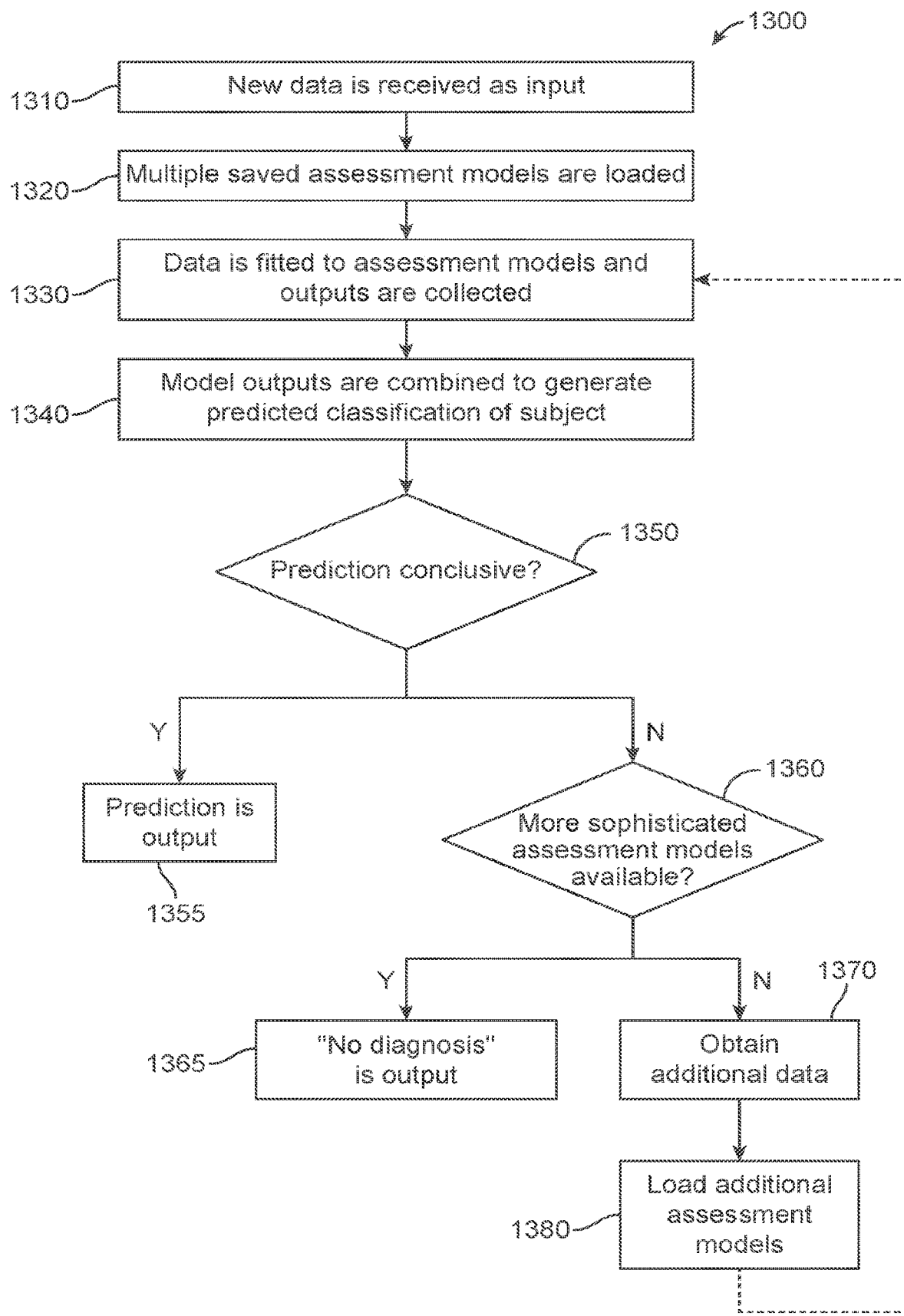
FIG. 13 is another exemplary operational flow of an evaluation module as described herein.

FIG. 13 is another exemplary operational flow of an evaluation module as described herein. As shown in FIG. 13, a method 1300 is provided for outputting a conclusive prediction at 1355 indicating the presence or absence of a developmental condition, or an inconclusive determination of "No diagnosis" at 1365.

The evaluation module as depicted in FIG. 13 receives new data such as diagnostic data from or associated with a subject to be evaluated as having or not having a developmental condition at 1310. Multiple saved assessment models that have been trained, tuned, and optimized as depicted in FIG. 12 and as described herein can be loaded at 1320. Diagnostic data can be fit to these initial assessment models and outputs can be collected at 1330. The evaluation module can combine the initial assessment model outputs at 1340 to generate a predicted initial classification of the subject. If the evaluation module determines that the initial prediction is conclusive at 1350, it can output a conclusive determination indicating either the presence or absence of the developmental condition in the subject. If the evaluation module determines that the initial prediction is inconclusive at 1350, it can then proceed to determine whether additional or more sophisticated assessment models are available and applicable at 1360. If no additional assessment models are available or applicable, the evaluation module outputs an inconclusive determination of "No diagnosis." If however, the evaluation module determines that additional or more sophisticated assessment models are available and applicable, it can proceed to obtain additional diagnostic data from or associated with the subject at 1370. Next, the evaluation module can load the additional or more sophisticated assessment models at 1380 and can repeat the process of fitting data to the models, only this time, the additional data obtained at 1370 is fitted to the additional assessment models loaded at 1380 to produce new model outputs, which are then evaluated at 1350 for a conclusive prediction. This process as depicted by the loop comprising steps 1350, 1355, 1360, 1365, 1370, 1380 and back to 1330 and 1340 can be repeated until either a conclusive prediction is output at 1355, or if no more applicable classification models are available to use, an inconclusive determination of "No diagnosis" is output at 1365.

In particular, when data from a new subject is received as input at 1310 in FIG. 13, each available model for preliminary determination is loaded at 1320 and run, outputting a numerical score at 1330. The scores can then be combined using a combinatorial model.

Figure 14:
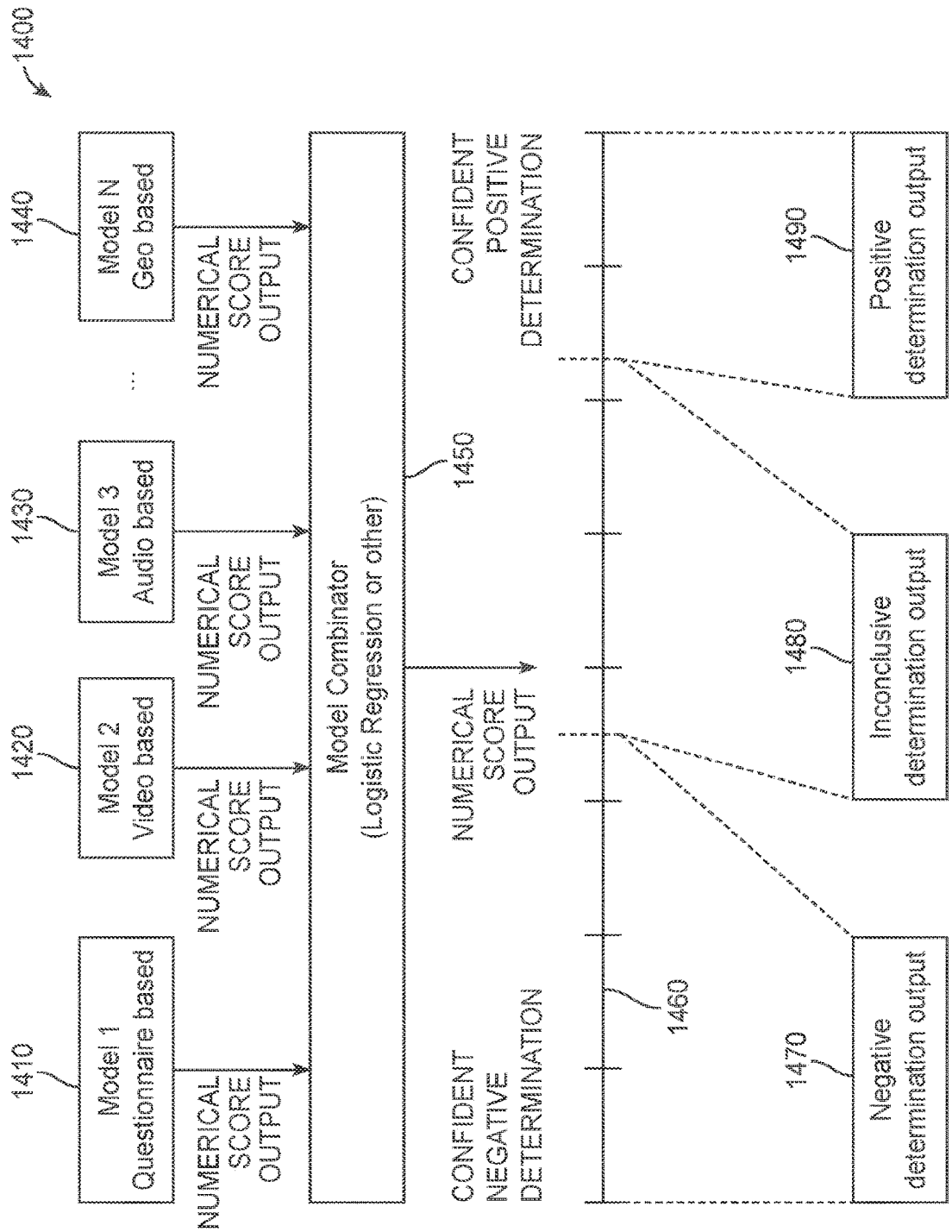
FIG. 14 is an exemplary operational flow of the model output combining step depicted in FIG. 13.

FIG. 14 is an exemplary operational flow of the model output combining step depicted in FIG. 13. As shown in FIG. 14, a combiner module 1400 can collect the outputs from multiple assessment models 1410, 1420, 1430, and 1440, which are received by a model combinatory or combinatorial model 1450. The combinatorial model can employ simple rule-based logic to combine the outputs, which can be numerical scores. Alternatively, the combinatorial model can use more sophisticated combinatorial techniques such as logistic regression, probabilistic modeling, discriminative modeling, or any other combinatorial technique as known in the art. The combinatorial model can also rely on context to determine the best way to combine the model outputs. For example, it can be configured to trust the questionnaire-based model output only in a certain range, or to defer to the video-based model otherwise. In another case, it can use the questionnaire-based model output more significantly for younger subjects than older ones. In another case, it can exclude the output of the video-based model for female subjects, but include the video-based model for male subjects.

The combinatorial model output score can then be subjected to thresholds determined during the model training phase as described herein. In particular, as shown in FIG. 14, these thresholds are indicated by the dashed regions that partition the range of numerical scores 1460 into three segments corresponding to a negative determination output 1470, an inconclusive determination output 1480, and a positive determination output 1490. This effectively maps the combined numerical score to a categorical determination, or to an inconclusive determination if the output is within the predetermined inconclusive range.

In the case of an inconclusive output, the evaluation module can determine that additional data should be obtained from the subject in order to load and run additional models beyond the preliminary or initial set of models. The additional models might be well suited to discern a conclusive output in cases where the preliminary models might not. This outcome can be realized by training additional models that are more sophisticated in nature, more demanding of detailed input data, or more focused on the harder-to-classify cases to the exclusion of the straightforward ones.

Figure 15:
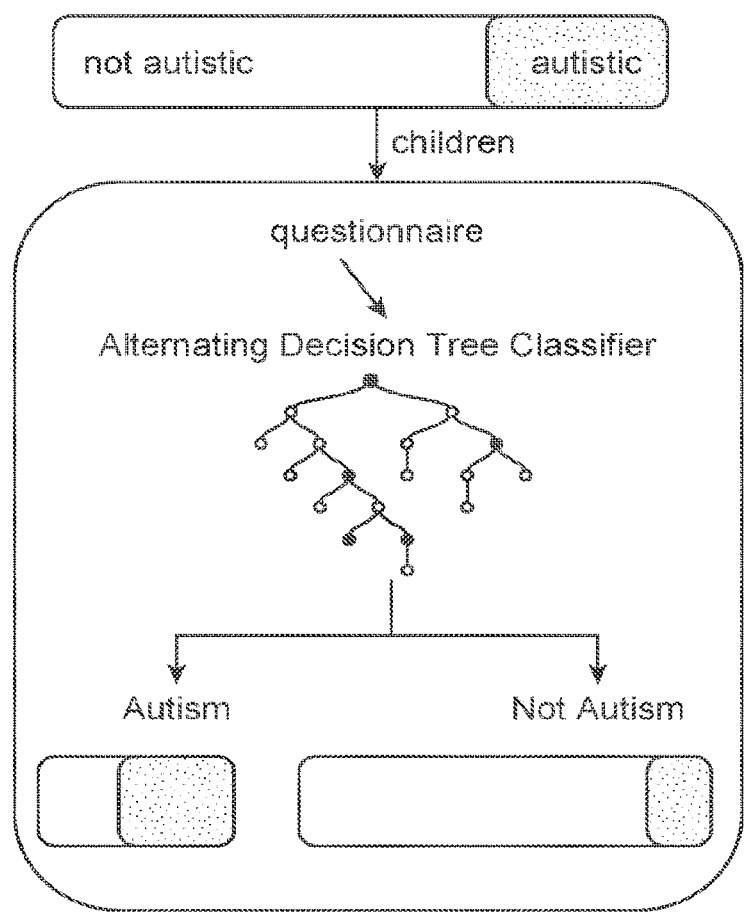
FIG. 15 shows an exemplary questionnaire screening algorithm configured to provide only categorical determinations as described herein.

FIG. 15 shows an exemplary questionnaire screening algorithm configured to provide only categorical determinations of a developmental condition as described herein. In particular, the questionnaire screening algorithm depicted in FIG. 15 shows an alternating decision tree classifier that outputs a determination indicating only the presence or the absence of autism. The different shading depicts the total population of children who are autistic and not autistic and who are evaluated via the questionnaire. Also depicted are the results of the classifier, showing the correctly and incorrectly diagnosed children populations for each of the two categorical determinations.

Figure 16:
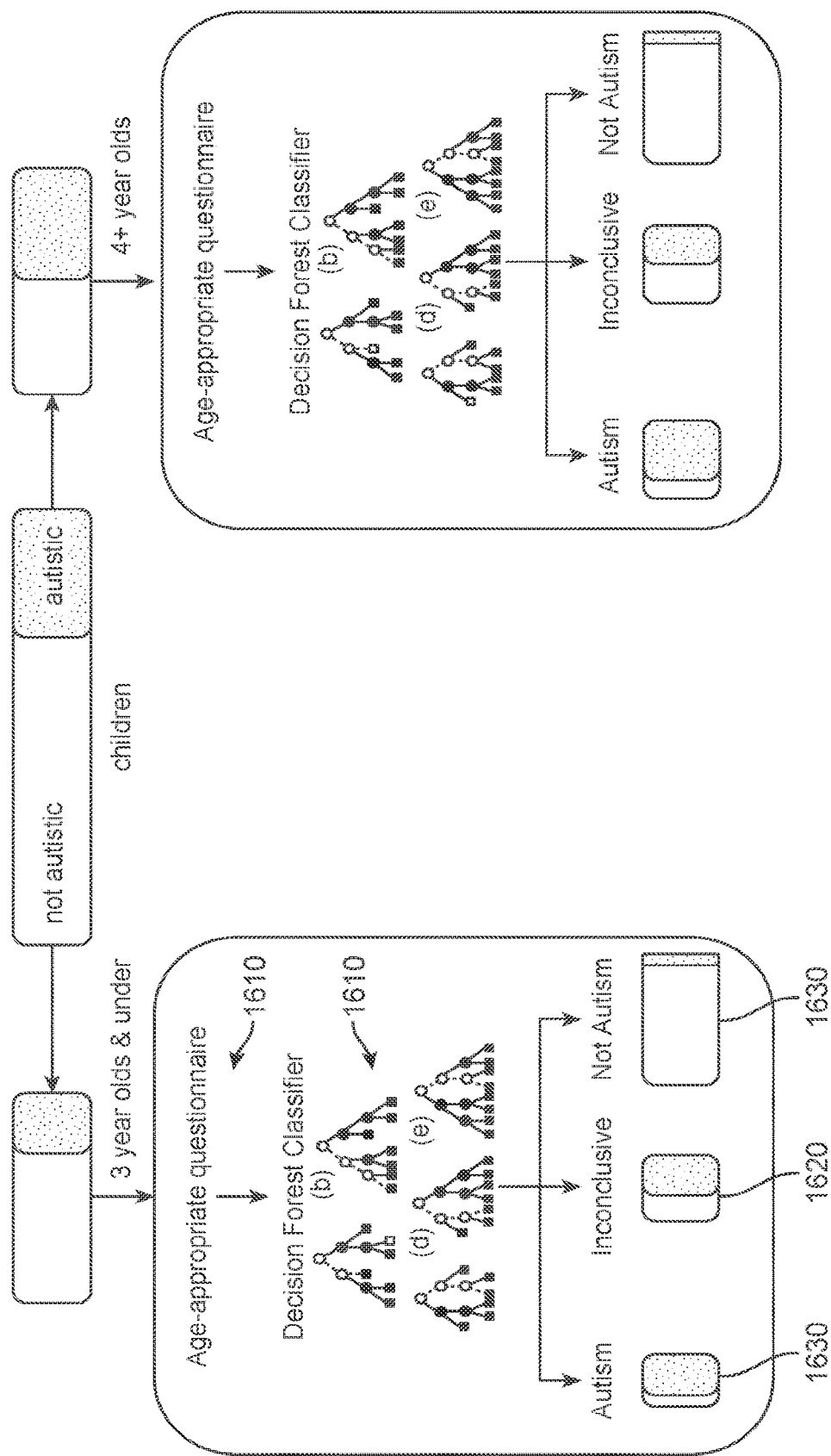
FIG. 16 shows an exemplary questionnaire screening algorithm configured to provide categorical and inconclusive determinations as described herein.

In contrast, FIG. 16 shows an exemplary Triton questionnaire screening algorithm configured to provide both categorical and inconclusive determinations as described herein. In particular, the Triton algorithm depicted in FIG. 16 implements both age-appropriate questionnaires and age-specific models to yield specialized classifiers for each of two subgroups (i.e. "3 years old & under" and "4+ year olds") within a relevant age group (i.e. "children"). It is clear from this example that the categorical determinations indicating the presence and absence of Autism in the two subgroups in FIG. 16 each have a higher accuracy when compared with the categorical determinations in FIG. 15, as indicated by the different shaded areas showing the correctly and incorrectly diagnosed children populations for each of the two categorical determinations. By providing a separate category for inconclusive determinations, the Triton algorithm of FIG. 16 is better able to isolate hard-to-screen cases that result in inaccurate categorical determinations as seen in FIG. 15.

Figure 17:
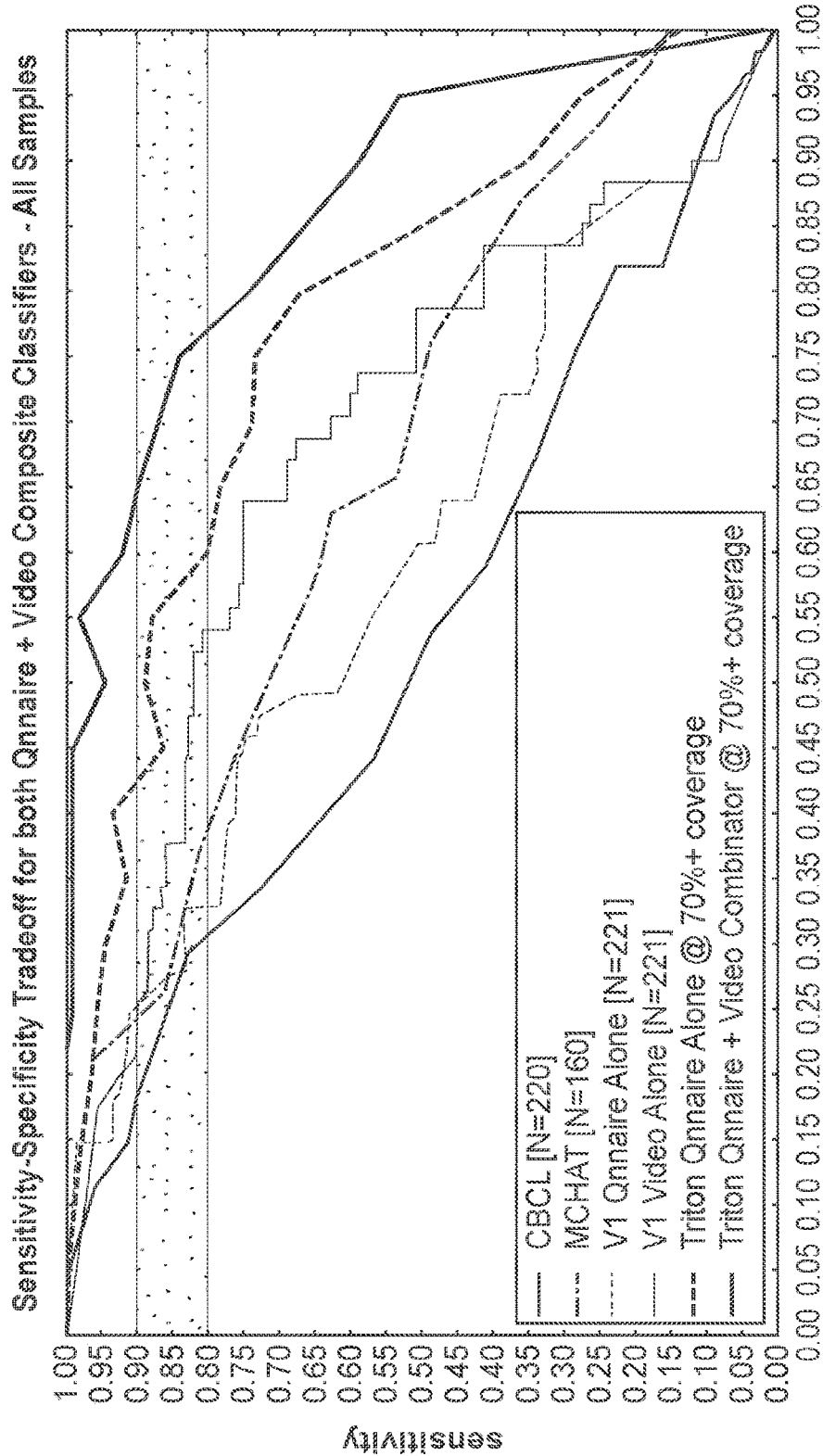
FIG. 17 shows a comparison of the performance for various algorithms for all samples as described herein.

A comparison of the performance for various algorithms highlights the advantages of the Triton algorithm, and in particular, the Triton algorithm having a context-dependent combination of questionnaire and video inputs. FIG. 17 shows a comparison of the performance for various algorithms in terms of a sensitivity-specificity tradeoff for all samples in a clinical sample as described herein. As shown in FIG. 17, the best performance in terms of both sensitivity and specificity is obtained by the Triton algorithm configured for 70% coverage when combined with the video combinator (i.e. context-dependent combination of questionnaire and video inputs).

Figure 18:
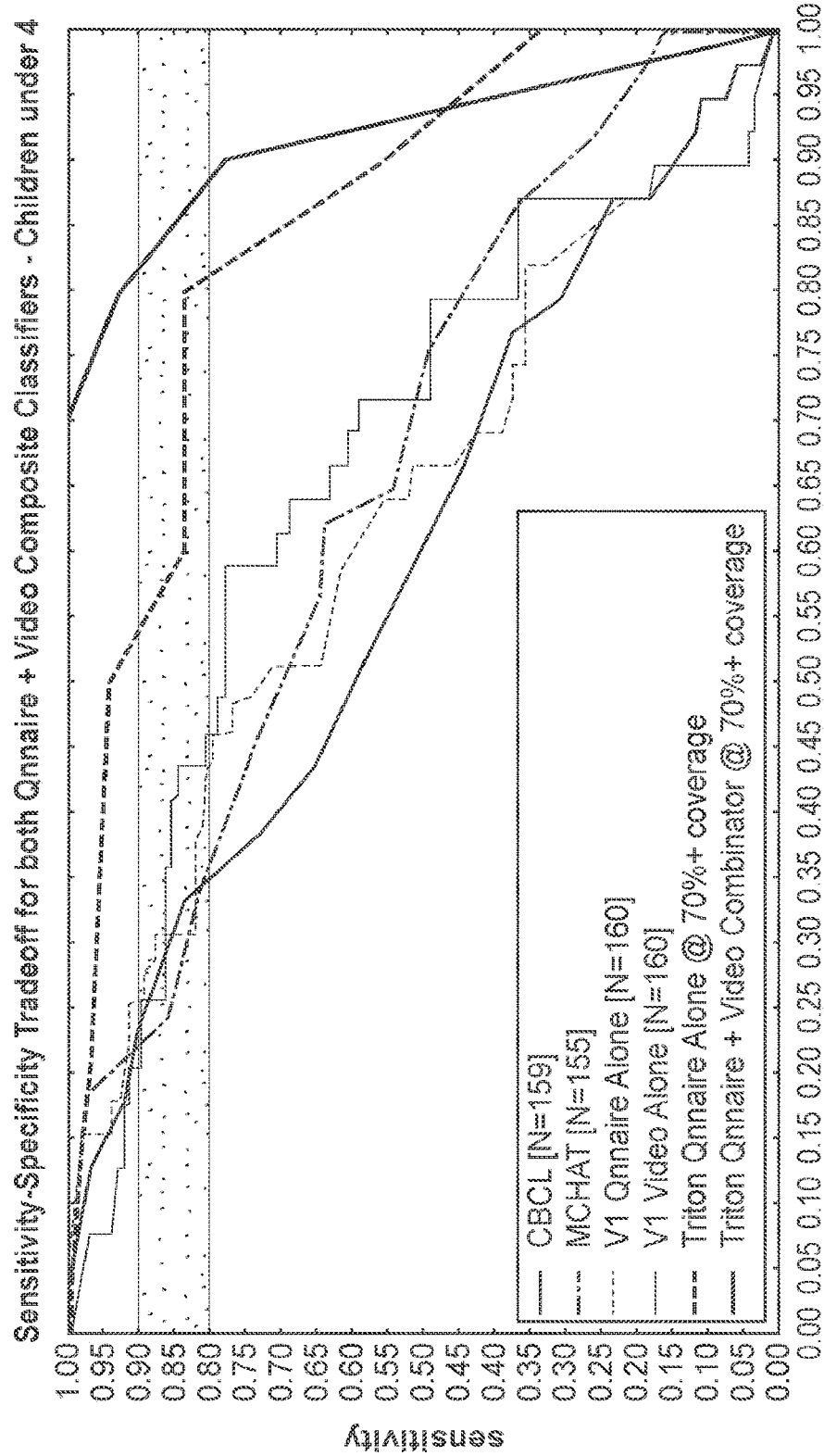
FIG. 18 shows a comparison of the performance for various algorithms for samples taken from Children Under 4 as described herein.

FIG. 18 shows a comparison of the performance for various algorithms in terms of a sensitivity-specificity tradeoff for samples taken from children under 4 as described herein. The Triton algorithm configured for 70% coverage when combined with the video combinator (i.e. context-dependent combination of questionnaire and video inputs) has the best performance.

Figure 19:
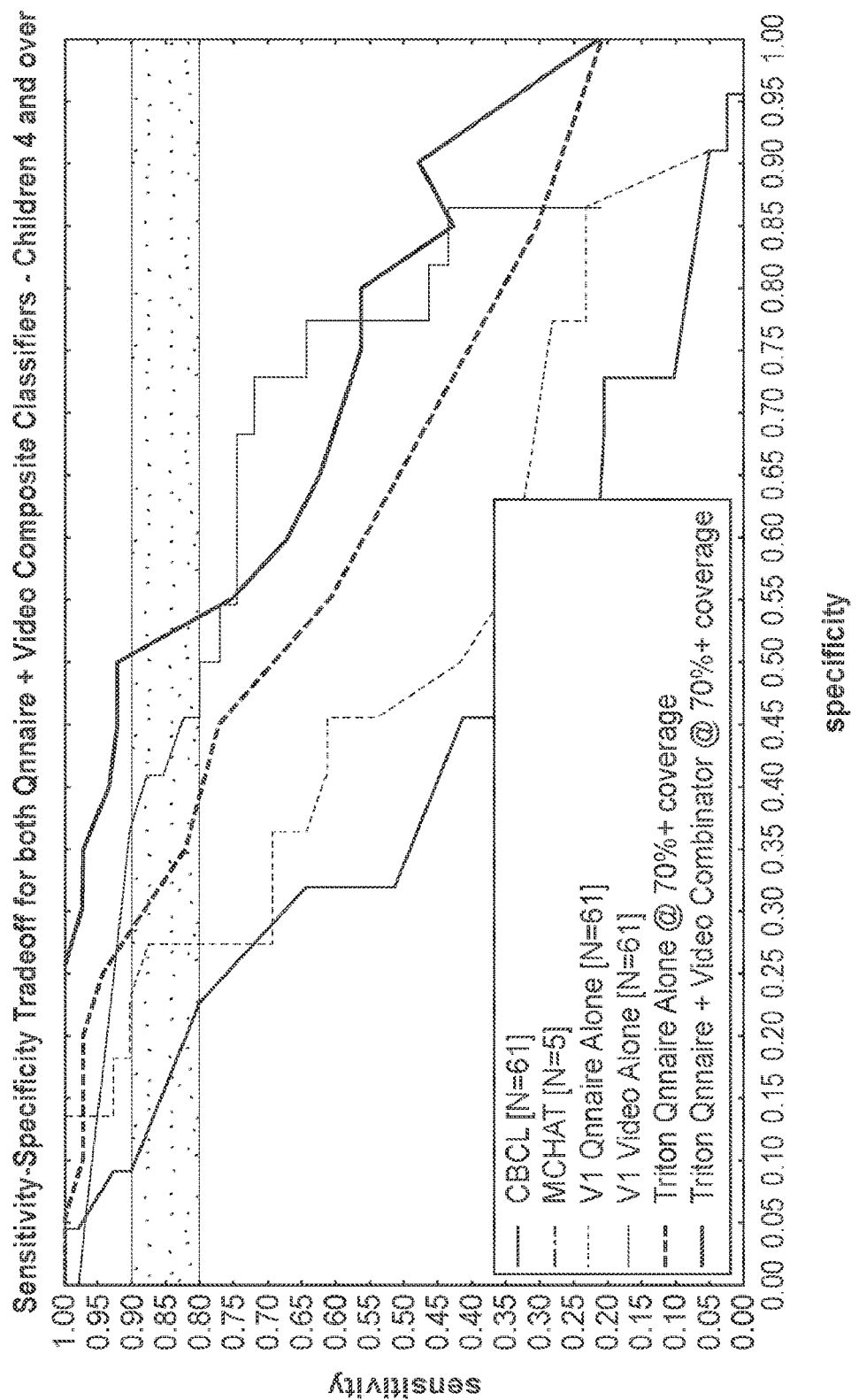
FIG. 19 shows a comparison of the performance for various algorithms for samples taken from Children 4 and Over described herein.

FIG. 19 shows a comparison of the performance for various algorithms in terms of a sensitivity-specificity tradeoff for samples taken from children 4 and over described herein. For the most part, the Triton algorithm configured for 70% coverage when combined with the video combinator appears to have the best performance.

Figure 20:
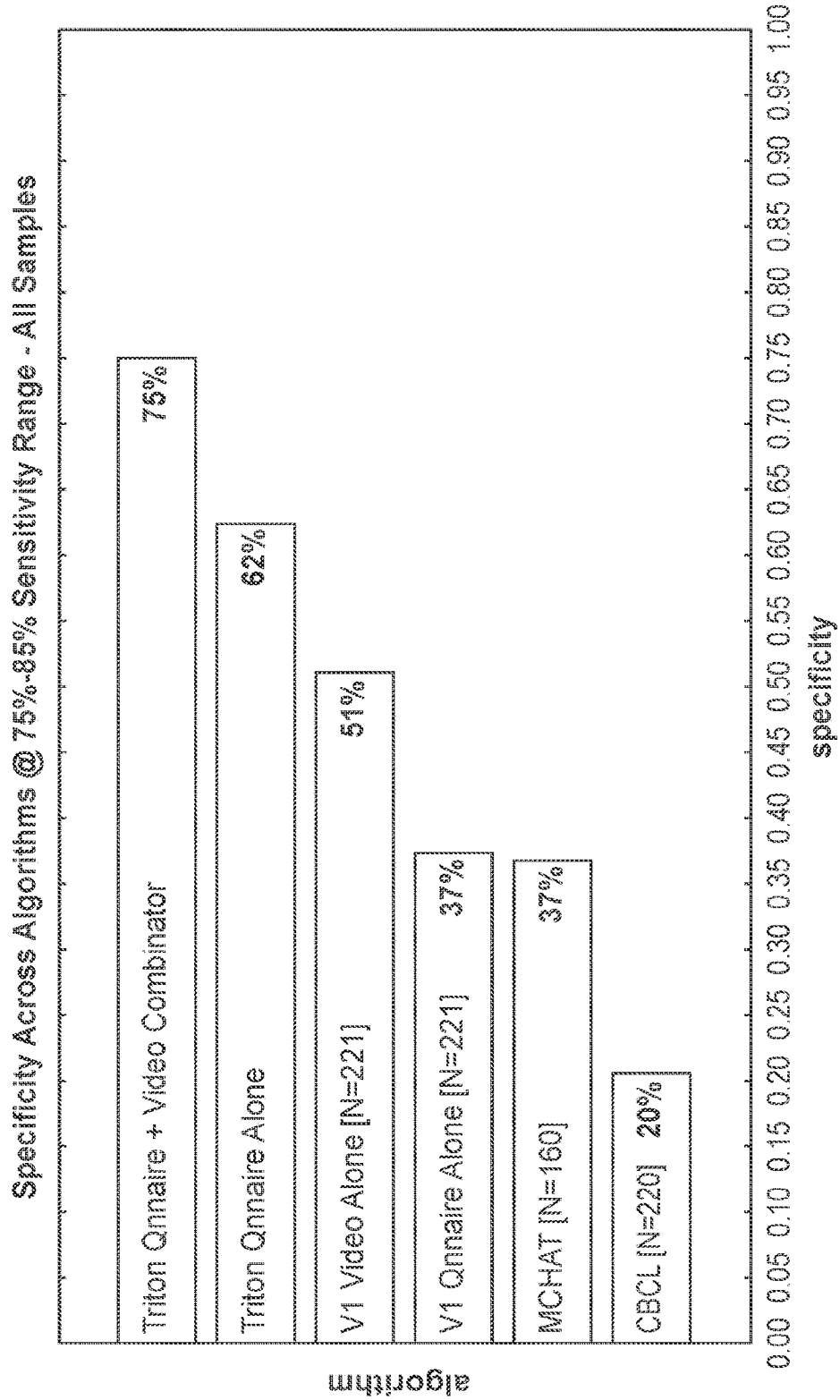
FIG. 20 shows the specificity across algorithms at 75%-85% sensitivity range for all samples as described herein.
Figure 21:
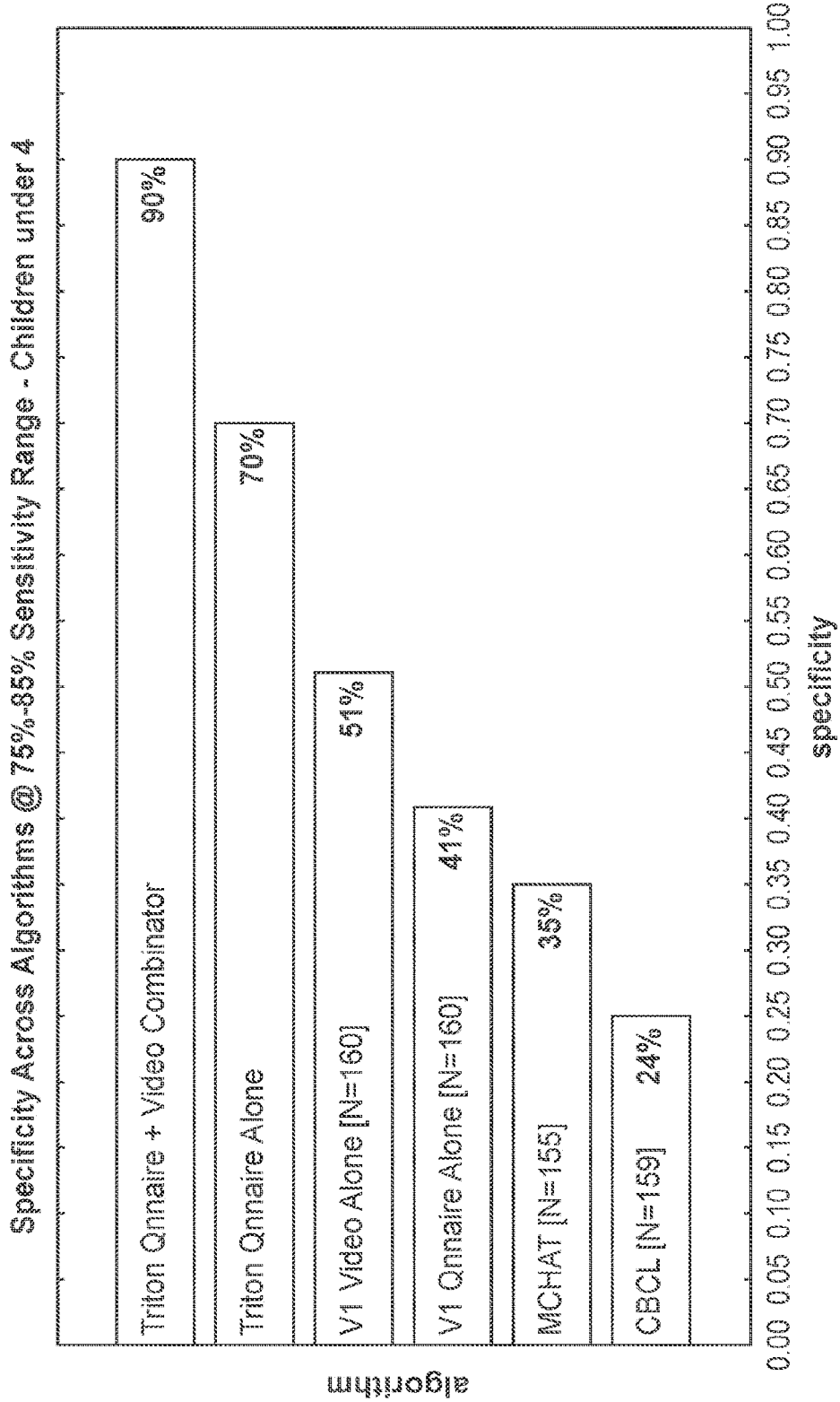
FIG. 21 shows the specificity across algorithms at 75%-85% sensitivity range for Children Under 4 as described herein.
Figure 22:
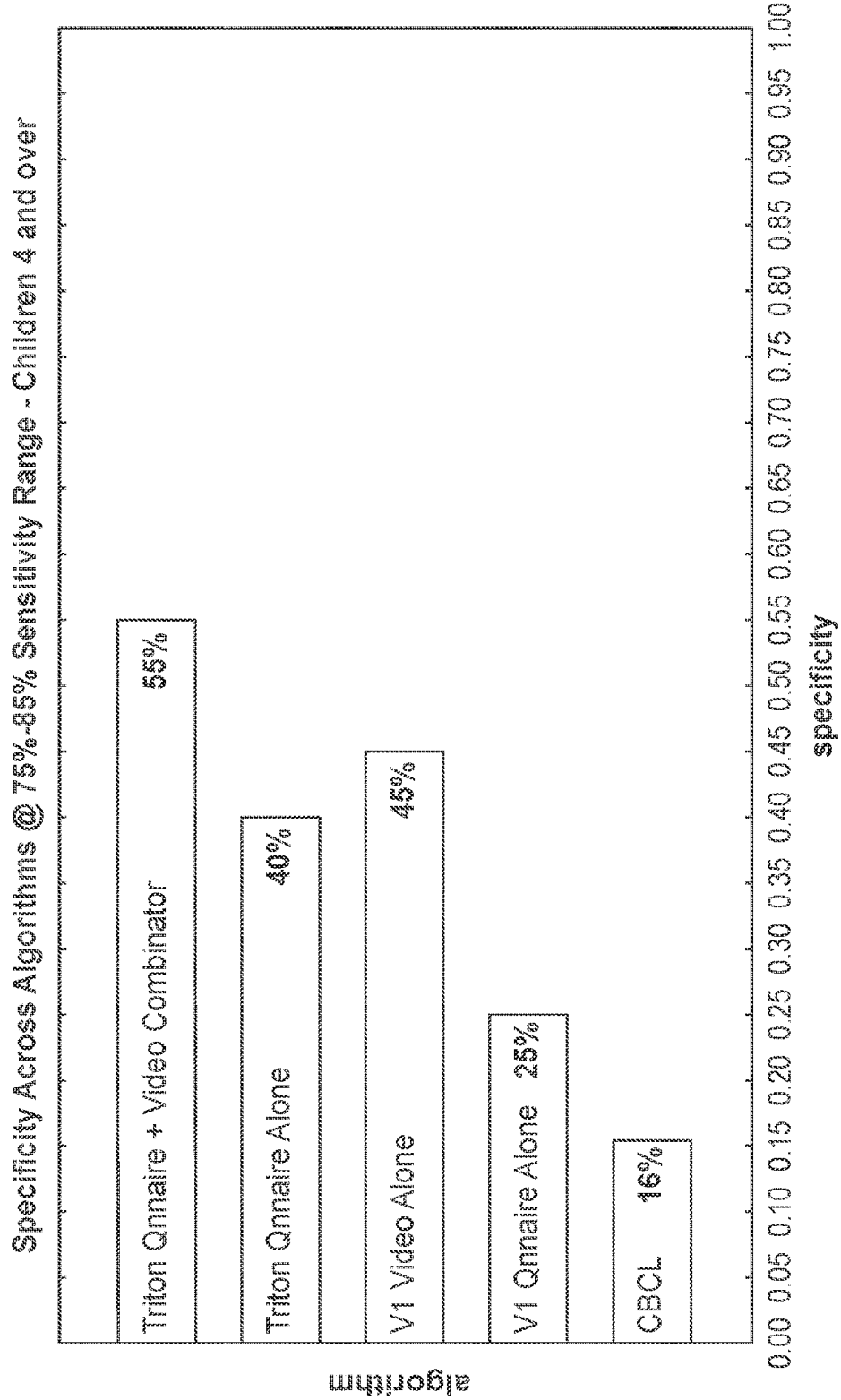
FIG. 22 shows the specificity across algorithms at 75%-85% sensitivity range for Children 4 and Over as described herein.

FIGS. 20-22, show the specificity for different algorithms at 75%-85% sensitivity range for all samples, for children under 4, and for children 4 and over. In all three cases, the Triton algorithm configured for 70% coverage when combined with the video combinator has the best performance, having 75% specificity for all samples, 90% specificity for children under 4, and 55% specificity for children 4 and over. Note that the Triton algorithm has the further advantage of flexibility. For example, tunable models are provided as described herein, wherein the inconclusive ratio or inclusion rate may be controlled or adjusted to control the tradeoff between coverage and reliability. In addition, the models described herein may be tuned to an application setting with respect to expected prevalence rates or based on expected population distributions for a given application setting. Finally, support for adaptive retraining enables improved performance over time given the feedback training loop of the method and system described herein.

A person of ordinary skill in the art can generate and obtain additional datasets and improve the sensitivity and specificity and confidence interval of the methods and apparatus disclosed herein to obtain improved results without undue experimentation. Although these measurements were performed with example datasets, the methods and apparatus can be configured with additional datasets as described herein and the subject identified as at risk with a confidence interval of 80% in a clinical environment without undue experimentation. The sensitivity and specificity of 80% or more in a clinical environment can be similarly obtained with the teachings provided herein by a person of ordinary skill in the art without undue experimentation, for example with additional datasets.

Additional datasets may be obtained from large archival data repositories as described herein, such as the Autism Genetic Resource Exchange (AGRE), Boston Autism Consortium (AC), Simons Foundation, National Database for Autism Research, and the like. Alternatively or in combination, additional datasets may comprise mathematically simulated data, generated based on archival data using various simulation algorithms. Alternatively or in combination, additional datasets may be obtained via crowd-sourcing, wherein subjects self-administer the assessment procedure as described herein and contribute data from their assessment. In addition to data from the self-administered assessment, subjects may also provide a clinical diagnosis obtained from a qualified clinician, so as to provide a standard of comparison for the assessment procedure.

In another aspect, a digital personalized medicine system as described herein comprises digital devices with processors and associated software configured to: receive data to assess and diagnose a patient; capture interaction and feedback data that identify relative levels of efficacy, compliance and response resulting from the therapeutic interventions; and perform data analysis, including at least one or machine learning, artificial intelligence, and statistical models to assess user data and user profiles to further personalize, improve or assess efficacy of the therapeutic interventions.

The assessment and diagnosis of the patient in the digital personalized medicine system can categorize a subject into one of three categories: having one or more developmental conditions, being developmentally normal or typical, or inconclusive (i.e. requiring additional evaluation to determine whether the subject has any developmental conditions). In particular, a separate category can be provided for inconclusive determinations, which results in greater accuracy with respect to categorical determinations indicating the presence or absence of a developmental condition. A developmental condition can be a developmental disorder or a developmental advancement. Moreover, the methods and apparatus disclosed herein are not limited to developmental conditions, and may be applied to other cognitive functions, such as behavioral, neurological or mental health conditions.

In some instances, the system can be configured to use digital diagnostics and digital therapeutics. Digital diagnostics and digital therapeutics can comprise a system or methods comprising collecting digital information and processing and evaluating the provided data to improve the medical, psychological, or physiological state of an individual. The system and methods described herein can categorize a subject into one of three categories: having one or more developmental conditions, being developmentally normal or typical, or inconclusive (i.e. requiring additional evaluation to determine whether the subject has any developmental conditions). In particular, a separate category can be provided for inconclusive determinations, which results in greater accuracy with respect to categorical determinations indicating the presence or absence of a developmental condition. A developmental condition can be a developmental disorder or a developmental advancement. Moreover, the methods and apparatus disclosed herein are not limited to developmental conditions, and may be applied to other cognitive functions, such as behavioral, neurological or mental health conditions. In addition, a digital therapeutic system can apply software based learning to evaluate user data, monitor and improve the diagnoses and therapeutic interventions provided by the system.

Digital diagnostics in the system can comprise of data and meta-data collected from the patient, or a caregiver, or a party that is independent of the individual being assessed. In some instances the collected data can comprise monitoring behaviors, observations, judgements, or assessments may be made by a party other than the individual. In further instances, the assessment can comprise an adult performing an assessment or provide data for an assessment of a child or juvenile.

Data sources can comprise either active or passive sources, in digital format via one or more digital devices such as mobile phones, video capture, audio capture, activity monitors, or wearable digital monitors. Examples of active data collection comprise devices, systems or methods for tracking eye movements, recording body or appendage movement, monitoring sleep patterns, recording speech patterns. In some instances, the active sources can include audio feed data source such as speech patterns, lexical/syntactic patterns (for example, size of vocabulary, correct/incorrect use of pronouns, correct/incorrect inflection and conjugation, use of grammatical structures such as active/passive voice etc., and sentence flow), higher order linguistic patterns (for example, coherence, comprehension, conversational engagement, and curiosity). Active sources can also include touch-screen data source (for example, fine-motor function, dexterity, precision and frequency of pointing, precision and frequency of swipe movement, and focus/attention span). Video recording of subject's face during activity (for example, quality/quantity of eye fixations vs saccades, heat map of eye focus on the screen, focus/attention span, variability of facial expression, and quality of response to emotional stimuli) can also be considered an active source of data.

Passive data collection can comprise devices, systems, or methods for collecting data from the user using recording or measurements derived from mobile applications, toys with embed sensors or recording units. In some instances, the passive source can include sensors embedded in smart toys (for example, fine motor function, gross motor function, focus/attention span and problem solving skills) and wearable devices (for example, level of activity, quantity/quality of rest).

The data used in the diagnosis and treatment can come from a plurality of sources, and may comprise a combination of passive and active data collection gathered from one device such as a mobile device with which the user interacts, or other sources such as microbiome sampling and genetic sampling of the subject.

The methods and apparatus disclosed herein are well suited for the diagnosis and digital therapeutic treatment of cognitive and developmental disorders, mood and mental illness, and neurodegenerative diseases. Examples of cognitive and developmental disorders include speech and learning disorders and other disorders as described herein. Examples of mood and mental illness disorders, which can effect children and adults, include behavioral disorders, mood disorders, depression, attention deficit hyperactivity disorder ("ADHD"), obsessive compulsive disorder ("OCD"), schizophrenia, and substance-related disorders such as eating disorders and substance abuse. Examples of neurodegenerative diseases include age related cognitive decline, cognitive impairment progressing to Alzheimer's and senility, Parkinson's disease and Huntington's disease, and amyotrophic lateral sclerosis ("ALS"). The methods and apparatus disclosed herein are capable of digitally diagnosing and treating children and continuing treatment until the subject becomes an adult, and can provide lifetime treatment based on personalized profiles.

The digital diagnosis and treatment as described herein is well suited for behavioral intervention coupled with biological or chemical therapeutic treatment. By gathering user interaction data as described herein, therapies can be provided for combinations of behavioral intervention data pharmaceutical and biological treatments.

The mobile devices as described herein may comprise sensors to collect data of the subject that can be used as part of the feedback loop so as to improve outcomes and decrease reliance on user input. The mobile device may comprise passive or active sensors as described herein to collect data of the subject subsequent to treatment. The same mobile device or a second mobile device, such as an iPad™ or iPhone™ or similar device, may comprise a software application that interacts with the user to tell the user what to do in improve treatment on a regular basis, e.g. day by day, hour by hour, etc. The user mobile device can be configured to send notifications to the user in response to treatment progress. The mobile device may comprise a drug delivery device configured to monitor deliver amounts of a therapeutic agent delivered to the subject.

The methods and apparatus disclosed herein are well suited for treatment of both parents and children, for example. Both a parent and a child can receive separate treatments as described herein. For example, neurological condition of the parent can be monitored and treated, and the developmental progress of the child monitored and treated.

The mobile device used to acquire data of the subject can be configured in many ways and may combine a plurality of devices, for example. For example, since unusual sleep patterns may be related to autism, sleep data acquired using the therapeutic apparatus described herein can be used as an additional input to the machine learning training process for autism classifiers used by the diagnostic apparatus described above. The mobile device may comprise a mobile wearable for sleep monitoring for a child, which can be provide as input for diagnosis and treatment and may comprise a component of the feedback loop as described herein.

Many types of sensor, biosensors and data can be used to gather data of the subject and input into the diagnosis and treatment of the subject. For example, work in relation to embodiments suggests that microbiome data can be useful for the diagnosis and treatment of autism. The microbiome data can be collected in many ways known to one of ordinary skill in the art, and may comprise data selected from a stool sample, intestinal lavage, or other sample of the flora of the subject's intestinal track. Genetic data can also be acquired an input into the diagnostic and therapeutic modules. The genetic data may comprise full genomic sequencing of the subject, of sequencing and identification of specific markers.

The diagnostic and therapeutic modules as disclosed herein can receive data from a plurality of sources, such as data acquired from the group consisting of genetic data, floral data, a sleep sensor, a wearable anklet sleep monitor, a booty to monitor sleep, and eye tracking of the subject. The eye tracking can be performed in many ways to determine the direction and duration of gaze. The tracking can be done with glasses, helmets or other sensors for direction and duration of gaze. The data can be collected during a visual session such as a video playback or video game, for example. This data can be acquired and provided to the therapeutic module and diagnostic module as described herein before, during and after treatment, in order to initially diagnose the subject, determine treatment of the subject, modify treatment of the subject, and monitor the subject subsequent to treatment.

The visual gaze, duration of gaze and facial expression information can be acquired with methods and apparatus known to one of ordinary skill in the art, and acquired as input into the diagnostic and therapeutic modules. The data can be acquired with an app comprising software instructions, which can be downloaded. For example, facial processing has been described by Gloarai et al. "Autism and the development of face processing", Clinical Neuroscience Research 6 (2006) 145-160. An autism research group at Duke University has been conducting the Autism and beyond research study with a software app downloaded onto mobile devices as described on the web page at autismandbeyond.researchkit.duke.edu. Data from such devices is particularly well suited for combination in accordance with the present disclosure. Facial recognition data and gaze data can be input into the diagnostic and therapeutic modules as described herein.

The classifiers as disclosed herein are particularly well suited for combination with this data to provide improved therapy and treatment. The data can be stratified and used with a feedback loop as described herein. For example, the feedback data can be used in combination with a drug therapy to determine differential responses and identify responders and non-responders. Alternatively or in combination, the feedback data can be combined with non-drug therapy, such as behavioral therapy.

With regards to genetics, recent work suggests that some people may have genes that make them more susceptible to Autism. The genetic composition of the subject may render the subject more susceptible to environmental influences, which can cause symptoms and may influence the severity of symptoms. The environmental influence may comprise an insult from a toxin, virus or other substance, for example. Without being bound by any particular theory, this may result in mechanisms that change the regulation of expression genes. The change in expression of genes may be related to change in gastro-intestinal ("GI") flora, and these changes in flora may affect symptoms related to Autism. Alternatively or in combination, an insult to the intestinal microbiome may result in a change in the microbiome of the subject, resulting in the subject having less than ideal homeostasis, which may affect associated symptoms related to Autism. The inventors note that preliminary studies with *B. fragilis* conducted by Sarkis K. Mazmanian and others, suggest changes in this micro-organism can be related to autism and the development of autisms. (See also, "Gut Bacteria May Play a Role in Autism" by Melinda Wenner Moyer, *Scientific American*, Sep. 1, 2014)

The digital diagnostic uses the data collected by the system about the patient, which may include complimentary diagnostic data captured outside the digital diagnostic, with analysis from tools such as machine learning, artificial intelligence, and statistical modeling to assess or diagnose the patient's condition. The digital diagnostic can also provide assessment of a patient's change in state or performance, directly or indirectly via data and meta-data that can be analyzed and evaluated by tools such as machine learning, artificial intelligence, and statistical modeling to provide feedback into the system to improve or refine the diagnoses and potential therapeutic interventions.

Analysis of the data comprising digital diagnostic, digital therapeutics, and corresponding responses, or lack thereof, from the therapeutic interventions can lead to the identification of novel diagnoses for patients and novel therapeutic regimens for both patents and caregivers.

Types of data collected and utilized by the system can include patient and caregiver video, audio, responses to questions or activities, and active or passive data streams from user interaction with activities, games or software features of the system, for example. Such data can also represent patient or caregiver interaction with the system, for example, when performing recommended activities. Specific examples include data from a user's interaction with the system's device or mobile app that captures aspects of the user's behaviors, profile, activities, interactions with the software system, interactions with games, frequency of use, session time, options or features selected, and content and activity preferences. Data may also include streams from various third party devices such as activity monitors, games or interactive content.

Digital therapeutics as described herein can comprise of instructions, feedback, activities or interactions provided to the patient or caregiver by the system. Examples include suggested behaviors, activities, games or interactive sessions with system software and/or third party devices (for example, the Internet of Things "IoT" enabled therapeutic devices as understood by one of ordinary skill in the art).

Figure 23A:
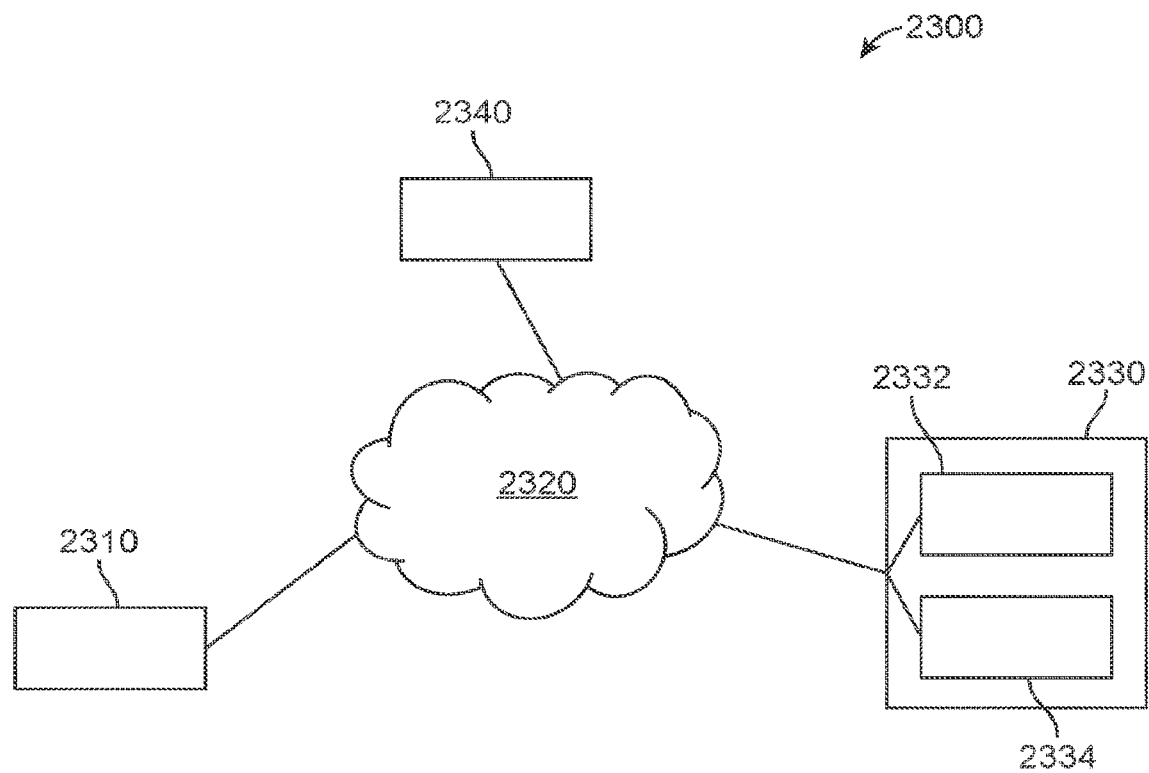
FIG. 23A illustrates an exemplary system diagram for a digital personalized medicine platform.

FIG. 23A illustrates a system diagram for a digital personalized medicine platform 2300 for providing diagnosis and therapy related to behavioral, neurological or mental health disorders. The platform 2300 can provide diagnosis and treatment of pediatric cognitive and behavioral conditions associated with developmental delays, for example. A user digital device 2310—for example, a mobile device such as a smart phone, an activity monitor, or a wearable digital monitor—records data and metadata related to a patient. Data may be collected based on interactions of the patient with the device, as well as based on interactions with caregivers and health care professionals. The data may be collected actively, such as by administering tests, recording speech and/or video, and recording responses to diagnostic questions. The data may also be collected passively, such as by monitoring online behavior of patients and caregivers, such as recording questions asked and topics investigated relating to a diagnosed developmental disorder.

The digital device 2310 is connected to a computer network 2320, allowing it to share data with and receive data from connected computers. In particular, the device can communicate with personalized medical system 2330, which comprises a server configured to communicate with digital device 2310 over the computer network 2320. Personalized medical system 2330 comprises a diagnosis module 2332 to provide initial and incremental diagnosis of a patient's developmental status, as well as a therapeutic module 2334 to provide personalized therapy recommendations in response to the diagnoses of diagnosis module 2332.

Each of diagnosis modules 2332 and 2334 communicate with the user digital device 2310 during a course of treatment. The diagnosis module provides diagnostic tests to and receives diagnostic feedback from the digital device 2310, and uses the feedback to determine a diagnosis of a patient. An initial diagnosis may be based on a comprehensive set of tests and questions, for example, while incremental updates may be made to a diagnosis using smaller data samples. For example, the diagnostic module may diagnose autism-related speech delay based on questions asked to the caregiver and tests administered to the patient such as vocabulary or verbal communication tests. The diagnosis may indicate a number of months or years delay in speech abilities. Later tests may be administered and questions asked to update this diagnosis, for example showing a smaller or larger degree of delay.

The diagnosis module communicates its diagnosis to the digital device 2310, as well as to therapy module 2334, which uses the diagnosis to suggest therapies to be performed to treat any diagnosed symptoms. The therapy module 2334 sends its recommended therapies to the digital device 2310, including instructions for the patient and caregivers to perform the therapies recommended over a given time frame. After performing the therapies over the given time frame, the caregivers or patient can indicate completion of the recommended therapies, and a report can be sent from the digital device 2310 to the therapy module 2334. The therapy module 2334 can then indicate to the diagnosis module 2332 that the latest round of therapy is finished, and that a new diagnosis is needed. The diagnostic module 2332 can then provide new diagnostic tests and questions to the digital device 2310, as well as take input from the therapy module of any data provided as part of a therapy, such as recordings of learning sessions or browsing history of caregivers or patients related to the therapy or diagnosed condition. The diagnostic module 2332 then provides an updated diagnosis to repeat the process and provide a next step of therapy.

Information related to diagnosis and therapy can also be provided from personalized medical system 2330 to a third-party system 2340, such as a computer system of a health care professional. The health care professional or other third party can be alerted to significant deviations from a therapy schedule, including whether a patient is falling behind an expected schedule or is improving faster than predicted. Appropriate further action can then be taken by the third party based on this provided information.

Figure 23B:
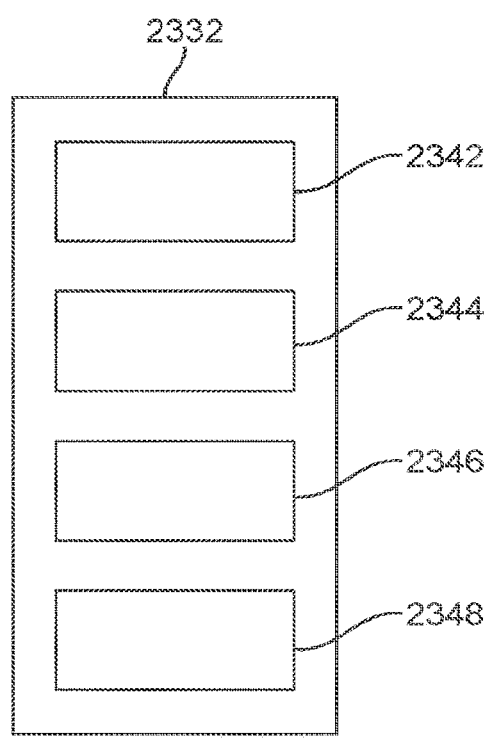
FIG. 23B illustrates a detailed diagram of an exemplary diagnosis module.

FIG. 23B illustrates a detailed diagram of diagnosis module 2332. The diagnosis module 2332 comprises a test administration module 2342 that generates tests and corresponding instructions for administration to a subject. The diagnosis module 2332 also comprises a subject data receiving module 2344 in which subject data are received, such as test results; caregiver feedback; meta-data from patient and caregiver interactions with the system; and video, audio, and gaming interactions with the system, for example. A subject assessment module 2346 generates a diagnosis of the subject based on the data from subject data receiving module 2344, as well as past diagnoses of the subject and of similar subjects. A machine learning module 2348 assesses the relative sensitivity of each input to the diagnosis to determine which types of measurement provide the most information regarding a patient's diagnosis. These results can be used by test administration module 2342 to provide tests which most efficiently inform diagnoses and by subject assessment module 2346 to apply weights to diagnosis data in order to improve diagnostic accuracy and consistency. Diagnostic data relating to each treated patient are stored, for example in a database, to form a library of diagnostic data for pattern matching and machine learning. A large number of subject profiles can be simultaneously stored in such a database, for example 10,000 or more.

Figure 23C:
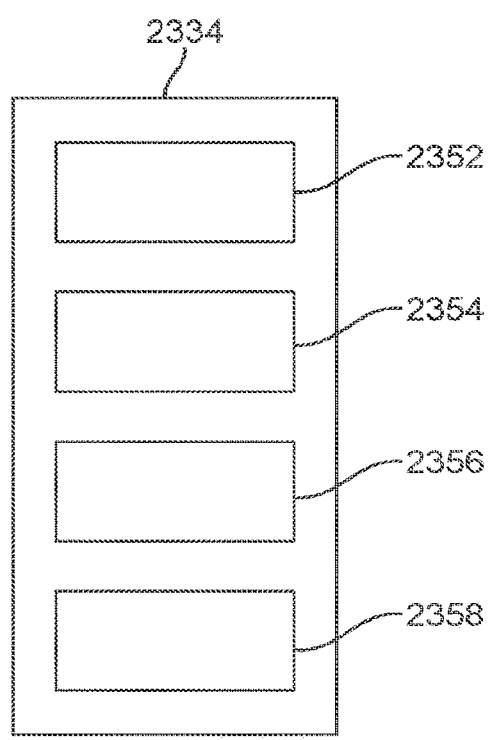
FIG. 23C illustrates a diagram of an exemplary therapy module.

FIG. 23C illustrates a detailed diagram of therapy module 2334. Therapy module 2334 comprises a therapy assessment module 2352 that scores therapies based on their effectiveness. A previously suggested therapy is evaluated based on the diagnoses provided by the diagnostic module both before and after the therapy, and a degree of improvement is determined. This degree of improvement is used to score the effectiveness of the therapy. The therapy may have its effectiveness correlated with particular classes of diagnosis; for example, a therapy may be considered effective for subjects with one type of diagnosis but ineffective for subjects with a second type of diagnosis. A therapy matching module 2354 is also provided that compares the diagnosis of the subject from diagnosis module 2332 with a list of therapies to determine a set of therapies that have been determined by the therapy assessment module 2352 to be most effective at treating diagnoses similar to the subject's diagnosis. Therapy recommendation module 2356 then generates a recommended therapy comprising one or more of the therapies identified as promising by the therapy matching module 2354, and sends that recommendation to the subject with instructions for administration of the recommended therapies. Therapy tracking module 2358 then tracks the progress of the recommended therapies, and determines when a new diagnosis should be performed by diagnosis module 2332, or when a given therapy should be continued and progress further monitored. Therapeutic data relating to each patient treated are stored, for example in a database, to form a library of therapeutic data for pattern matching and machine learning. A large number of subject profiles can be simultaneously stored in such a database, for example 10,000 or more. The therapeutic data can be correlated to the diagnostic data of the diagnostic module 2332 to allow a matching of effective therapies to diagnoses.

A therapy can comprise a digital therapy. A digital therapy can comprise a single or multiplicity of therapeutic activities or interventions that can be performed by the patient or caregiver. The digital therapeutic can include prescribed interactions with third party devices such as sensors, computers, medical devices and therapeutic delivery systems. Digital therapies can support an FDA approved medical claim, a set of diagnostic codes, or a single diagnostic code.

Figure 24:
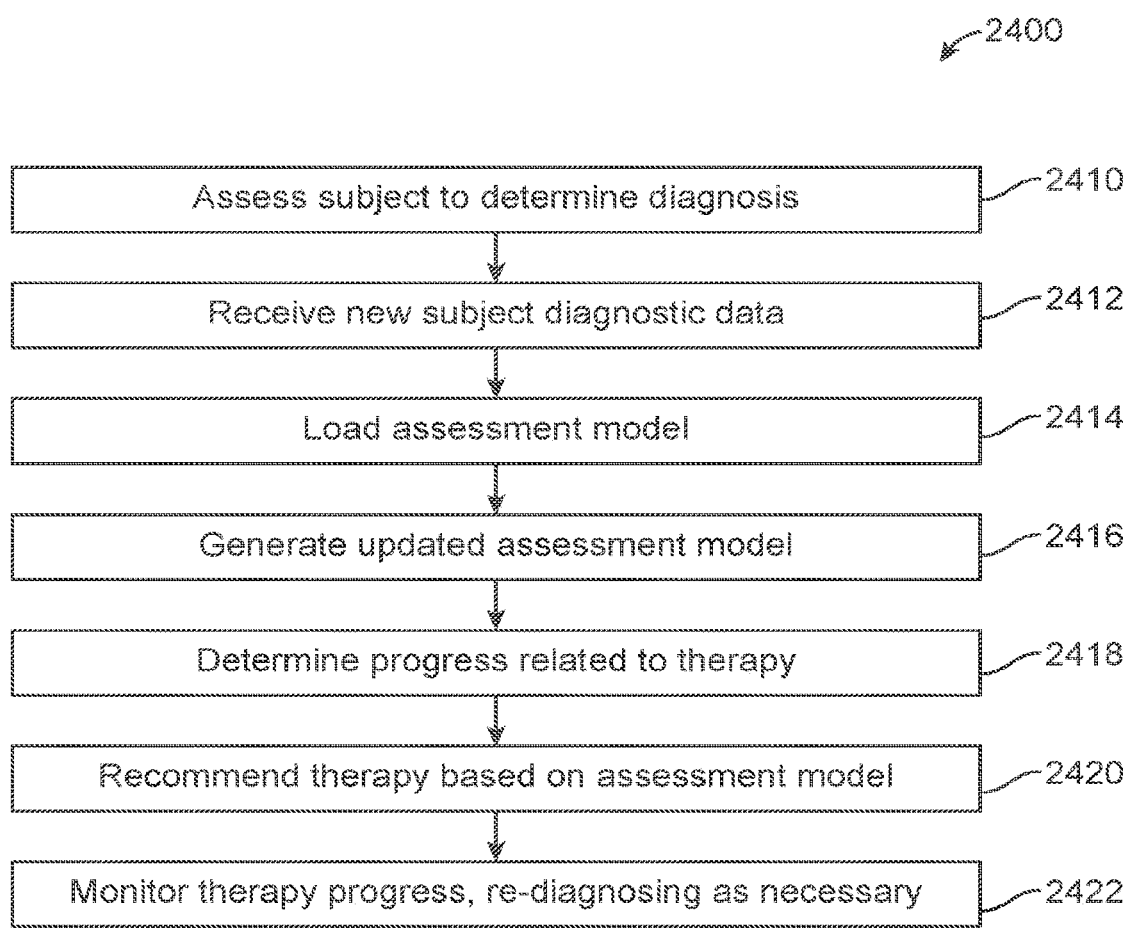
FIG. 24 illustrates an exemplary method for diagnosis and therapy to be provided in a digital personalized medicine platform.

FIG. 24 illustrates a method 2400 for diagnosis and therapy to be provided in a digital personalized medicine platform. The digital personalized medicine platform communicates with a subject, which may include a patient with one or more caregivers, to provide diagnoses and recommend therapies.

In step 2410 the diagnosis module assesses the subject to determine a diagnosis, for example by applying diagnostic tests to the subject. The diagnostic tests may be directed at determining a plurality of features and corresponding feature values for the subject. For example, the tests may include a plurality of questions presented to a subject, observations of the subject, or tasks assigned to the subject. The tests may also include indirect tests of the subject, such as feedback from a caregiver of patient performance versus specific behaviors and/or milestones; meta-data from patient and caregiver interactions with the system; and video, audio, and gaming interactions with the system or with third party tools that provide data on patient and caregiver behavior and performance. For initial tests, a more comprehensive testing regimen may be performed, aimed at generating an accurate initial diagnosis. Later testing used to update prior diagnoses to track progress can involve less comprehensive testing and may, for example, rely more on indirect tests such as behavioral tracking and therapy-related recordings and meta-data.

In step 2412, the diagnosis module receives new data from the subject. The new data can comprise an array of features and corresponding feature values for a particular subject. As described herein, the features may comprise a plurality of questions presented to a subject, observations of the subject, or tasks assigned to the subject. The feature values may comprise input data from the subject corresponding to characteristics of the subject, such as answers of the subject to questions asked, or responses of the subject. The feature values may also comprise recorded feedback, meta-data, and system interaction data as described above.

In step 2414, the diagnosis module can load a previously saved assessment model from a local memory and/or a remote server configured to store the model. Alternatively, if no assessment model exists for the patient, a default model may be loaded, for example, based on one or more initial diagnostic indications.

In step 2416, the new data is fitted to the assessment model to generate an updated assessment model. This assessment model may comprise an initial diagnosis for a previously untreated subject, or an updated diagnosis for a previously treated subject. The updated diagnosis can include a measurement of progress in one or more aspects of a condition, such as memory, attention and joint attention, cognition, behavioral response, emotional response, language use, language skill, frequency of specific behaviors, sleep, socialization, non-verbal communication, and developmental milestones. The analysis of the data to determine progress and current diagnosis can include automated analysis such as question scoring and voice-recognition for vocabulary and speech analysis. The analysis can also include human scoring by analysis reviewing video, audio, and text data.

In step 2418, the updated assessment model is provided to the therapy module, which determines what progress has been made as a result of any previously recommended therapy. The therapy module scores the therapy based on the amount of progress in the assessment model, with larger progress corresponding to a higher score, making a successful therapy and similar therapies more likely to be recommended to subjects with similar assessments in the future. The set of therapies available is thus updated to reflect a new assessment of effectiveness, as correlated with the subject's diagnosis.

In step 2420, a new therapy is recommended based on the assessment model, the degree of success of the previous therapy, if any, and the scores assigned to a collection of candidate therapies based on previous uses of those therapies with the subject and other subjects with similar assessments. The recommended therapy is sent to the subject for administration, along with instructions of a particular span of time to apply it. For example, a therapy might include a language drill to be performed with the patient daily for one week, with each drill to be recorded in an audio file in a mobile device used by a caregiver or the patient.

In step 2422, progress of the new therapy is monitored to determine whether to extend a period of therapy. This monitoring may include periodic re-diagnoses, which may be performed by returning to step 2410. Alternatively, basic milestones may be recorded without a full re-diagnosis, and progress may be compared to a predicted progress schedule generated by the therapy module. For example, if a therapy is unsuccessful initially, the therapy module may suggest repeating it one or more times before either re-diagnosing and suggesting a new therapy or suggesting intervention by medical professionals.

Figure 25:
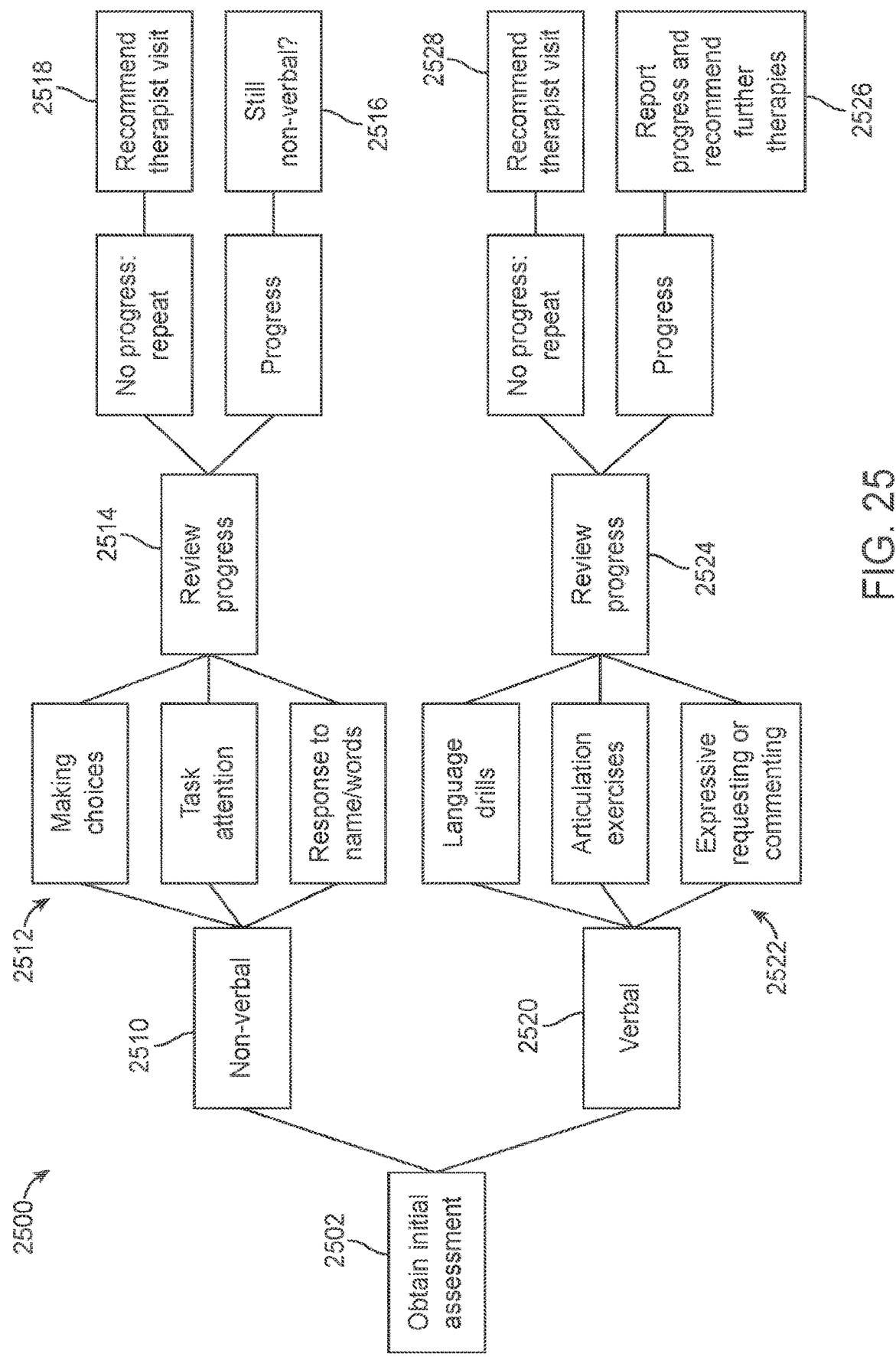
FIG. 25 illustrates an exemplary flow diagram showing the handling of autism-related developmental delay.

FIG. 25 illustrates a flow diagram 2500 showing the handling of suspected or confirmed speech and language delay.

In step 2502 an initial assessment is determined by diagnosis module 2532. The initial assessment can assess the patient's performance in one or more domains, such as speech and language use, and assess a degree and type of developmental delay along a number of axes, as disclosed herein. The assessment can further place the subject into one of a plurality of overall tracks of progress; for example, the subject can be assessed as verbal or nonverbal.

If the subject is determined to be non-verbal, as in step 2510, one or more non-verbal therapies 2512 can be recommended by the therapy module 2534, such as tasks related to making choices, paying attention to tasks, or responding to a name or other words. Further suggestions of useful devices and products that may be helpful for progress may also be provided, and all suggestions can be tailored to the subject's needs as indicated by the subject's diagnosis and progress reports.

While applying the recommended therapies, progress is monitored in step 2514 to determine whether a diagnosis has improved at a predicted rate.

If improvement has been measured in step 2514, the system determines whether the subject is still non-verbal in step 2516; if so, then the system returns to step 2510 and generates a new recommended therapy 2512 to induce further improvements.

If no improvement is measured in step 2514, the system can recommend that the therapy be repeated a predetermined number of times. The system may also recommend trying variations in therapy to try and get better results. If such repetitions and variations fail, the system can recommend a therapist visit in step 2518 to more directly address the problems impeding development.

Once the subject is determined to be verbal, as indicated in step 2520, verbal therapies 2522 can be generated by therapy module 2534. For example, verbal therapies 2522 can include one or more of language drills, articulation exercises, and expressive requesting or communicating. Further suggestions of useful devices and products that may be helpful for progress may also be provided, and all suggestions can be tailored to the subject's needs as indicated by the subject's diagnosis and progress reports.

As in the non-verbal track, progress in response to verbal therapies is continually monitored in step 2524 to determine whether a diagnosis has improved at a predicted rate.

If improvement has been measured in step 2524, the system reports on the progress in step 326 and generates a new recommended therapy 2522 to induce further improvements.

If no improvement is detected in step 2524, the system can recommend that the therapy be repeated a predetermined number of times. The system may also recommend trying variations in therapy to try and get better results. If such repetitions and variations fail, the system can recommend a therapist visit in step 2528 to more directly address the problems impeding development.

The steps for non-verbal and verbal therapy can be repeated indefinitely, to the degree needed to stimulate continued learning and progress in the subject, and to prevent or retard regress through loss of verbal skills and abilities. While the specific therapy plan illustrated in FIG. 25 is directed towards pediatric speech and language delay similar plans may be generated for other subjects with developmental or cognitive issues, including plans for adult patients. For example, neurodegenerative conditions and/or age related cognitive decline may be treated with similar diagnosis and therapy schedules, using treatments selected to be appropriate to such conditions. Further conditions that may be treated in adult or pediatric patients by the methods and systems disclosed herein include mood disorders such as depression, OCD, and schizophrenia; cognitive impairment and decline; sleep disorders; addictive behaviors; eating disorders; and behavior related weight management problems.

Figure 26:
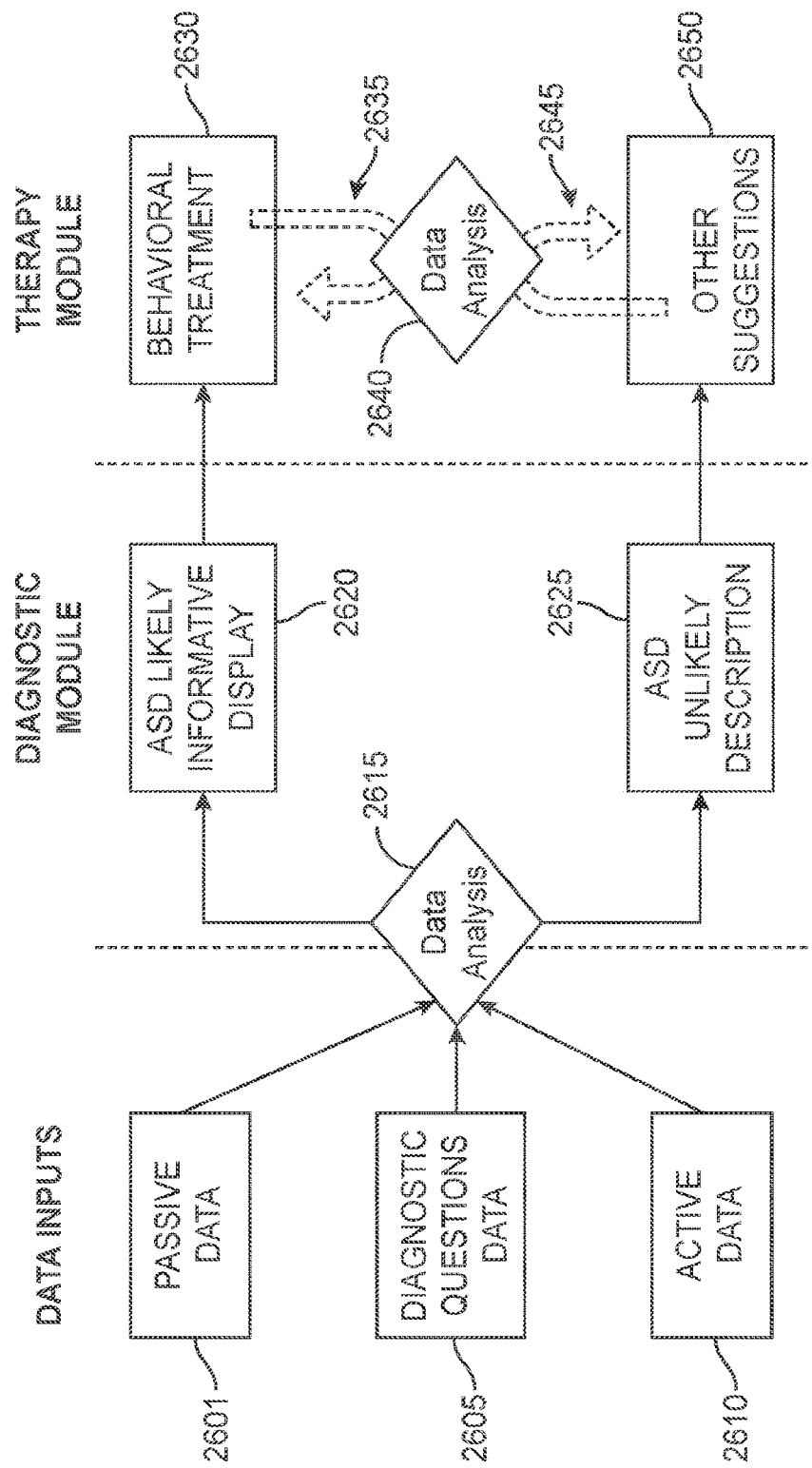
FIG. 26 illustrates an overall of data processing flows for a digital personalized medical system comprising a diagnostic module and a therapeutic module, configured to integrate information from multiple sources.

FIG. 26 illustrates an overall of data processing flows for a digital personalized medical system comprising a diagnostic module and a therapeutic module, configured to integrate information from multiple sources. Data can include passive data sources (2601), passive data can be configured to provide more fine grained information, and can comprise data sets taken over longer periods of time under more natural conditions. Passive data sources can include for example, data collected from wearable devices, data collected from video feeds (e.g. a video-enabled toy, a mobile device, eye tracking data from video playback), information on the dexterity of a subject based on information gathered from three-axis sensors or gyroscopes (e.g. sensors embedded in toys or other devices that the patient may interact with for example at home, or under normal conditions outside of a medical setting), smart devices that measure any single or combination of the following: subject's speech patterns, motions, touch response time, prosody, lexical vocabulary, facial expressions, and other characteristic expressed by the subject. Passive data can comprise data on the motion or motions of the user, and can include subtle information that may or may not be readily detectable to an untrained individual. In some instances, passive data can provide information that can be more encompassing.

Passively collected data can comprise data collected continuously from a variety of environments. Passively collected data can provide a more complete picture of the subject and thus can improve the quality of an assessment. In some instances, for example, passively collected data can include data collected both inside and outside of a medical setting. Passively collected data taken in a medical setting can differ from passively collected data taken from outside a medical setting. Therefore, continuously collected passive data can comprise a more complete picture of a subject's general behavior and mannerisms, and thus can include data or information that a medical practitioner would not otherwise have access to. For example, a subject undergoing evaluation in a medical setting may display symptoms, gestures, or features that are representative of the subject's response to the medical environment, and thus may not provide a complete and accurate picture of the subject's behavior outside of the medical environment under more familiar conditions. The relative importance of one or more features (e.g. features assessed by a diagnostic module) derived from an assessment in the medical environment, may differ from the relative importance of one or more features derived from or assessed outside the clinical setting.

Data can comprise information collected through diagnostic tests, diagnostic questions, or questionnaires (2605). In some instances, data from diagnostic tests (2605) can comprise data collected from a secondary observer (e.g. a parent, guardian, or individual that is not the subject being analyzed). Data can include active data sources (2610), for example data collected from devices configured for tracking eye movement, or measuring or analyzing speech patterns.

As illustrated in FIG. 26, data inputs can be fed into a diagnostic module which can comprise data analysis (2615) using for example a classifier, algorithm (e.g. machine learning algorithm), or statistical model, to make a diagnosis of whether the subject is likely to have a tested disorder (e.g. Autism Spectrum Disorder) (2620) or is unlikely to have the tested disorder (2625). The methods and apparatus disclosed herein can alternatively be employed to include a third inconclusive category (not depicted in this diagram), which corresponds to the subject requiring additional evaluation to determine whether he/she is or is not likely to have a tested disorder. The methods and apparatus disclosed herein are not limited to disorders, and may be applied to other cognitive functions, such as behavioral, neurological, mental health, or developmental conditions. The methods and apparatus may initially categorize a subject into one of the three categories, and subsequently continue with the evaluation of a subject initially categorized as "inconclusive" by collecting additional information from the subject. Such continued evaluation of a subject initially categorized as "inconclusive" may be performed continuously with a single screening procedure (e.g., containing various assessment modules). Alternatively or additionally, a subject identified as belonging to the inconclusive group may be evaluated using separate, additional screening procedures and/or referred to a clinician for further evaluation.

In instances where the subject is determined by the diagnostic model as likely to have the disorder (2620), a secondary party (e.g. medical practitioner, parent, guardian or other individual) may be presented with an informative display. An informative display can provide symptoms of the disorder that can be displayed as a graph depicting covariance of symptoms displayed by the subject and symptoms displayed by the average population. A list of characteristics associated with a particular diagnosis can be displayed with confidence values, correlation coefficients, or other means for displaying the relationship between a subject's performance and the average population or a population comprised of those with a similar disorders.

If the digital personalized medicine system predicts that the user is likely to have a diagnosable condition (e.g. Autism Spectrum Disorder), then a therapy module can provide a behavioral treatment (2630) which can comprise behavioral interventions; prescribed activities or trainings; interventions with medical devices or other therapeutics for specific durations or, at specific times or instances. As the subject undergoes the therapy, data (e.g. passive data and diagnostic question data) can continue to be collected to perform follow-up assessments, to determine for example, whether the therapy is working. Collected data can undergo data analysis (2640) (e.g. analysis using machine learning, statistical modeling, classification tasks, predictive algorithms) to make determinations about the suitability of a given subject. A growth curve display can be used to show the subject's progress against a baseline (e.g. against an age-matched cohort). Performance or progress of the individual may be measured to track compliance for the subject with a suggested behavioral therapy predicted by the therapy module may be presented as a historic and predicted performance on a growth curve. Procedures for assessing the performance of an individual subject may be repeated or iterated (2635) until an appropriate behavioral treatment is identified.

The digital therapeutics treatment methods and apparatus described with reference to FIGS. 23A-23C and FIGS. 24-26 are particularly well suited for combination with the methods and apparatus to evaluate subjects with fewer questions described herein with reference to FIGS. 1A to 10. For example, the components of diagnosis module 2332 as described herein can be configured to assess the subject with the decreased set of questions comprising the most relevant question as described herein, and subsequently evaluated with the therapy module 2334 to subsequently assess the subject with subsequent set of questions comprising the most relevant questions for monitoring treatment as described herein.

Figure 27:
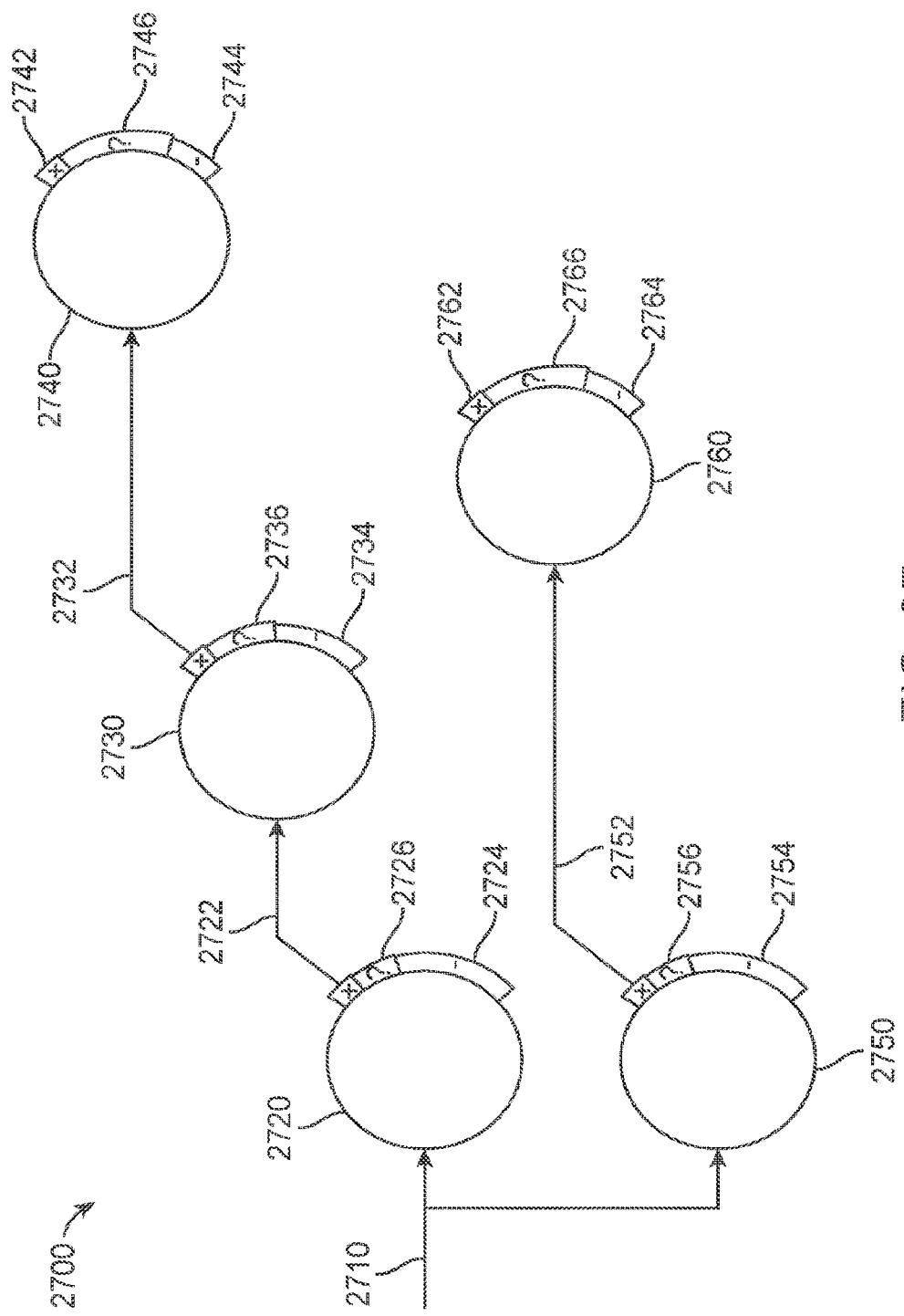
FIG. 27 shows a system for evaluating a subject for multiple clinical indications.

FIG. 27 shows a system 2700 for evaluating a subject for multiple clinical indications. The system 2700 may comprise a plurality of cascaded diagnostic modules (such as diagnostic modules 2720, 2730, 2740, 2750, and 2760). The cascaded diagnostic modules may be operatively coupled (such as in a chain of modules) such that an output from one diagnostic module may form an input to another diagnostic module. As shown in FIG. 27, the system may comprise a social or behavioral delay module 2720, an autism or ADHD module 2730, an autism and ADHD discrimination module 2740, a speech or language delay module 2750, and an intellectual disability module 2760. Modules (e.g., such as the diagnostic modules described with respect to FIG. 27) as described anywhere herein may refer to modules comprising a classifier. Accordingly, a social or behavioral delay module may comprise a social or behavioral delay classifier, an autism or ADHD module may comprise an autism or ADHD classifier, an autism and ADHD discrimination module may comprise an autism and ADHD classifier, a speech or language delay module may comprise a speech or language delay classifier, an intellectual disability module may comprise an intellectual disability classifier, and so forth.

The social or behavioral delay module 2720 may receive information 2710, such as information from an interactive questionnaire described herein. The social or behavioral delay module may utilize any diagnostic operations described herein to determine a social or behavioral delay diagnostic status of the subject. For instance, the social or behavioral delay module may utilize any operations of the procedure 1300 described with respect to FIG. 13 to determine a social or behavioral delay diagnostic status (i.e., whether or not the subject displays behaviors consistent with social or behavioral delay). Upon a determination of the social or behavioral delay diagnostic status, the social or behavioral delay module may output a determination as to whether or not the subject displays social or behavioral delay. The social or behavioral delay module may output a positive identification 2722 indicating that the subject does display social or behavioral delay. The social or behavioral delay module may output a negative indication 2724 indicating that the subject does not display social or behavioral delay. The social or behavioral delay module may output an inconclusive indication 2726 indicating that the social or behavioral delay module has been unable to determine whether or not the subject displays social or behavioral delay.

When the social or behavioral delay module determines that the subject does not display social or behavioral delay or that the result of the social or behavioral delay inquiry is indeterminate, the system may output such a result and halt its inquiry into the subject's social or behavioral health.

However, when the social or behavioral delay module determines that the subject does display social or behavioral delay, the social or behavioral delay module may pass this result, and information 2710, to the autism or ADHD module 2730.

The autism or ADHD delay module may utilize any diagnostic operations described herein to determine an autism or ADHD status of the subject. For instance, the autism or ADHD delay module may utilize any operations of the procedure 1300 described with respect to FIG. 13 to determine an autism or ADHD diagnostic status (i.e., whether or not the subject displays behaviors consistent with autism or ADHD). Upon a determination of the autism or ADHD diagnostic status, the autism or ADHD module may output a determination as to whether or not the subject displays autism or ADHD. The autism or ADHD module may output a positive identification 2732 indicating that the subject does display autism or ADHD. The autism or ADHD module may output a negative indication 2734 indicating that the subject does not display autism or ADHD. The autism or ADHD module may output an inconclusive indication 2736 indicating that the autism or ADHD module has been unable to determine whether or not the subject displays autism or ADHD.

When the autism or ADHD module determines that the subject does not display autism or ADHD or that the result of the autism or ADHD inquiry is indeterminate, the system may output such a result and halt its inquiry into the subject's social or behavioral health. In such a scenario, the system may revert to the earlier diagnosis that the subject displays social or behavioral delay.

However, when the autism or ADHD module determines that the subject does display autism or ADHD, the autism or ADHD module may pass this result, and information 2710, to the autism and ADHD discrimination module 2740.

The autism and ADHD discrimination module may utilize any diagnostic operations described herein to discriminate between autism and ADHD. For instance, the autism and ADHD discrimination module may utilize any operations of the procedure 1300 described with respect to FIG. 13 to discriminate between autism and ADHD for the subject (i.e., to determine whether the subject displays behaviors that are more consistent with autism or with ADHD). Upon a discriminating between autism and ADHD, the autism and ADHD discrimination module may output a determination as to whether displays autism or whether the subject displays ADHD. The autism and ADHD discrimination module may output an indication 2742 indicating that the subject displays autism. The autism and ADHD discrimination module may output an indication 2744 indicating that the subject displays ADHD. The autism and ADHD discrimination module may output an inconclusive indication 2746 indicating that the autism and ADHD discrimination module has been unable to discriminate between whether the subject's behavior is more consistent with autism or with ADHD.

When the autism and ADHD discrimination module determines that the result of the autism and ADHD discrimination inquiry is indeterminate, the system may output such a result and halt its inquiry into the subject's social or behavioral health. In such a scenario, the system may revert to the earlier diagnosis that the subject displays behavior consistent with autism or ADHD.

Alternatively or in combination, the autism and ADHD discrimination module may be further configured to pass information 2710 to one or more additional modules. For instance, the autism and ADHD discrimination module may be configured to pass information to an obsessive compulsive disorder module (not shown in FIG. 27). The obsessive compulsive disorder module may make a determination as to whether a subject displays behavior consistent with obsessive compulsive disorder using any of the systems and methods described herein (such as any operations of the procedure 1300).

Alternatively or in combination, the speech or language delay module 2750 may receive the information 2710. The speech or language delay module may utilize any diagnostic operations described herein to determine a speech or language delay diagnostic status of the subject. For instance, the speech or language delay module may utilize any operations of the procedure 1300 described with respect to FIG. 13 to determine a speech or language delay diagnostic status (i.e., whether or not the subject displays behaviors consisting with speech or language delay). Upon a determination of the speech or language delay diagnostic status, the speech or language delay module may output a determination as to whether or not the subject displays speech or language delay. The speech or language delay module may output a positive identification 2752 indicating that the subject does display speech or language delay. The speech or language delay module may output a negative indication 2754 indicating that the subject does not display speech or language delay. The speech or language delay module may output an inconclusive indication 2756 indicating that the speech or language delay module has been unable to determine whether or not the subject displays speech or language delay.

When the speech or language delay module determines that the subject does not display speech or language delay or that the result of the speech or language delay inquiry is indeterminate, the system may output such a result and halt its inquiry into the subject's speech or language health.

However, when the speech or language delay module determines that the subject does display speech or language delay, the speech or language delay module may pass this result, and information 2710, to the intellectual disability module 2760.

The intellectual disability module may utilize any diagnostic operations described herein to determine an intellectual disability status of the subject. For instance, the intellectual disability module may utilize any operations of the procedure 1300 described with respect to FIG. 13 to determine an intellectual disability diagnostic status (i.e., whether or not the subject displays behaviors consistent with intellectual disability). Upon a determination of the intellectual disability diagnostic status, the intellectual disability module may output a determination as to whether or not the subject displays intellectual disability. The intellectual disability module may output a positive identification 2762 indicating that the subject does display intellectual disability. The intellectual disability module may output a negative indication 2764 indicating that the subject does not display intellectual disability. The intellectual disability module may output an inconclusive indication 2766 indicating that the intellectual disability module has been unable to determine whether or not the subject displays intellectual disability.

When the intellectual disability module determines that the subject does not display intellectual disability or that the result of the intellectual disability inquiry is indeterminate, the system may output such a result and halt its inquiry into the subject's speech or language health. In such a scenario, the system may revert to the earlier diagnosis that the subject displays speech or language delay.

Alternatively or in combination, the intellectual disability module may be further configured to pass information 2710 to one or more additional modules. For instance, the intellectual disability module may be configured to pass information to a dyslexia module (not shown in FIG. 27). The dyslexia module may make a determination as to whether a subject displays behavior consistent with dyslexia using any of the systems and methods described herein (such as any operations of the procedure 1300).

Though described with reference to social or behavioral delay, autism, ADHD, obsessive compulsive disorder, speech or language delay, intellectual disability, and dyslexia, the system 2700 may comprise any number of modules (such as 1, 2, 3, 4, 5, 6, 7, 8, 9, 10, or more than 10 modules) that may provide a diagnostic status for any behavioral disorder. The modules may be operatively coupled (such as cascaded or chained) in any possible order.

The systems and methods described anywhere herein may be used as a basis for a treatment plan, or for administration of a drug, for a disorder diagnosed by any system or method for diagnosis described herein.

The systems and methods described anywhere herein may be used to administer a drug to treat acute stress disorder, such as propranolol, citalopram, escitalopram, sertraline, paroxetine, fluoextine, venlafaxine, mirtazapine, nefazodone, carbamazepine, divalproex, lamotrigine, topiramate, prazosin, phenelzine, imipramine, diazepam, clonazepam, lorazepam, or alprazolam.

The systems and methods described anywhere herein may be used to administer a drug to treat adjustment disorder, such as busiprone, escitalopram, sertraline, paroxetine, fluoextine, diazepam, clonazepam, lorazepam, or alprazolam.

The systems and methods described anywhere herein may be used to administer a drug to treat agoraphobia, such as diazepam, clonazepam, lorazepam, alprazolam, citalopram, escitalopram, sertraline, paroxetine, fluoextine, or busiprone.

The systems and methods described anywhere herein may be used to administer a drug to treat Alzheimer's disease, such as donepezil, galantamine, memantine, or rivastigmine.

The systems and methods described anywhere herein may be used to administer a drug to treat anorexia nervosa, such as olanzapine, citalopram, escitalopram, sertraline, paroxetine, or fluoextine.

The systems and methods described anywhere herein may be used to administer a drug to treat anxiety disorders, such as sertraline, escitalopram, citalopram, fluoxetine, diazepam, buspirone, venlafaxine, duloxetine, imipramine, desipramine, clomipramine, lorazepam, clonazepam, or pregabalin.

The systems and methods described anywhere herein may be used to administer a drug to treat attachment disorder.

The systems and methods described anywhere herein may be used to administer a drug to treat attention deficit/hyperactivity disorder (ADHD/ADD), such as amphetamine (for instance, in a dosage of 5 mg to 50 mg), dextroamphetamine (for instance, in a dosage of 5 mg to 60 mg), methylphenidate (for instance, in a dosage of 5 mg to 60 mg), methamphetamine (for instance, in a dosage of 5 mg to 25 mg), dexmethylphenidate (for instance, in a dosage of 2.5 mg to 40 mg), guanfacine (for instance, in a dosage of 1 mg to 10 mg), atomoxetine (for instance, in a dosage of 10 mg to 100 mg), lisdexamfetamine (for instance, in a dosage of 30 mg to 70 mg), clonidine (for instance, in a dosage of 0.1 mg to 0.5 mg), or modafinil (for instance, in a dosage of 100 mg to 500 mg).

The systems and methods described anywhere herein may be used to administer a drug to treat autism or autism spectrum disorders, such as risperidone (for instance, in a dosage of 0.5 mg to 20 mg), quetiapine (for instance, in a dosage of 25 mg to 1000 mg), amphetamine (for instance, in a dosage of 5 mg to 50 mg), dextroamphetamine (for instance, in a dosage of 5 mg to 60 mg), methylphenidate (for instance, in a dosage of 5 mg to 60 mg), methamphetamine (for instance, in a dosage of 5 mg to 25 mg), dexmethylphenidate (for instance, in a dosage of 2.5 mg to 40 mg), guanfacine (for instance, in a dosage of 1 mg to 10 mg), atomoxetine (for instance, in a dosage of 10 mg to 100 mg), lisdexamfetamine (for instance, in a dosage of 30 mg to 70 mg), clonidine (for instance, in a dosage of 0.1 mg to 0.5 mg), or aripiprazole (for instance, in a dosage of 1 mg to 10 mg).

The systems and methods described anywhere herein may be used to administer a drug to treat bereavement, such as citalopram, duloxetine, or doxepin.

The systems and methods described anywhere herein may be used to administer a drug to treat binge eating disorder, such as lisdexamfetamine.

The systems and methods described anywhere herein may be used to administer a drug to treat bipolar disorder, such as topiramate, lamotrigine, oxcarbazepine, haloperidol, risperidone, quetiapine, olanzapine, aripiprazole, or fluoxetine.

The systems and methods described anywhere herein may be used to administer a drug to treat body dysmorphic disorder, such as sertraline, escitalopram, or citalopram.

The systems and methods described anywhere herein may be used to administer a drug to treat brief psychotic disorder, such as clozapine, asenapine, olanzapine, or quetiapine.

The systems and methods described anywhere herein may be used to administer a drug to treat bulimia nervosa, such as sertraline, or fluoxetine.

The systems and methods described anywhere herein may be used to administer a drug to treat conduct disorder, such as lorazepam, diazepam, or clobazam.

The systems and methods described anywhere herein may be used to administer a drug to treat cyclothymic disorder.

The systems and methods described anywhere herein may be used to administer a drug to treat delusional disorder, such as clozapine, asenapine, risperidone, venlafaxine, bupropion, or buspirone.

The systems and methods described anywhere herein may be used to administer a drug to treat depersonalization disorder, such as sertraline, fluoxetine, alprazolam, diazepam, or citalopram.

The systems and methods described anywhere herein may be used to administer a drug to treat depression, such as sertraline, fluoxetine, citalopram, bupropion, escitalopram, venlafaxine, aripiprazole, buspirone, vortioxetine, or vilazodone.

The systems and methods described anywhere herein may be used to administer a drug to treat disinhibited social engagement disorder.

The systems and methods described anywhere herein may be used to administer a drug to treat disruptive mood dysregulation disorder, such as quetiapine, clozapine, asenapine, or pimavanserin.

The systems and methods described anywhere herein may be used to administer a drug to treat dissociative amnesia, such as alprazolam, diazepam, lorazepam, or chlordiazepoxide.

The systems and methods described anywhere herein may be used to administer a drug to treat dissociative disorder, such as bupropion, vortioxetine, or vilazodone.

The systems and methods described anywhere herein may be used to administer a drug to treat dissociative fugue, such as amobarbital, aprobarbital, butabarbital, or methohexitlal.

The systems and methods described anywhere herein may be used to administer a drug to treat dissociative identity disorder.

The systems and methods described anywhere herein may be used to administer a drug to treat dyslexia, such as amphetamine (for instance, in a dosage of 5 mg to 50 mg), dextroamphetamine (for instance, in a dosage of 5 mg to 60 mg), methylphenidate (for instance, in a dosage of 5 mg to 60 mg), methamphetamine (for instance, in a dosage of 5 mg to 25 mg), dexmethylphenidate (for instance, in a dosage of 2.5 mg to 40 mg), guanfacine (for instance, in a dosage of 1 mg to 10 mg), atomoxetine (for instance, in a dosage of 10 mg to 100 mg), lisdexamfetamine (for instance, in a dosage of 30 mg to 70 mg), clonidine (for instance, in a dosage of 0.1 mg to 0.5 mg), or modafinil (for instance, in a dosage of 100 mg to 500 mg).

The systems and methods described anywhere herein may be used to administer a drug to treat dysthymic disorder, such as bupropion, venlafaxine, sertraline, or citalopram.

The systems and methods described anywhere herein may be used to administer a drug to treat eating disorders, such as olanzapine, citalopram, escitalopram, sertraline, paroxetine, or fluoextine.

The systems and methods described anywhere herein may be used to administer a drug to treat expressive language disorder.

The systems and methods described anywhere herein may be used to administer a drug to treat gender dysphoria, such as estrogen, prostogen, or testosterone.

The systems and methods described anywhere herein may be used to administer a drug to treat generalized anxiety disorder, such as venlafaxine, duloxetine, buspirone, sertraline, or fluoxetine.

The systems and methods described anywhere herein may be used to administer a drug to treat hoarding disorder, such as buspirone, sertraline, escitalopram, citalopram, fluoxetine, paroxetine, venlafaxine, or clomipramine.

The systems and methods described anywhere herein may be used to administer a drug to treat intellectual disability.

The systems and methods described anywhere herein may be used to administer a drug to treat intermittent explosive disorder, such as asenapine, clozapine, olanzapine, or pimavanserin.

The systems and methods described anywhere herein may be used to administer a drug to treat kleptomania, such as escitalopram, fluvoxamine, fluoxetine, or paroxetine.

The systems and methods described anywhere herein may be used to administer a drug to treat mathematics disorder.

The systems and methods described anywhere herein may be used to administer a drug to treat obsessive-compulsive disorder, such as buspirone (for instance, in a dosage of 5 mg to 60 mg), sertraline (for instance, in a dosage of up to 200 mg), escitalopram (for instance, in a dosage of up to 40 mg), citalopram (for instance, in a dosage of up to 40 mg), fluoxetine (for instance, in a dosage of 40 mg to 80 mg), paroxetine (for instance, in a dosage of 40 mg to 60 mg), venlafaxine (for instance, in a dosage of up to 375 mg), clomipramine (for instance, in a dosage of up to 250 mg), or fluvoxamine (for instance, in a dosage of up to 300 mg).

The systems and methods described anywhere herein may be used to administer a drug to treat oppositional defiant disorder.

The systems and methods described anywhere herein may be used to administer a drug to treat panic disorder, such as bupropion, vilazodone, or vortioxetine.

The systems and methods described anywhere herein may be used to administer a drug to treat Parkinson's disease, such as rivastigmine, selegiline, rasagiline, bromocriptine, amantadine, cabergoline, or benztropine.

The systems and methods described anywhere herein may be used to administer a drug to treat pathological gambling, such as bupropion, vilazodone, or vartioxetine.

The systems and methods described anywhere herein may be used to administer a drug to treat pica.

The systems and methods described anywhere herein may be used to administer a drug to treat postpartum depression, such as sertraline, fluoxetine, citalopram, bupropion, escitalopram, venlafaxine, aripiprazole, buspirone, vortioxetine, or vilazodone.

The systems and methods described anywhere herein may be used to administer a drug to treat posttraumatic stress disorder, such as sertraline, fluoxetine, or paroxetine.

The systems and methods described anywhere herein may be used to administer a drug to treat premenstrual dysphoric disorder, such as estadiol, drospirenone, sertraline, citalopram, fluoxetine, or busiprone.

The systems and methods described anywhere herein may be used to administer a drug to treat pseudobulbar affect, such as dextromethorphan hydrobromide, or quinidine sulfate.

The systems and methods described anywhere herein may be used to administer a drug to treat pyromania, such as clozapine, asenapine, olanzapine, paliperidone, or quetiapine.

The systems and methods described anywhere herein may be used to administer a drug to treat reactive attachment disorder.

The systems and methods described anywhere herein may be used to administer a drug to treat reading disorder.

The systems and methods described anywhere herein may be used to administer a drug to treat rett's syndrome.

The systems and methods described anywhere herein may be used to administer a drug to treat rumination disorder.

The systems and methods described anywhere herein may be used to administer a drug to treat schizoaffective disorder, such as sertraline, carbamazepine, oxcarbazepine, valproate, haloperidol, olanzapine, or loxapine.

The systems and methods described anywhere herein may be used to administer a drug to treat schizophrenia, such as chlopromazine, haloperidol, fluphenazine, risperidone, quetiapine, ziprasidone, olanzapine, perphenazine, aripiprazole, or prochlorperazine.

The systems and methods described anywhere herein may be used to administer a drug to treat schizophreniform disorder, such as paliperidone, clozapine, risperidone.

The systems and methods described anywhere herein may be used to administer a drug to treat seasonal affective disorder, such as sertraline, or fluoxetine.

The systems and methods described anywhere herein may be used to administer a drug to treat separation anxiety disorder.

The systems and methods described anywhere herein may be used to administer a drug to treat shared psychotic disorder, such as clozapine, pimavanserin, risperidone, or lurasidone.

The systems and methods described anywhere herein may be used to administer a drug to treat social (pragmatic) communication disorder.

The systems and methods described anywhere herein may be used to administer a drug to treat social anxiety phobia, such as amitriptyline, bupropion, citalopram, fluoxetine, sertraline, or venlafaxine.

The systems and methods described anywhere herein may be used to administer a drug to treat somatic symptom disorder.

The systems and methods described anywhere herein may be used to administer a drug to treat specific phobia, such as diazepam, estazolam, quazepam, or alprazolam.

The systems and methods described anywhere herein may be used to administer a drug to treat stereotypic movement disorder, such as risperidone, or clozapine.

The systems and methods described anywhere herein may be used to administer a drug to treat stuttering.

The systems and methods described anywhere herein may be used to administer a drug to treat Tourette's disorder, such as haloperidol, fluphenazine, risperidone, ziprasidone, pimozide, perphenazine, or aripiprazole.

The systems and methods described anywhere herein may be used to administer a drug to treat transient tic disorder, such as guanfacine, clonidine, pimozide, risperidone, citalopram, escitalopram, sertraline, paroxetine, or fluoextine.

Figure 28:
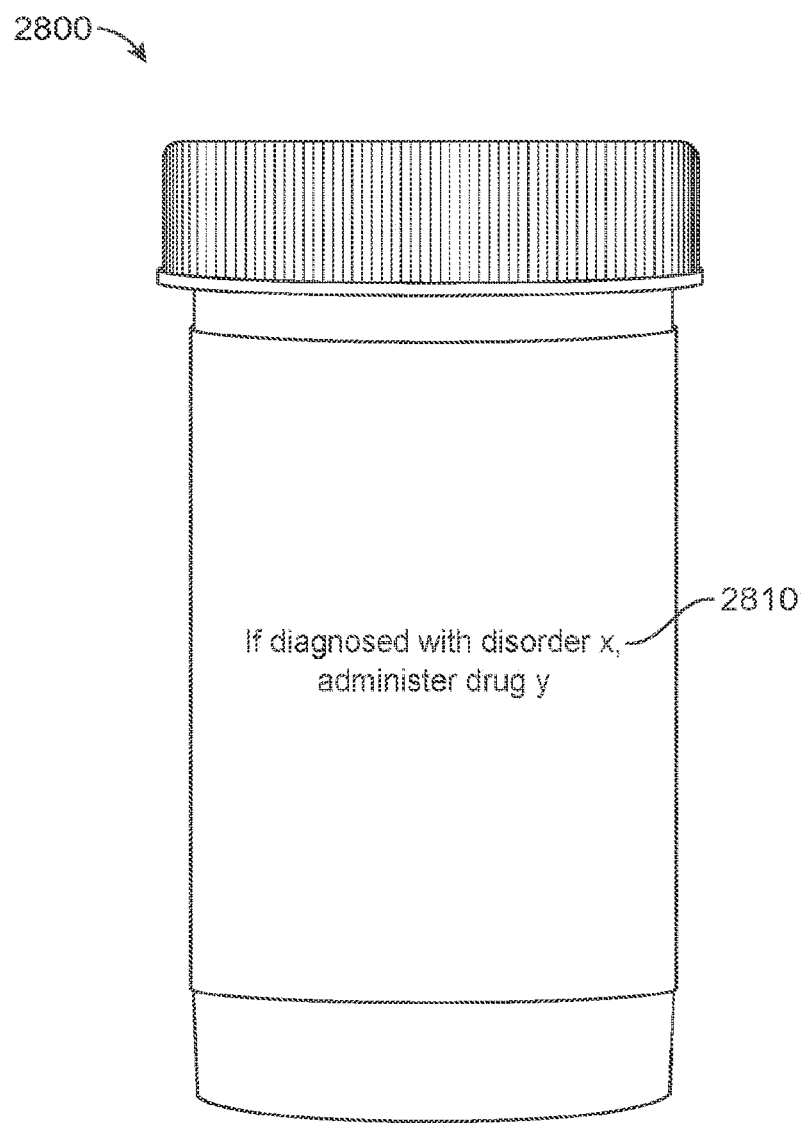
FIG. 28 shows a drug that may be administered in response to a diagnosis by the systems and methods described herein.

FIG. 28 shows a drug that may be administered in response to a diagnosis by the systems and methods described herein. The drug may be contained within a container 2800, such as a pill bottle. The container may have a label 2810 bearing instructions "If diagnosed with disorder x, administer drug y". The disorder x may be any disorder described herein. The drug y may be any drug described herein.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method comprising:
   (a) receiving input data of a subject comprising a plurality of features, wherein said plurality of features corresponds to one or more of a behavioral disorder, developmental disorder, or neurological disorder;
   (b) evaluating said input data using an assessment module comprising at least one tunable machine learning model that is configured to differentiate, based at least in part on said plurality of features, between at least one conclusive determination and an inconclusive determination with respect to a subject, thereby generating an evaluation result comprising said subject classification;
   (c) requesting additional data of said subject when said evaluation result comprises said inconclusive determination of said subject classification;
   (d) generating said at least one conclusive determination of said subject classification based at least in part on said additional data using said assessment module comprising said at least one tunable machine learning model, thereby updating said evaluation result to comprise said at least one conclusive determination of said subject classification, wherein said at least one conclusive determination indicates that said subject has one or more of said behavioral disorder, said developmental disorder, or said neurological disorder;
   (e) determining a personalized treatment plan for said subject based at least in part on said at least one conclusive determination of said subject classification, wherein said treatment plan comprises administering a therapeutic drug to said subject, wherein said therapeutic drug is selected based at least in part on said at least one conclusive determination of said subject classification;
   (f) monitoring said subject by periodically generating said at least one conclusive determination of said subject classification; and
   (g) sending a control signal, said control signal controlling a drug delivery device to administer said therapeutic drug to said subject according to said treatment plan.

2. The method of claim 1, wherein said assessment module is configured to apply at least one threshold range to differentiate between said at least one conclusive determination and said inconclusive determination with respect to said subject classification.

3. The method of claim 2, wherein said at least one threshold range configured to differentiate between said at least one conclusive determination and said inconclusive determination with respect to said subject classification is adjustable.

4. The method of claim 3, wherein a threshold range of said at least one conclusive determination decreases when a threshold range of said inconclusive determination increases.

5. The method of claim 4, wherein an accuracy of said at least one conclusive determination increases when said threshold range of said at least one conclusive determination decreases.

6. The method of claim 2, wherein said threshold range of said at least one conclusive determination or said inconclusive determination is based on an inclusion rate for said first categorical determination.

7. The method of claim 6, wherein said at least one conclusive determination is based on a specified sensitivity, a specified specificity, a specified negative predictive value, or a specified positive predictive value.

8. The method of claim 1, wherein said therapeutic drug is selected from the group consisting of:
risperidone, quetiapine, amphetamine, dextroamphetamine, methylphenidate, methamphetamine, dextroamphetamine, dexmethylphenidate, guanfacine, atomoxetine, lisdexamfetamine, clonidine, and aripiprazole.

9. The method of claim 1, wherein said assessment module comprises a chain of classifiers comprising a first classifier coupled to a second classifier.

10. The method of claim 9, wherein said assessment module is configured to evaluate said input data using said first classifier to generate a first output, and evaluate said first output using said second classifier to generate a second output.

11. The method of claim 10, wherein said assessment module is configured to determine said evaluation result based on said second output.

12. The method of claim 1, wherein said at least one machine learning model is generated using a machine learning algorithm comprising alternating decision tree (ADTree), Decision Stump, functional tree (FT), logistic model tree (LMT), logistic regression, Random Forest, linear classifier, support vector machine, neural network, or any combination thereof.

13. The method of claim 1, wherein said at least one machine learning model comprises a plurality of machine learning models used for ensemble analysis optimized using a machine learning ensemble meta-algorithm comprising AdaBoost, LPBoost, TotalBoost, BrownBoost, MadaBoost, or LogitBoost to reduce bias and/or variance.

14. The method of claim 1, wherein said input data comprises at least one of video-based features, audio-based features, interactive data, genetic markers, questionnaire data, or data obtained from a sensor, activity monitor, or wearable monitor.

15. The method of claim 1, further comprising obtaining said input data through a computing device comprising personal computer, a tablet, or a smartphone.

16. The method of claim 15, wherein at least a portion of said input data is obtained through a web-based interface.

17. The method of claim 1, wherein evaluating said input data using said assessment module at (b) is based at least in part on a ratio between conclusive determinations and inconclusive determinations.

18. A method comprising:
(a) receiving input data of a subject comprising a plurality of features, wherein said plurality of features corresponding to one or more of a behavioral disorder, developmental disorder, or neurological disorder;
(b) evaluating said input data using an assessment module comprising at least one tunable machine learning model configured to differentiate between at least one conclusive determination and an inconclusive determination with respect to a subject classification based on said plurality of features;
(c) combining scores for each of said at least one tunable machine learning model of said assessment module to generate a combined preliminary output score mapping said combined preliminary output score to said at least one conclusive determination, thereby generating an evaluation result comprising said subject classification of said subject;
(d) determining a personalized treatment plan for said subject based at least in part on said at least one conclusive determination of said subject classification, wherein said treatment plan comprises administering a therapeutic drug to said subject, wherein said therapeutic drug is selected based at least in part on said at least one conclusive determination of said subject classification;
(e) monitoring said subject by periodically generating said at least one conclusive determination of said subject classification; and
(f) sending a control signal, said control signal controlling a drug delivery device to administer said therapeutic drug to said subject according to said treatment plan.

19. A method comprising:
(a) receiving input data of a subject comprising a plurality of features, wherein said plurality of features corresponding to one or more of a behavioral disorder, developmental disorder, or neurological disorder;
(b) evaluating said input data using an assessment module comprising at least one machine learning model configured to differentiate between at least one conclusive determination and an inconclusive determination with respect to a subject classification based on said plurality of features, thereby generating an evaluation result comprising said at least one conclusive determination of said subject classification, wherein:
  i. said assessment module is configured to apply at least one threshold range, based on an inclusion rate of at least 70% for said first categorical determination, to differentiate between said at least one conclusive determination and said inconclusive determination with respect to said subject classification, and
  ii. said at least one conclusive determination is based on one or more of a sensitivity of at least 80% or a specificity of at least 80%;
(c) determining a personalized treatment plan for said subject based at least in part on said at least one conclusive determination of said subject classification, wherein said treatment plan comprises administering a therapeutic drug to said subject, wherein said therapeutic drug is selected based at least in part on said at least one conclusive determination of said subject classification;

(d) monitoring said subject by periodically generating said at least one conclusive determination of said subject classification; and
(e) sending a control signal, said control signal controlling a drug delivery device to administer said therapeutic drug to said subject according to said treatment plan.

* * * * *